(12) United States Patent
Murray et al.

(10) Patent No.: US 10,358,445 B2
(45) Date of Patent: Jul. 23, 2019

(54) RESPIRATORY FORMULATIONS AND COMPOUNDS FOR USE THEREIN

(71) Applicant: Respivert, Ltd., High Wycombe Buckinghamshire (GB)

(72) Inventors: Peter John Murray, London (GB); Stuart Thomas Onions, Nottingham (GB); Jonathan Gareth Williams, Nottingham (GB); Kevin Joly, Nottingham (GB)

(73) Assignee: RESPIVERT, LTD., High Wycombe Buckinghamshire (GB)

( * ) Notice: Subject to any disclaimer, the term of this patent is extended or adjusted under 35 U.S.C. 154(b) by 132 days.

(21) Appl. No.: 15/530,681

(22) Filed: Dec. 5, 2014

(65) Prior Publication Data

US 2018/0201611 A1    Jul. 19, 2018

Related U.S. Application Data

(62) Division of application No. 13/805,471, filed as application No. PCT/GB2011/051141 on Jun. 17, 2011, now Pat. No. 8,933,228.

(30) Foreign Application Priority Data

Jun. 17, 2010 (GB) .................................. 1010190.5
Jan. 31, 2011 (GB) .................................. 1101640.9

(51) Int. Cl.
| | | |
|---|---|---|
| C07D 471/04 | (2006.01) | |
| A61K 31/437 | (2006.01) | |
| A61K 31/4985 | (2006.01) | |
| C07D 487/04 | (2006.01) | |
| C07D 473/30 | (2006.01) | |
| C07D 475/02 | (2006.01) | |
| A61K 9/00 | (2006.01) | |

(52) U.S. Cl.
CPC .......... *C07D 471/04* (2013.01); *A61K 9/0075* (2013.01); *A61K 31/437* (2013.01); *A61K 31/4985* (2013.01); *C07D 473/30* (2013.01); *C07D 475/02* (2013.01); *C07D 487/04* (2013.01); *Y10T 428/2982* (2015.01)

(58) Field of Classification Search
None
See application file for complete search history.

(56) References Cited

U.S. PATENT DOCUMENTS 7,625,922 B2 * 12/2009 Niculescu-Duvaz ........................
C07D 471/04
514/300
8,198,279 B2 * 6/2012 Springer ............ A61K 31/4985
514/249
8,299,073 B2   10/2012 Ito et al.

| 8,618,289 B2 | 12/2013 | Abraham et al. |
|---|---|---|
| 8,933,228 B2 | 1/2015 | Murray et al. |
| 2006/0035922 A1 | 2/2006 | Mathias et al. |
| 2011/0212962 A1 | 9/2011 | Ito et al. |
| 2011/0269800 A1 | 11/2011 | Ito et al. |
| 2011/0294812 A1 | 12/2011 | Ito et al. |
| 2011/0312963 A1 | 12/2011 | Ito et al. |
| 2012/0136031 A1 | 5/2012 | Ito et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0156826 A1 | 6/2013 | Murray et al. |

FOREIGN PATENT DOCUMENTS

| WO | 2000043384 A1 | 7/2000 |
|---|---|---|
| WO | 2000055139 A2 | 9/2000 |
| WO | 2006043090 A1 | 4/2006 |

(Continued)

OTHER PUBLICATIONS

Pleschka et al., "Influenza virus propagation is impaired by inhibition of the Raf/MEK/ERK signaling cascade", Nature Cell Biology, vol. 3, pp. 301-305 XPOOII 72412 (Mar. 2001).
Mercado et al., "Formoterol restores costicosteroid sensitivity in severe asthma via p38 MAPK γ inhibition", American Thoracic Society Abstract, 2007.
Shmueli, O. et al., "GeneNote: whole genome expression profiles in normal human tissues", Comptes Rendus Biologies, 2003, 326(10-11):1067-1072/Genecard.
Smith, S. et al., "Inhibitory effect of p38 mitogen-activated protein kinase inhibitors on cytokine release from human macrophages", J. Br. J. Pharmacol., 2006, 149:393-404.

(Continued)

*Primary Examiner* — Heidi Reese
(74) *Attorney, Agent, or Firm* — McDermott Will & Emery LLP

(57) ABSTRACT

The present invention relates to respiratory formulations comprising a compound of formula (I):

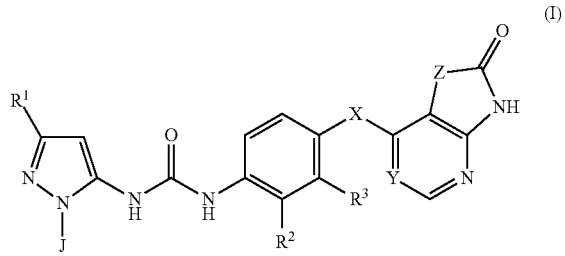

and use of said compounds and compositions in treatment, for example in the treatment of an inflammatory disease or a respiratory disorder, in particular an inflammatory mediated and/or virally mediated respiratory disorder such as asthma and COPD or the treatment or prevention of viral infection, for example infection by influenza virus, rhinovirus or RSV. The invention also extends to certain novel compounds of formula (I).

3 Claims, No Drawings

(56) References Cited

FOREIGN PATENT DOCUMENTS

| WO | 2007053394 A1 | 5/2007 |
|---|---|---|
| WO | 2008121666 A1 | 10/2008 |
| WO | 2008125014 A1 | 10/2008 |
| WO | 2009077766 A1 | 6/2009 |
| WO | 2009117080 A8 | 9/2009 |
| WO | 2009130487 A1 | 10/2009 |
| WO | 2010038085 A2 | 4/2010 |
| WO | 2010038086 A2 | 4/2010 |
| WO | 2010067130 A8 | 6/2010 |
| WO | 2010112936 A1 | 10/2010 |
| WO | 2011070368 A1 | 6/2011 |
| WO | 2011158039 A1 | 12/2011 |
| WO | 2011158042 A2 | 12/2011 |

OTHER PUBLICATIONS

Hale, K. K. et al., "Differential Expression and Activation of p38 Mitogen-Activated Protein Kinase α, β, γ and δ in Inflammatory Cell Lineages", J. Immunol., 1999, 162(7):4246-52.

Wang, X. S. et al., "Molecular Cloning and Characterization of a Novel p38 Mitogen-activated Protein Kinase", J. Biol. Chem., 1997, 272(38):23668-23674.

Court, N. W. et al., "Cardiac Expression and Subcellular Localization of the p38 Mitogen-activated Protein Kinase Member, Stress-activated Protein Kinase-3 (SAPK3)", J. Mol. Cell. Cardiol., 2002, 34(4):413-26.

Mertens, S. et al., "SAP kinase-3, a new member of the family of mammalian stress-activated protein kinases", FEES Lett., 1996, 383(3):273-6.

Kuma, Y. "BIRB796 inhibits all p38 MAPK isoforms in vitro and in vivo", J.Biol. Chem., 2005, 280: 194 72-194 79.

Underwood D.C. et al., "SB239063, a p38 MAPK inhibitor, reduces neutrophilia, inflammatory cytokines, MMP-9, and fibrosis in lung", Am. J. Physiol. Lung Cell. Mol. Phvsiol., 2000, 279:895-902.

Nath, P. et al., "Importance of p38 mitogen-activated protein kinase pathway in allergic airway remodeling and bronchial hyperresponsiveness ", Eur. J. Pharmacol., 2006, 544:160-167.

Medicherla S. et al., "p38 α-Selective Mitogen-Activated Protein Kinase Inhibitor SD-282 Reduces Inflammation in a Subchronic Model of Tobacco Smoke-Induced Airway Inflammation", J. Pharm. Exp. Ther., 2008, 324:921-929.

Lee et al., "MAP Kinase p38 Inhibitors: Clinical Results and an Intimate Look at Their Interactions with p38a Protein", Current Med. Chem., 2005, 12,:2979-2994.

Disse, B. et al., "Tiotropium (Spriva): Mechanistical Considerations and Clinical Profile in Obstructive Lung Disease", Life Sci 1999, 64: 457-464).

Menard et al., "Novel Potent BRAF Inhibitors: Toward 1 nM Comounds through Optimization of the Central Phenyl Ring", J. Med. Chem., 2009, 52(13), 2881-3991.

Zambon, Alfonso; et al., "Novel Hinge Binder Improves Activity and Pharmacokinetic Properties of BRAF Inhibitors", J. Med. Chem., 2010, 53(15), 5639-5655.

Suijkerbuijk, Bart M J M et al., "Development of novel, highly potent inhibitors of V-RAF murine sarcoma viral oncogene homologue B1 (BRAF): increasing cellular potency through optimization of a distal heteroaromatic group", Journal of Medicinal Chemistry (2010) 2741-2756 vol. 53 (7), American Chemical Society.

International Search Report PCT/EP2010/065746, dated Dec. 28, 2011 (RSP5011USPCT).

Japanese Notice of Rejection for corresponding Japanese application No. 2013-514789 dated May 27, 2015.

Nakanima, Katsuhisa et al., "Virus-Host Early Reaction", in Kagaku to Seibutsu (1989), vol. 27, No. 11,pp. 744-753.

International Search Report PCT/GB2011/051141, dated Dec. 28, 2011.

\* cited by examiner

RESPIRATORY FORMULATIONS AND COMPOUNDS FOR USE THEREIN

CROSS-REFERENCE TO RELATED APPLICATIONS

This application is a divisional of U.S. patent application Ser. No. 13/805,471, filed Dec. 19, 2012, which is a National Stage application under 35 U.S.C. 371 of PCT International Application No. PCT/GB2011/051141, filed Jun. 17, 2011, which claims priority from Great Britain Patent Application Number GB1010190.5, filed Jun. 17, 2010 and Great Britain Patent Application Number GB1101640.9, filed Jan. 31, 2011, the contents of which are hereby incorporated by reference in their entirety.

FIELD OF THE INVENTION

The invention relates to the use of certain compounds which are inhibitors of p38 mitogen-activated protein kinase enzymes (referred to herein as p38 MAPK inhibitors), particularly the alpha and gamma sub-types thereof, and pharmaceutical formulations comprising the same and their use in therapy, including in pharmaceutical combinations, especially in the treatment of inflammatory diseases and/or viral infection, including inflammatory diseases of the lung, such as asthma and chronic obstructive pulmonary disease (COPD). The disclosure also provides certain novel compounds and formulations comprising the same.

BACKGROUND OF THE INVENTION

Four p38 MAPK isoforms (alpha, beta, gamma and delta respectively) have been identified, each displaying a tissue-specific expression pattern. The p38 MAPK alpha and beta isoforms are ubiquitously expressed throughout the body and are found in many different cell types. The p38 MAPK alpha and beta isoforms are inhibited by certain previously described small molecule p38 MAPK inhibitors. Earlier generations of compounds were found to be highly toxic due to the ubiquitous expression pattern of these isoforms which resulted in off-target effects of the compounds. More recently, improved inhibitors have been identified that are highly selective for the p38 MAPK alpha and beta isoforms and demonstrate a wider safety margin.

Less is known about the p38 MAPK gamma and delta isoforms. These isoforms are expressed in specific tissues/cells (unlike the p38 alpha and p38 beta isoforms). The p38 MAPK-delta isoform is expressed more in the pancreas, testes, lung, small intestine and kidney. It is also abundant in macrophages and detectable in neutrophils, CD4+ T cells and endothelial cells (Shmueli, O. et al., *Comptes Rendus Biologies*, 2003, 326(10-11):1067-1072/Genecard; Smith, S. *J. Br. J. Pharmacol.*, 2006, 149:393-404; Hale, K. K., *J. Immunol.*, 1999, 162(7):4246-52; Wang, X. S. et al., *J. Biol. Chem.*, 1997, 272(38):23668-23674.) Very little is known about the expression of p38 MAPK gamma although it is expressed more highly in brain, skeletal muscle and heart, as well as in lymphocytes and macrophages. (Shmueli, O. et al., *Comptes Rendus Biologies*, 2003, 326(10-11):1067-1072/Genecard; Hale, K. K., *J. Immunol.*, 1999, 162(7): 4246-52: Court, N. W. et al., *J. Mol. Cell. Cardiol.*, 2002, 34(4):413-26; Mertens, S. et al., *FEBS Lett.*, 1996, 383(3): 273-6.)

Selective small molecule inhibitors of p38 MAPK gamma and delta isozymes are not currently available, although one existing compound, BIRB 796, is known to possess pan-isoform inhibitory activity. The p38 gamma and p38 delta inhibition is observed at higher concentrations of the compound than those required to inhibit p38 MAPK alpha, (Kuma, Y. *J. Biol. Chem.*, 2005, 280:19472-19479). BIRB 796 also impaired the phosphorylation of p38 MAPKs or JNKs by the upstream kinase MKK6 or MKK4. Kuma discussed the possibility that the conformational change caused by the binding of the inhibitor to the MAPK may affect the structure of both its phosphorylation site and the docking site for the upstream activator, therefore impairing the phosphorylation of p38 MAPKs or JNKs.

p38 MAP kinase is believed to play a pivotal role in many of the signalling pathways that are involved in initiating and maintaining chronic, persistent inflammation in human disease, for example, severe asthma and COPD. There is now abundant literature that demonstrates that p38 MAP kinase is activated by a range of pro-inflammatory cytokines and that its activation results in the recruitment and release of further pro-inflammatory cytokines. Indeed, data from some clinical studies demonstrate beneficial changes occur in the disease state of patients during treatment with p38 MAP kinase inhibitors. For instance Smith describes the inhibitory effect of p38 MAP kinase inhibitors on TNFα (but not IL-8) release from human PBMCs (Smith, S. J. *Br. J. Pharmacol*, 2006, 149:393-404). Use of inhibitors of p38 MAP kinase in the treatment of COPD is also proposed. Small molecule inhibitors targeted to p38 MAPKα/β have proved to be effective in reducing various parameters of inflammation in cells and tissues obtained from patients with COPD who are generally corticosteroid insensitive (Smith, S. *J. Br. J. Pharmacol.*, 2006, 149:393-404) and in vivo animal models (Underwood D. C. et al., *Am. J. Physiol. Lung Cell. Mol. Physiol.*, 2000, 279:895-902; Nath, P. et al., *Eur. J. Pharmacol.*, 2006, 544:160-167; Medicherla S. et al., *J. Pharm. Exp. Ther.*, 2008, 324:921-929.).

Irusen and colleagues also suggested the possibility of involvement of p38 MAPK α/β on corticosteroid insensitivity via reduction of binding affinity of glucocorticoid receptor (GR) in nuclei (Irusen, E. et al., *J. Allergy Clin. Immunol.*, 2002, 109:649-657). Clinical experience with a range of p38 MAP kinase inhibitors, including AMG548, BIRB 796, VX702, SCIO469 and SCIO323 has also been described (Lee, M. R. and Dominguez, C., *Current Med. Chem.*, 2005, 12:2979-2994.).

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al (Mercado N. et al, *American Thoracic Society Abstract*, 2007, A56) demonstrates that silencing p38 gamma has the potential to restore patient sensitivity to corticosteroids. Thus there may be a therapeutically significant dual benefit to the use of a p38 MAP kinase inhibitor for the treatment of COPD and severe asthma.

There is now a substantial body of evidence which strongly implicates the role of respiratory viral infections in initiating exacerbations in patients suffering from asthma and/or COPD. Exacerbations require an increase in treatment intensity to re-establish control of disease symptomology. If severe, exacerbations may well result in the hospitalisation or, at their most extreme, the death of patients.

The major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above. There remains a need to identify and develop new compounds that have improved therapeutic potential, in particular that are more efficacious, longer acting and/or less toxic at the relevant therapeutic dose. An objective of the present invention is to provide compounds which inhibit p38 MAP kinase with certain sub-type specificity, and that consequently show enhanced anti-inflammatory potential and/or anti-viral activity.

The compounds of the present disclosure possess profiles in therapeutically relevant in vitro systems that are consistent with a superior mode of action for treating inflammatory lung disease and in particular for treatment of the same by inhaled administration. The inhibitory effects of compounds versus HRV-16 replication and poly I:C induced ICAM-1 expression were also determined.

SUMMARY OF THE INVENTION

According to the invention, there is provided a compound of formula (I):

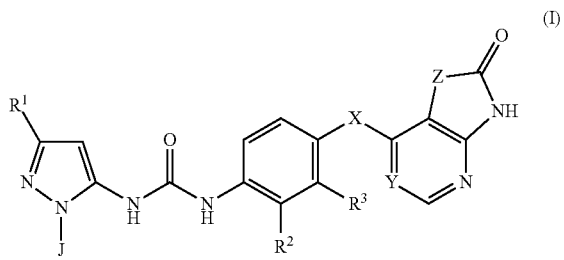

wherein J represents:

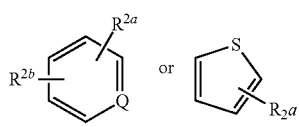

Q is N or —CH—;
X is O or O—CH$_2$—;
Y is —CH═ or N;
Z is O, NR$^4$, —CR$^{4a}$═N— or —N═CR$^{4a}$—, whereby the latter two groups, together with the atoms to which they are attached, form a 6 membered ring;
R$^1$ is C$_{1-6}$ alkyl, branched or unbranched, C$_{3-6}$ cycloalkyl, each optionally substituted by a hydroxyl group;
R$^{2a}$ is H, halo, saturated or unsaturated branched or unbranched C$_{1-8}$ alkylene chain, wherein one or more carbons (for example 1 to 3, such as 1, 2 or 3 carbons) are optionally replaced by a heteroatom(s) independently selected from —O—, —N— and/or S(O)$_m$ and the chain is optionally substituted by one or more halogen atoms (for example 1 to 6);
R$^{2b}$ is H, halo, C$_{1-6}$ alkoxy or C$_{1-6}$ alkyl optionally substituted by OH;
R$^2$ and R$^3$ each independently represent H, C$_{1-4}$ alkyl, halogen; C$_{1-4}$ haloalkyl, O(C$_{1-4}$ alkyl), O(C$_{1-4}$haloalkyl), CN, SO$_2$R$^5$, C(O)OR$^6$ with the proviso that R$^2$ and R$^3$ do not both represent H concomitantly, or R$^2$ and R$^3$ together with the carbons to which they are attached form a six membered aromatic ring or a heteroaromatic ring comprising a nitrogen atom;
R$^4$ is H, C$_{1-5}$ alkyl, C$_{2-5}$ alkenyl, C$_{2-5}$ alkynyl, C$_{3-6}$ cycloalkyl, C$_{3-6}$ cycloalkenyl, C$_6$ aryl, a 5 or 6 membered heteroaryl or a 5 or 6 membered heterocyclic group, wherein said aryl, heteroaryl or heterocyclic group is substituted with 0 to 3 substituents selected from halogen, hydroxyl, C$_{1-6}$ alkyl, C$_{1-6}$ alkoxy, C$_{1-6}$ haloalkyl, amino, C$_{1-4}$ mono or di-alkyl amino, C$_{1-4}$ mono or di-acyl amino, S(O)$_q$C$_{1-6}$ alkyl, C$_{0-6}$ alkylC(O)C$_{1-6}$ alkyl or C$_{0-6}$ alkylC(O)C$_{1-6}$ heteroalkyl;
R$^{4a}$ is H or C$_{1-3}$ alkyl;
R$^5$ is H or C$_{1-4}$ alkyl;
R$^6$ is H or C$_{1-4}$ alkyl;
m is 0, 1 or 2;
q is 0, 1 or 2;
or a pharmaceutically acceptable salt thereof, including all stereoisomers, tautomers and isotopic derivatives thereof, for example for use in the treatment of respiratory disorders or inflammatory diseases or in the treatment of viral infection.

In a specific embodiment, such compounds are provided for use in the treatment of inflammatory mediated and/or virally mediated respiratory disorders such as asthma and COPD.

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example —C$_{1-3}$ alkylOC$_{1-3}$ alkyl, such as —CH$_2$CH$_2$OCH$_3$ or —CH$_2$OCH$_3$. Thus in one embodiment the alkoxy is linked through carbon to the remainder of the molecule. In one embodiment the alkoxy is linked through oxygen to the remainder of the molecule, for example —C$_0$ alkylOC$_{1-6}$ alkyl. In one embodiment the disclosure relates to straight chain alkoxy.

Heteroalkyl as employed herein is intended to refer to a branched or straight chain alkyl wherein one or more, such as 1, 2 or 3 carbons are replaced by a heteroatom, selected from N, O or S(O)$_q$, wherein q represents 0, 1 or 2. The heteroatom may replace a primary, secondary or tertiary carbon, that is, for example, OH or NH$_2$ for CH$_3$, or NH or O or SO$_2$ for —CH$_2$— or N for a —CH— or a branched carbon group, as technically appropriate.

Haloalkyl as employed herein refers to alkyl groups having 1 to 6 halogen atoms, for example 1 to 5 halogens, such as per haloalkyl, in particular perfluoroalkyl, more specifically —CF$_2$CF$_3$ or CF$_3$.

C$_{1-4}$ mono or di-acyl amino is intended to refer to —NHC(O)C$_{1-3}$ alkyl and to (—NC(O)C$_{1-3}$ alkyl) C(O)C$_{1-3}$ alkyl) respectively. C$_{1-4}$ mono or di-alkyl amino is intended to refer to —NHC$_{1-4}$ alkyl and —N(C$_{1-4}$ alkyl) (C$_{1-4}$ alkyl) respectively.

Aryl as used herein refers to, for example C$_{6-14}$ mono or polycyclic groups having from 1 to 3 rings wherein at least one ring is aromatic including phenyl, naphthyl, anthracenyl, 1,2,3,4-tetrahydronaphthyl and the like, such as phenyl and naphthyl.

Heteroaryl is a 6 to 10 membered aromatic monocylic ring or bicyclic ring system wherein at least one ring is an aromatic nucleus comprising one or more, for example 1, 2, 3 or 4 heteroatoms independently selected from O, N and S. Examples of heteroaryls include: pyrrole, oxazole, thiazole, isothiazole, imidazole, pyrazole, isoxazole, pyridine, pyridazine, pyrimidine, pyrazine, benzothiophene, benzofuran, or 1, 2, 3 and 1, 2, 4 triazole.

Heterocyclyl as employed herein refers to a 5 to 6 membered saturated or partially unsaturated non-aromatic ring comprising one or more, for example 1, 2, 3 or 4 heteroatoms independently selected from O, N and S optionally one or two carbons in the ring may bear an oxo substituent. The definition of $C_{5-6}$ heterocycle as employed herein refers to a is a 5 to 6 membered saturated or partially unsaturated non-aromatic carbocyclic ring comprising one or more, for example 1, 2, 3 or 4 heteroatoms independently selected from O, N and S, wherein each heteroatom replaces a carbon atom and optionally one or two carbons may bear an oxo substituent.

Clearly any valancies of a heteroatom not employed in forming or retaining the ring structure may be filled by hydrogen or a substituent, as appropriate. Thus the substituents on heterocycles may be on carbon or on a heteroatom, such as nitrogen as appropriate. Examples of heterocycles and $C_{5-6}$ heterocycles include pyrroline, pyrrolidine, tetrahydrofuran, tetrahydrothiophene, pyrazoline, imidazoline, pyrazolidine, imidazolidine, oxoimidazolidine, dioxolane, thiazolidine, isoxazolidine, pyran, dihydropyran, piperidine, piperazine, morpholine, dioxane, thiomorpholine and oxathiane.

Halogen includes fluoro, chloro, bromo or iodo, in particular fluoro, chloro or bromo, especially fluoro or chloro.

Oxo as used herein refers to C=O and will usually be represented as C(O).

$C_{3-8}$ cycloalkyl as employed herein is intended to refer to a saturated or partially unsaturated non-aromatic ring containing 3 to 8 carbon atoms.

$C_{1-10}$ alkyl includes $C_2$, $C_3$, $C_4$, $C_5$, $C_6$, $C_7$, $C_8$ or $C_9$ as well as $C_1$ and $C_{10}$. $C_{0-8}$ alkyl includes $C_1$, $C_2$, $C_3$, $C_4$, $C_5$, $C_6$, or $C_7$ as well as $C_0$ and $C_8$.

In relation to a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, $S(O)_p$, wherein said chain is optionally, substituted by one or more groups independently selected from oxo, halogen, an aryl group, a heteroaryl group or a heterocyclyl group, it will be clear to persons skilled in the art that the heteroatom may replace a primary, secondary or tertiary carbon, that is the radicals: $CH_3$, —$CH_2$— or —CH— or a branched carbon group, as technically appropriate, wherein p is 0, 1 or 2.

In one embodiment of the disclosure there is provided compounds of formula (I), wherein $R^1$ is $C_{1-6}$ alkyl, for example methyl, ethyl, propyl, iso-propyl, butyl or tert-butyl, in particular ethyl, iso-propyl or tert-butyl such as tert-butyl.

In one embodiment of the disclosure there is provided compounds of formula (I), wherein $R^1$ is $C_{3-6}$ cycloalkyl.

In one embodiment $R^1$ represents $C_{1-6}$ alkyl or branched or unbranched, $C_{3-6}$ cycloalkyl, each substituted by a hydroxyl group.

In one embodiment $R^1$ is —$C(CH_3)_2CH_2OH$.

In one embodiment $R^2$ is halogen such as halo such as chloro.

In one embodiment $R^2$ is —$OCH_3$.

In one embodiment $R^2$ is H.

In one embodiment $R^{2a}$ is methyl, ethyl, n-propyl, iso-propyl, n-butyl or tert-butyl, in particular methyl.

In one embodiment, $R^{2a}$ represents branched or unbranched $C_{1-6}$ alkyl substituted by a hydroxyl group In one embodiment $R^{2a}$ is —$CH_2OH$.

In one embodiment $R^{2a}$ is —$OCH_3$.

In one embodiment $R^{2a}$ is —$SO_2CH_3$.

In one embodiment $R^{2a}$ is methyl, methoxy or —$C(CH_3)CH_2OH$, in particular —$C(CH_3)CH_2OH$.

In one embodiment $R^{2a}$ is in the 2, 3, or 4 position (i.e. ortho, meta or para position), in particular the para (4) position.

In one embodiment $R^{2b}$ is H.

In one embodiment $R^{2a}$ and $R^{2b}$ are not independently selected from F, Cl, Br, I, $C_{1-4}$ alkyl, OH, $OC_{1-4}$ alkyl, $CF_3$, $OCF_3$ and $SO_2C_{1-4}$ alkyl.

In one embodiment $R^{2a}$ and $R^{2b}$ do not both represent H.

In one embodiment where Q represents CH the phenyl ring bearing $R^{2a}$ and $R^{2b}$ is selected from:

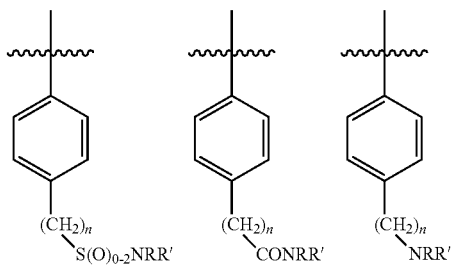

wherein n represents 0, 1 or 2

R represents H or $C_{1-4}$ alkyl,

R' represents H or $C_{1-4}$ alkyl, and

indicates where the fragment is joined to the remainder of the molecule.

In one embodiment where Q represents CH the phenyl ring bearing $R^{2a}$ and $R^{2b}$ is:

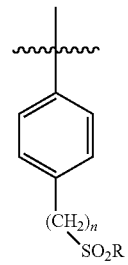

wherein n represents 1 or 2

R represents H or $C_{1-4}$ alkyl, and

indicates where the fragment is joined to the remainder of the molecule.

In one embodiment $R^3$ is H.

In one embodiment $R^3$ is halogen such as halo such as chloro.

In one embodiment $R^2$ and $R^3$ represent halogen, such as chloro.

In one embodiment $R^2$ and $R^3$ together with the carbons to which they are attached form a six membered aromatic ring such that together with the phenyl to which they are attached they form a core bicyclic ring structure which is a naphthyl.

In one embodiment $R^2$ and $R^3$ together with the carbons to which they are attached form a six membered heteroaromatic ring comprising a nitrogen atom, for example to provide a bicyclic heteroaromatic system, such as quinoline or isoquinoline.

In one embodiment $R^4$ is H, $C_{1-5}$ alkyl, $C_{2-5}$ alkenyl, $C_{2-5}$ alkynyl, $C_{3-6}$ cycloalkyl, $C_{3-6}$ cycloalkenyl, for example H, methyl, vinyl, allyl, ethynyl, prop-2-ynyl or cyclopropyl, such as H or methyl.

In one embodiment $R^4$ is $C_{1-4}$ alkyl such as methyl. In one embodiment $R^4$ is H.

In one embodiment $R^4$ is phenyl substituted with 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $S(O)_q C_{1-6}$ alkyl, $C_{0-6}$ alkylC(O)C$_{1-6}$ alkyl or $C_{0-6}$ alkylC(O)C$_{1-6}$ heteroalkyl.

In one embodiment $R^4$ is a 5 or 6 membered heteroaryl such as pyridine substituted with 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $S(O)_q C_{1-6}$ alkyl, $C_{0-6}$ alkylC(O)C$_{1-6}$ alkyl or $C_{0-6}$ alkylC(O)C$_{1-6}$ heteroalkyl.

In one embodiment $R^4$ is a 5 or 6 membered heterocyclic group such as piperidine, piperazine or morpholinyl substituted on carbon or nitrogen with 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $S(O)_q C_{1-6}$ alkyl, $C_{0-6}$ alkylC(O)C$_{1-6}$ alkyl or $C_{0-6}$ alkylC(O)C$_{1-6}$ heteroalkyl.

In one embodiment Z is O or $NR^4$, such as $NR^4$.

In one embodiment Z is $CR^{4a}$=N—. In another embodiment Z is —N=$CR^{4a}$.

In one embodiment $R^{4a}$ is H or methyl, such as H.

In one embodiment $R^5$ is H or $C_{1-4}$ alkyl, such as H or methyl.

In one embodiment $R^6$ is H or $C_{1-4}$ alkyl, such as H or methyl.

In one embodiment $R^5$ and $R^6$ are H.

In one embodiment $R^5$ and $R^6$ are $C_{1-4}$ alkyl, such methyl.

In one embodiment J represents phenyl optionally substituted by $R^{2a}$ and $R^{2b}$ each of which are defined above, or thienyl optionally substituted by $R^{2a}$, in particular phenyl such as tolyl or para methoxyphenyl.

In one embodiment J represents pyridinyl optionally substituted by $R^{2a}$ and $R^{2b}$ each of which are defined above.

In one embodiment X is O.

In one embodiment X is OCH$_2$.

In one embodiment Y is —CH=.

In one embodiment Y is N.

In one embodiment there is provided a compound of formula (Ia):

(Ia)

wherein J represents:

wherein:
Z is O, —NR$^4$ or —N=CR$^{4a}$— wherein the latter group, together with the atoms to which it is attached, forms a 6 membered ring, and
X is —OCH$_2$—, and
R$^1$, R$^2$, R$^{2a}$, R$^{2b}$, R$^3$, R$^{4a}$, Q and Y are defined above for compounds of formula (I).

In one embodiment of compounds of formula (Ia) Z is —NR$^4$ or —N=CR$^{4a}$—.

In one embodiment of compounds of formula (Ia) Z is —N=CR$^{4a}$. In one embodiment of compounds of formula (Ia) Y is N. In one embodiment of compounds of formula (Ia) Y is CH.

In one embodiment there is provided a compound of formula (Ib):

(Ib)

wherein J represents:

wherein:
Z is O, —NR$^4$ or —N=CR$^{4a}$— wherein the latter group, together with the atoms to which it is attached, forms a 6 membered ring, and
R$^1$, R$^2$, R$^{2a}$, R$^{2b}$, R$^3$, R$^4$, Q and X are defined above for compounds of formula (I).

In particular in compounds of formula (Ib) Z represents —NR$^4$ or —N=CR$^{4a}$—.

In particular in compounds of formula (Ib) Z represents —N=CR$^{4a}$— and, for example R$^{2a}$ and R$^{2b}$ are not independently selected from F, Cl, Br, I, C$_{1-4}$ alkyl, OH, OC$_{1-4}$ alkyl, CF$_3$, OCF$_3$ and SO$_2$C$_{1-4}$ alkyl.

In one embodiment there is provided a compound of formula (Ic):

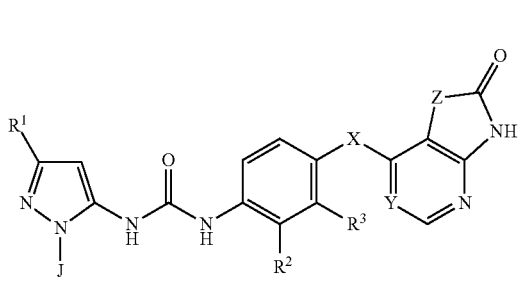

(Ic)

wherein J represents:

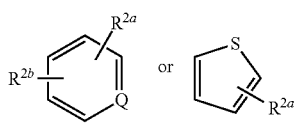

wherein:

Z is —NR$^4$ or —N=CR$^{4a}$— wherein the latter group, together with the atoms to which it is attached, forms a 6 membered ring, R$^{2b}$ is C$_{1-6}$ alkyl substituted by OH, and R$^1$, R$^2$, R$^{2a}$, R$^3$, R$^{4a}$, Q, X and Y are defined above for compounds of formula (I).

In one embodiment of compounds of formula (Ic) Z represents —NR$^4$ or —N=CR$^{4a}$—.

In one embodiment of compounds of formula (Ic) Z is —N=CR$^{4a}$. In one embodiment of compounds of formula (Ic) Y is CH. In one embodiment of compounds of formula (Ic) R$^{2a}$ is hydrogen.

In one embodiment there is provided a compound of formula (Id):

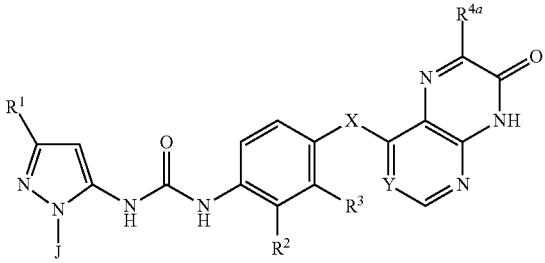

(Id)

wherein J represents:

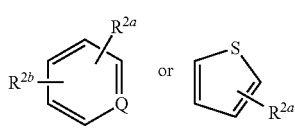

wherein:

R$^1$, R$^2$, R$^{2a}$, R$^{2b}$, R$^3$, R$^{4a}$, Q, X and Y are defined above for compounds of formula (I).

In one embodiment of compounds of formula (Id) R$^{2a}$ and R$^{2b}$ are not independently selected from F, Cl, Br, I, C$_{1-4}$ alkyl, OH, OC$_{1-4}$ alkyl, CF$_3$, OCF$_3$ and SO$_2$C$_{1-4}$ alkyl. In one embodiment of compounds of formula (Id) Y is CH.

In one embodiment there is provided a compound of formula (II):

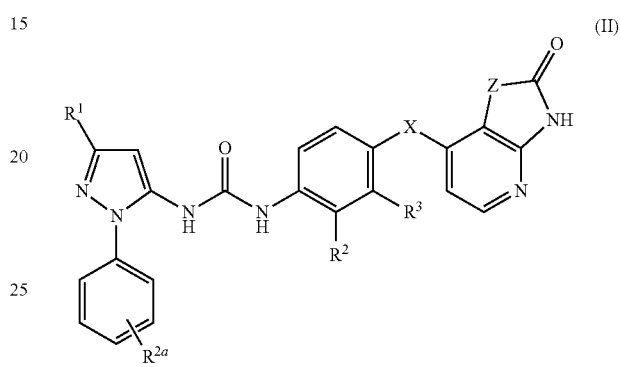

(II)

wherein R$^1$, R$^2$, R$^{2a}$, R$^3$ and X are as defined above and Z represents NH or O, such as NH.

In one embodiment there is provided a compounds of formula (III):

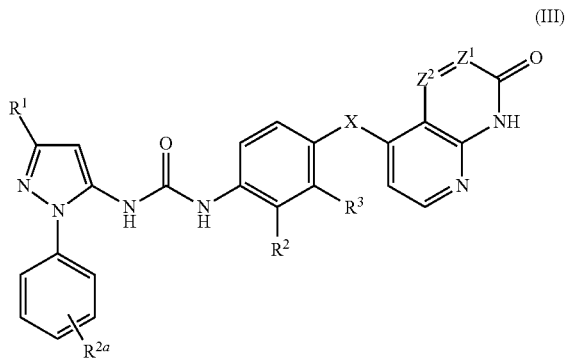

(III)

wherein R$^1$, R$^2$, R$^{2a}$, R$^3$ and X are as defined above and Z$^1$ and Z$^2$ independently represent N or CR$^{4a}$, with the proviso that Z$^1$ and Z$^2$ do not concomitantly represent N and do not concomitantly represent CR$^{4a}$.

In one embodiment of compounds of formula (III) Z$^1$ represents N and Z$^2$ represents CR$^{4a}$. In another embodiment of compound of formula (III) Z$^1$ represents CR$^{4a}$ and Z$^2$ represents N.

In one embodiment there is provided a compound of formula (IIIa):

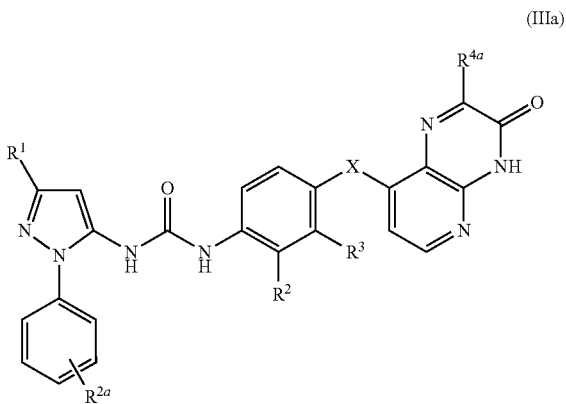

wherein $R^1$, $R^2$, $R^{2a}$, $R^3$, $R^{4a}$ and X are as defined above for compounds of formula (I).

In one embodiment of compounds of formula (IIIa) $R^{2a}$ does not represent, F, Cl, Br, I, $C_{1-4}$ alkyl, OH, $OC_{1-4}$ alkyl, $CF_3$, $OCF_3$ or $SO_2C_{1-4}$ alkyl.

Certain compounds of formula (I), (Ia), (Ib), (Ic), (Id), (II), (III) and (IIIa) are new and form an aspect of the invention.

Compounds of formula (I), (II) and (III) where $R^2$ and $R^3$ each independently represent H, $C_1$-$C_4$ alkyl, halogen; $C_1$-$C_4$ haloalkyl, $O(C_1$-$C_4$ alkyl); with the proviso that $R^2$ and $R^3$ do not both represent H concomitantly, or $R^2$ and $R^3$ together with the carbons to which they are attached form a six membered aromatic ring, i.e. substituted phenyl compounds and naphthyl compounds according to the present invention are new and form an aspect of the present disclosure.

Embodiments given for variables defined in compounds of formula (I) apply equally to compounds of formula (Ia), (Ib), (Ic), (Id), (II), (III) and (IIIa), as technically appropriate.

In one embodiment the compound is:
1-(3-tert-butyl-1-p-tolyl-1H-pyrazol-5-yl)-3-(4-(2-morpholinoethoxy)naphthalen-1-yl)urea;
N-(4-((4-(3-(3-tert-butyl-1-p-tolyl-1H-pyrazol-5-yl)ureido)naphthalen-1-yloxy)methyl)pyridin-2-yl)-2-methoxyacetamide;
N-(4-(4-(3-(3-tert-butyl-1-p-tolyl-1H-pyrazol-5-yl)ureido)naphthalen-1-yloxy)pyridin-2-yl)-2-methoxyacetamide;
1-(3-tert-butyl-1-phenyl-1H-pyrazol-5-yl)-3-(4-(2-oxo-2,3-dihydro-1H-imidazo[4,5-b]pyridin-7-yloxy)naphthalen-1-yl)urea;
1-(3-tert-butyl-1-p-tolyl-1H-pyrazol-5-yl)-3-(4-(2-oxo-2,3-dihydro-1H-imidazo[4,5-b]pyridin-7-yloxy)naphthalen-1-yl)urea;
1-(3-tert-butyl-1-(4-methoxyphenyl)-1H-pyrazol-5-yl)-3-(4-(2-oxo-2,3-dihydro-1H-imidazo[4,5-b]pyridin-7-yloxy)naphthalen-1-yl)urea;
1-(3-tert-butyl-1-p-tolyl-1H-pyrazol-5-yl)-3-(4-(1-methyl-2-oxo-2,3-dihydro-1H-imidazo[4,5-b]pyridin-7-yloxy)naphthalen-1-yl)urea;
1-(3-tert-butyl-1-(4-methoxyphenyl)-1H-pyrazol-5-yl)-3-(4-(1-methyl-2-oxo-2,3-dihydro-1H-imidazo[4,5-b]pyridin-7-yloxy)naphthalen-1-yl)urea;
1-(3-tert-butyl-1-phenyl-1H-pyrazol-5-yl)-3-(8-(2-oxo-2,3-dihydro-1H-imidazo[4,5-b]pyridin-7-yloxy)quinolin-5-yl)urea;
1-(3-tert-butyl-1-(4-methoxyphenyl)-1H-pyrazol-5-yl)-3-(8-(2-oxo-2,3-dihydro-1H-imidazo[4,5-b]pyridin-7-yloxy)quinolin-5-yl)urea;

or a pharmaceutically acceptable salt of any one thereof, including all stereoisomers, tautomers and isotopic derivatives thereof.

In one embodiment the compound is:
1-(3-tert-butyl-1-p-tolyl-1H-pyrazol-5-yl)-3-(4-(2-oxo-2,3-dihydro-1H-imidazo[4,5-b]pyridin-7-yloxy)naphthalen-1-yl)urea;
1-(3-tert-butyl-1-(4-methoxyphenyl)-1H-pyrazol-5-yl)-3-(4-(2-oxo-2,3-dihydro-1H-imidazo[4,5-b]pyridin-7-yloxy)naphthalen-1-yl)urea;
1-(3-tert-butyl-1-phenyl-1H-pyrazol-5-yl)-3-(4-(2-oxo-2,3-dihydro-1H-imidazo[4,5-b]pyridin-7-yloxy)naphthalen-1-yl)urea;
1-(3-tert-butyl-1-p-tolyl-1H-pyrazol-5-yl)-3-(4-(1-methyl-2-oxo-2,3-dihydro-1H-imidazo[4,5-b]pyridin-7-yloxy)naphthalen-1-yl)urea;
1-(3-tert-butyl-1-(4-methoxyphenyl)-1H-pyrazol-5-yl)-3-(4-(1-methyl-2-oxo-2,3-dihydro-1H-imidazo[4,5-b]pyridin-7-yloxy)naphthalen-1-yl)urea;
1-(3-tert-butyl-1-phenyl-1H-pyrazol-5-yl)-3-(8-(2-oxo-2,3-dihydro-1H-imidazo[4,5-b]pyridin-7-yloxy)quinolin-5-yl)urea;
1-(3-tert-butyl-1-(4-methoxyphenyl)-1H-pyrazol-5-yl)-3-(8-(2-oxo-2,3-dihydro-1H-imidazo[4,5-b]pyridin-7-yloxy)quinolin-5-yl)urea;
1-(3-(tert-butyl)-1-phenyl-1H-pyrazol-5-yl)-3-(4-((3-oxo-3,4-dihydropyrido[2,3-b]pyrazin-8-yl)oxy)naphthalen-1-yl)urea;
1-(3-(tert-butyl)-1-(p-tolyl)-1H-pyrazol-5-yl)-3-(4-((3-oxo-3,4-dihydropyrido[2,3-b]pyrazin-8-yl)oxy)naphthalen-1-yl)urea;
1-(3-(tert-butyl)-1-phenyl-1H-pyrazol-5-yl)-3-(4-((2-methyl-3-oxo-3,4-dihydropyrido[2,3-b]pyrazin-8-yl)oxy)naphthalen-1-yl)urea;
1-(3-(tert-butyl)-1-(p-tolyl)-1H-pyrazol-5-yl)-3-(4-((2-methyl-3-oxo-3,4-dihydropyrido[2,3-b]pyrazin-8-yl)oxy)naphthalen-1-yl)urea;
1-(3-(tert-Butyl)-1-(4-methoxyphenyl)-1H-pyrazol-5-yl)-3-(4-((2-oxo-2,3-dihydro-1H-imidazo[4,5-b]pyridin-7-yl)oxy)naphthalen-1-yl)urea;
1-(3-(tert-Butyl)-1-(4-methoxyphenyl)-1H-pyrazol-5-yl)-3-(4-((1-methyl-2-oxo-2,3-dihydro-1H-imidazo[4,5-b]pyridin-7-yl)oxy)naphthalen-1-yl)urea;
1-(3-(tert-Butyl)-1-(4-methoxyphenyl)-1H-pyrazol-5-yl)-3-(4-((1-ethyl-2-oxo-2,3-dihydro-1H-imidazo[4,5-b]pyridin-7-yl)oxy)naphthalen-1-yl)urea;
1-(3-(tert-Butyl)-1-(4-methoxyphenyl)-1H-pyrazol-5-yl)-3-(4-((1-isopropyl-2-oxo-2,3-dihydro-1H-imidazo[4,5-b]pyridin-7-yl)oxy)naphthalen-1-yl)urea;
1-(3-(tert-Butyl)-1-(4-methoxyphenyl)-1H-pyrazol-5-yl)-3-(2,3-d ichloro-4-((1-methyl-2-oxo-2,3-dihydro-1H-imidazo[4,5-b]pyridin-7-yl)oxy)phenyl)urea;
1-(3-(tert-Butyl)-1-(4-methoxyphenyl)-1H-pyrazol-5-yl)-3-(8-((2-oxo-2,3-dihydro-1H-imidazo[4,5-b]pyridin-7-yl)oxy)quinolin-5-yl)urea;
1-(3-(tert-Butyl)-1-(p-tolyl)-1H-pyrazol-5-yl)-3-(4-((8-oxo-8,9-dihydro-7H-purin-6-yl)oxy) naphthalen-1-yl)urea;
1-(3-(tert-Butyl)-1-(4-hydroxyphenyl)-1H-pyrazol-5-yl)-3-(4-((3-oxo-3,4-dihydropyrido[2,3-b]pyrazin-8-yl)oxy)naphthalen-1-yl)urea;
1-(3-(tert-Butyl)-1-(4-(hydroxymethyl)phenyl)-1H-pyrazol-5-yl)-3-(4-((3-oxo-3,4-dihydropyrido[2,3-b]pyrazin-8-yl)oxy)naphthalen-1-yl)urea;
1-(3-(tert-Butyl)-1-(4-(hydroxymethyl)-3-methoxyphenyl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-methoxyphenyl)-1H-pyrazol-5-yl)-3-(2,3-dichloro-4-((3-oxo-3,4-dihydropyrido[2,3-b]pyrazin-8-yl)oxy)phenyl)urea;

1-(3-(tert-Butyl)-1-(6-methoxypyridin-3-yl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(5-methylthiophen-2-yl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-methoxyphenyl)-1H-pyrazol-5-yl)-3-(4-((7-oxo-7,8-dihydropteridin-4-yl)oxy)naphthalen-1-yl)urea;

1-(3-(tert-butyl)-1-(6-methoxypyridin-3-yl)-1H-pyrazol-5-yl)-3-(4-((1-methyl-2-oxo-2,3-dihydro-1H-imidazo[4,5-b]pyridin-7-yl)oxy)naphthalen-1-yl)urea;

1-(3-(tert-butyl)-1-(4-methoxyphenyl)-1H-pyrazol-5-yl)-3-(4-((3-oxo-3,4-dihydropyrido[2,3-b]pyrazin-8-yl)oxy)naphthalen-1-yl)urea;

1-(4-(3-(tert-butyl)-5-(3-(4-((3-oxo-3,4-dihydropyrido[2,3-b]pyrazin-8-yl)oxy)naphthalen-1-yl)ureido)-1H-pyrazol-1-yl)phenyl)-N-methylmethanesulfonamide;

1-(3-(tert-butyl)-1-(4-chlorophenyl)-1H-pyrazol-5-yl)-3-(4-((3-oxo-3,4-dihydropyrido[2,3-b]pyrazin-8-yl)oxy)naphthalen-1-yl)urea;

1-(3-cyclopropyl-1-(p-tolyl)-1H-pyrazol-5-yl)-3-(4-((3-oxo-3,4-dihydropyrido[2,3-b]pyrazin-8-yl)oxy)naphthalen-1-yl)urea;

1-(3-(1-methylcyclopropyl)-1-(p-tolyl)-1H-pyrazol-5-yl)-3-(4-((3-oxo-3,4-dihydropyrido[2,3-b]pyrazin-8-yl)oxy)naphthalen-1-ylurea;

1-(3-isopropyl-1-(p-tolyl)-1H-pyrazol-5-yl)-3-(4-((3-oxo-3,4-dihydropyrido[2,3-b]pyrazin-8-yl) oxy)naphthalen-1-yl)urea;

1-(3-(tert-butyl)-1-(4-(methylsulfonyl)phenyl)-1H-pyrazol-5-yl)-3-(4-((3-oxo-3,4-dihydropyrido[2,3-b]pyrazin-8-yl)oxy)naphthalen-1-yl)urea;

1-(3-(tert-butyl)-1-(3,4-dichlorophenyl)-1H-pyrazol-5-yl)-3-(4-((3-oxo-3,4-dihydropyrido[2,3-b]pyrazin-8-yl)oxy)naphthalen-1-yl)urea;

1-(3-(tert-butyl)-1-(4-(methylthio)phenyl)-1H-pyrazol-5-yl)-3-(4-((3-oxo-3,4-dihydropyrido[2,3-b]pyrazin-8-yl)oxy)naphthalen-1-yl)urea or a pharmaceutically acceptable salt of any one thereof, including all stereoisomers, tautomers and isotopic derivatives thereof.

In one embodiment the compound is:

1-(3-tert-butyl-1-(4-methoxyphenyl)-1H-pyrazol-5-yl)-3-(4-(2-oxo-2,3-dihydro-1H-imidazo[4,5-b]pyridin-7-yloxy)naphthalen-1-yl)urea;

1-(3-tert-butyl-1-(4-methoxyphenyl)-1H-pyrazol-5-yl)-3-(4-(1-methyl-2-oxo-2,3-dihydro-1H-imidazo[4,5-b]pyridin-7-yloxy)naphthalen-1-yl)urea;

1-(3-tert-butyl-1-(4-methoxyphenyl)-1H-pyrazol-5-yl)-3-(8-(2-oxo-2,3-dihydro-1H-imidazo[4,5-b]pyridin-7-yloxy)quinolin-5-yl)urea;

1-(3-(tert-Butyl)-1-(4-methoxyphenyl)-1H-pyrazol-5-yl)-3-(4-((2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(4-((1-methyl-2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(4-((1-ethyl-2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(4-((1-isopropyl-2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(2,3-dichloro-4-((1-methyl-2-oxo-2,3-dihydro-1H-imidazo[4,5-b]pyridin-7-yl)oxy)phenyl)urea;

1-(3-(tert-Butyl)-1-(4-methoxyphenyl)-1H-pyrazol-5-yl)-3-(8-((2-oxo-2,3-dihydro-1H-imidazo[4,5-b]pyridin-7-yl)oxy)quinolin-5-yl)urea;

1-(3-(tert-Butyl)-1-(p-tolyl)-1H-pyrazol-5-yl)-3-(4-((8-oxo-8,9-dihydro-7H-purin-6-yl)oxy) naphthalen-1-yl)urea;

1-(3-(tert-Butyl)-1-(4-hydroxyphenyl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-(hydroxymethyl)phenyl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-(hydroxymethyl)-3-methoxyphenyl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-methoxyphenyl)-1H-pyrazol-5-yl)-3-(2,3-dichloro-4-((3-oxo-3,4-dihydropyrido[2,3-b]pyrazin-8-yl)oxy)phenyl)urea;

1-(3-(tert-Butyl)-1-(6-methoxypyridin-3-yl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(5-methylthiophen-2-yl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-methoxyphenyl)-1H-pyrazol-5-yl)-3-(4-((7-oxo-7,8-dihydropteridin-4-yl)oxy)naphthalen-1-yl)urea;

1-(3-(tert-butyl)-1-(6-methoxypyridin-3-yl)-1H-pyrazol-5-yl)-3-(4-((1-methyl-2-oxo-2,3-dihydro-1H-imidazo[4,5-b]pyridin-7-yl)oxy)naphthalen-1-yl)urea;

1-(3-(tert-butyl)-1-(4-methoxyphenyl)-1H-pyrazol-5-yl)-3-(4-((3-oxo-3,4-dihydropyrido[2,3-b]pyrazin-8-yl)oxy)naphthalen-1-yl)urea;

1-(4-(3-(tert-butyl)-5-(3-(4-((3-oxo-3,4-dihydropyrido[2,3-b]pyrazin-8-yl)oxy)naphthalen-1-yl)ureido)-1H-pyrazol-1-yl)phenyl)-N-methylmethanesulfonamide;

1-(3-(tert-butyl)-1-(4-chlorophenyl)-1H-pyrazol-5-yl)-3-(4-((3-oxo-3,4-dihydropyrido[2,3-b]pyrazin-8-yl)oxy)naphthalen-1-yl)urea;

1-(3-cyclopropyl-1-(p-tolyl)-1H-pyrazol-5-yl)-3-(4-((3-oxo-3,4-dihydropyrido[2,3-b]pyrazin-8-yl)oxy)naphthalen-1-yl)urea;

1-(3-(1-methylcyclopropyl)-1-(p-tolyl)-1H-pyrazol-5-yl)-3-(4-((3-oxo-3,4-dihydropyrido[2,3-b]pyrazin-8-yl)oxy)naphthalen-1-ylurea;

1-(3-isopropyl-1-(p-tolyl)-1H-pyrazol-5-yl)-3-(4-((3-oxo-3,4-dihydropyrido[2,3-b]pyrazin-8-yl) oxy)naphthalen-1-yl)urea;

1-(3-(tert-butyl)-1-(4-(methylsulfonyl)phenyl)-1H-pyrazol-5-yl)-3-(4-((3-oxo-3,4-dihydropyrido[2,3-b]pyrazin-8-yl)oxy)naphthalen-1-yl)urea;

1-(3-(tert-butyl)-1-(3,4-dichlorophenyl)-1H-pyrazol-5-yl)-3-(4-((3-oxo-3,4-dihydropyrido[2,3-b]pyrazin-8-yl)oxy)naphthalen-1-yl)urea;

1-(3-(tert-butyl)-1-(4-(methylthio)phenyl)-1H-pyrazol-5-yl)-3-(4-((3-oxo-3,4-dihydropyrido[2,3-b]pyrazin-8-yl)oxy)naphthalen-1-yl)urea or a pharmaceutically acceptable salt of any one thereof, including all stereoisomers, tautomers and isotopic derivatives thereof Examples of salts of compound (I) include all pharmaceutically acceptable salts, such as, without limitation, acid addition salts of strong mineral acids such as HCl and HBr salts and addition salts of strong organic acids such as a methansulfonic acid salt.

The disclosure herein extends to solvates of compounds of formula (I). Examples of solvates include hydrates.

The compounds of the disclosure include those where the atom specified is replaced by a naturally occurring or non-naturally occurring isotope. In one embodiment the isotope is a stable isotope. Thus the compounds of the disclosure include, for example deuterium containing compounds and the like.

The compounds described herein may include one or more chiral centres, and the disclosure extends to include racemates, enantiomers and stereoisomers resulting therefrom. In one embodiment one enantiomeric form is present in a substantially purified form that is substantially free of the corresponding enantiomeric form.

The disclosure also extends to all polymorphic forms of the compounds herein defined.

In some embodiments of the invention the structures of certain compounds render them subject to tautomerism. For example a keto group may display keto/enol tautomerism and an amide group may exhibit amide/imino alcohol tautomersim.

In those embodiments of the invention in which tautomerism is either present or possible any reference or representation of any tautomers is intended to include all other tautomers of the said compound or compounds.

Unless the context indicates otherwise references to compounds of formula (I) herein includes references to one or more, such as all structures and compounds disclosed including compounds of formula (II) and (III).

Compounds according to the present invention can be prepared by methods described or analogous to those described in WO2006/043090, WO2009/130487 and WO2010/038086.

Certain compounds of formula (I) wherein $R^2$ and $R^3$ together with the phenyl to which they are attached represents substituted phenyl or naphthyl can be prepared by reacting a compound of formula (IV) with a compound of formula (V):

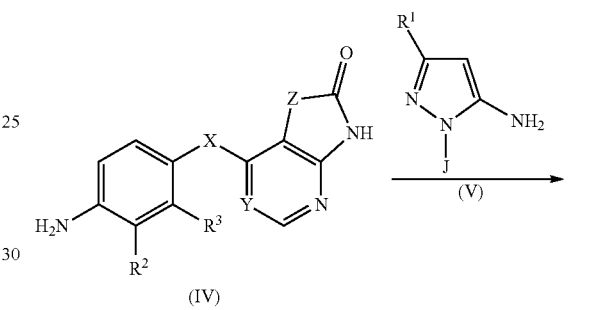

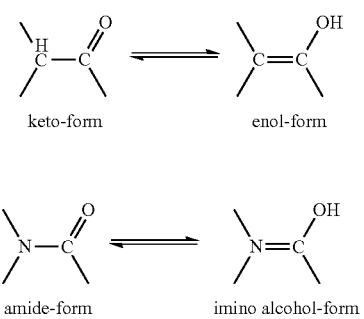

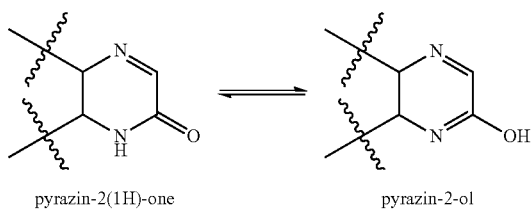

wherein $R^1$, $R^2$, $R^3$, J, X and Y are as defined for compounds of formula (I) in the presence of a coupling agent in an aprotic organic solvent such as dichloromethane, for example at RT.

Compounds of formula (IV) wherein Z represents $NR^4$ can be prepared as follows:

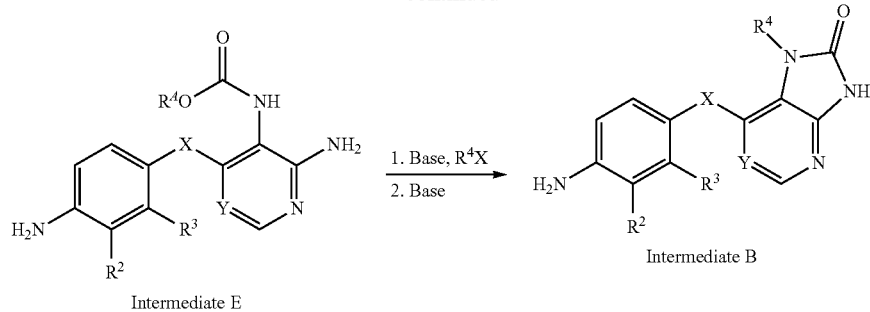

Intermediate E → Intermediate B

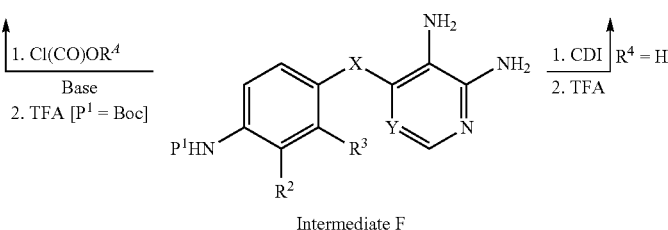

Intermediate F wherein $R^2$, $R^3$, $R^4$, X and Y are defined above for compounds of formula (I) and $R^4O(CO)Cl$ represents an alkyl or phenyl chloroformate (i.e. $R^4$ represents alkyl or phenyl). The N-acylation reaction can be conveniently conducted in the presence of an organic base, such as pyridine, and in an aprotic organic solvent such as THF and typically in a temperature range from 0° C. to RT.

Compounds of formula (IV), wherein Z represent $N=CR^{4a}$ can be prepared as follows:

wherein $R^2$, $R^3$, $R^{4a}$, X and Y are defined above for compounds of formula (I) and $P^1$ represents a protecting group such as Boc. The cyclisation step may be conveniently achieved by reaction with an alkyl 2-oxoalkanoate such as ethyl 2-oxoxacetate in a non polar, aprotic solvent such as toluene and suitably in the temperature range of RT to 100° C.

Intermediates F and G can be prepared by from Intermediate J;

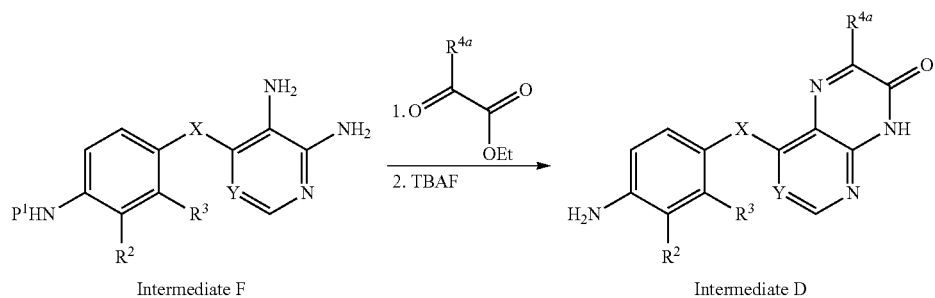

Intermediate F → Intermediate D

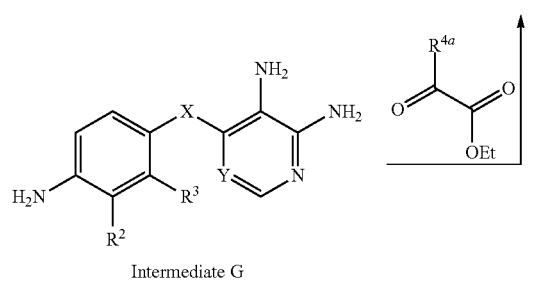

Intermediate G

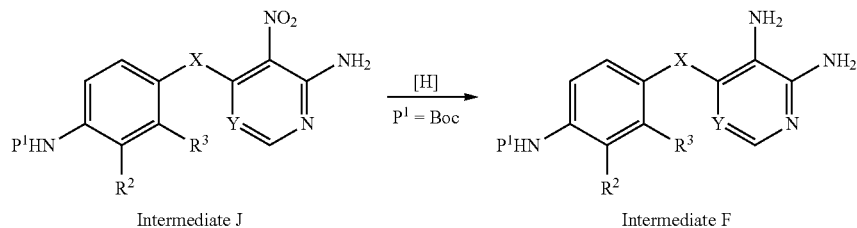

Intermediate J → Intermediate F

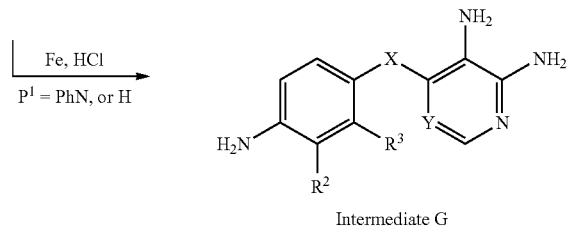

Intermediate G wherein $R^2$, $R^3$, X and Y are defined above for compounds of formula (I) and $P^1$ is either a nitrogen protecting group such as Boc or, where no protective group is required in subsequent steps, is absent (e.g. $P^1$=H), by catalytic hydrogenation or employing a dissolving metal reduction, such as iron in acetic acid or iron in hydrochloric acid acid.

Intermediates J can be prepared as shown below from commercially available starting materials and/or known compounds and/or from analogues that are readily prepared by those skilled in the art. Intermediates J are obtained by nucleopilic aromatic substitution reactions between a substituted arylamine as the nucleophile and an activated aryl halide, as the electrophile;

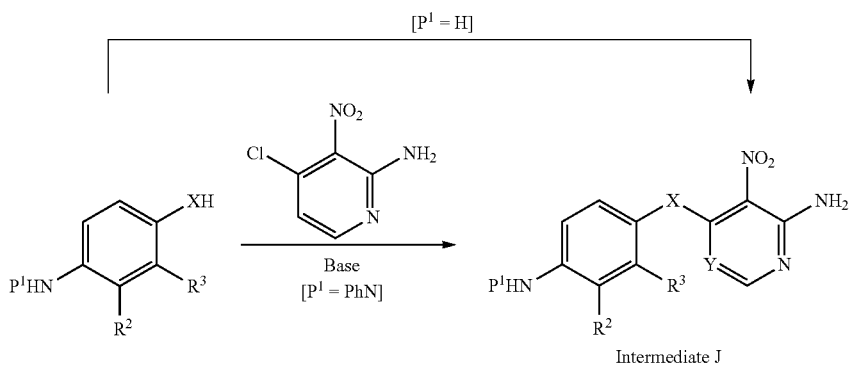

Intermediate J

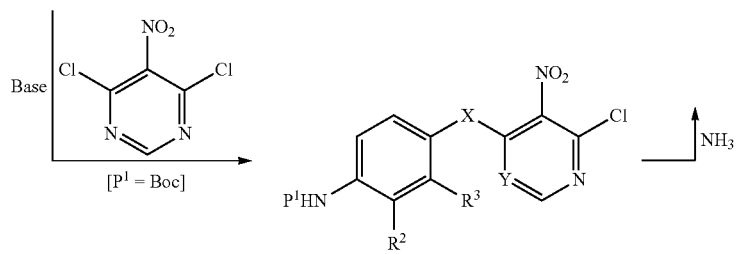

wherein $R^2$, $R^3$, X and Y are as defined above for compounds of formula (I) and $P^1$ represents as protecting group or hydrogen. The reaction is performed under basic condition at room temperature.

Certain compounds of formula (I) wherein $R^2$ and $R^3$ together with the phenyl ring to which they are attached represents quinoline and Z represents $NR^4$ and $R^1$, J, X and

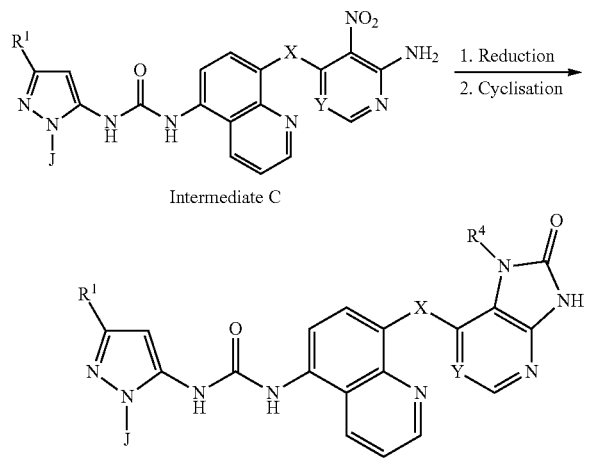

Intermediate C and Y are as defined above for compounds of formula (I) and wherein $R^4$=H can be prepared by reduction of a Intermediate C followed by cyclisation. The reduction step may be conveniently performed using a dissolving metal reduction method such as iron in acetic acid at an elevated temperature such as 50° C. and the cyclisation may be accomplished by reaction with an electrophilic carbonyl compound such as CDI in a polar aprotic solvent such as DMF, typically at ambient temperature such as 20° C.

Intermediate C can be prepared by reaction of Intermediate H:

wherein X and Y are as defined above for compounds of formula (I) with a compound of formula (V) wherein $R^1$ and J as are defined above for compounds of formula (I), in the presence of a coupling agent such as CDI and suitably in an aprotic solvent such as DCM and typically at ambient temperature such as 20° C.

Intermediates H can be prepared by reaction of a compound of formula (VI):

wherein X is as defined above for compounds of formula (I) with an activated halopyridine wherein Z is a halogen such as F or Cl in the presence of an inorganic base such potassium carbonate, in a polar aprotic solvent such as DMSO and at elevated temperature, such as 50-70° C.

Protecting groups may be required to protect chemically sensitive groups during one or more of the reactions described above, to ensure that the process is efficient. Thus if desired or necessary, intermediate compounds may be protected by the use of conventional protecting groups. Protecting groups and means for their removal are described in "Protective Groups in Organic Synthesis", by Theodora W. Greene and Peter G.M. Wuts, published by John Wiley & Sons Inc; 4$^{th}$ Rev Ed., 2006, ISBN-10: 0471697540.

In one aspect the compounds are useful in therapeutic treatment, for example in treatment (or prevention) of COPD and/or asthma.

Most of the low molecular weight chemical entities developed as therapeutic agents are optimised for delivery by oral administration. This strategy involves screening paradigms that select compounds which achieve their duration of action by an appropriate pharmacokinetic profile, coupled to an acceptable pharmacological potency. The pharmacokinetic profile is designed to ensure that a sufficiently high drug concentration is established and maintained between doses to provide sustained clinical benefit to the patient. An inevitable and undesirable consequence of this regimen is that all bodily tissues, but especially the liver and the gut, are likely to be exposed to therapeutically active, or even to supra-therapeutically active, concentrations of the drug, irrespective of whether these organs are adversely affected by the disease condition. As a result, the oral route of administration is frequently associated with adverse consequences which arise from the hazard of exposing "bystander" tissues to drug substance; potentially from both the intended pharmacological actions of the therapeutic agent, as well as its undesired side effects.

An alternative strategy to that outlined above is to treat the disease state by delivering the drug directly to the affected organ, that is, by topical therapy. Although this approach is not suitable for treating all chronic diseases, it has been extensively exploited in a range of inflammatory disorders, including those of the lung (asthma, chronic obstructive pulmonary disease (COPD), the skin (atopic dermatitis and psoriasis), the nose (allergic rhinitis), the eye (allergy) and for gastrointestinal diseases (ulcerative colitis).

The therapeutic efficacy of topical agents can be achieved by ensuring that the drug has a sustained duration of action and that it is retained in the relevant organ, thereby minimizing the risks of unwanted side effects from systemic exposure. This treatment paradigm is exemplified by the anti-cholinergic drug tiotropium (Spiriva), which is administered topically to the lung as a treatment for COPD and which has an exceptionally high affinity for its target receptor. This results in a very slow 'off rate' (dissociation rate) and consequently the compound displays a sustained duration of action (Disse, B. et al., *Life Sci* 1999, 64: 457-464).

In one aspect of the disclosure the compounds herein are particularly suitable for topical delivery, such as topical delivery to the lungs, in particular for the treatment of asthma and COPD.

In one aspect the compounds have a longer duration of action than BIRB 796.

In one embodiment the compounds are suitable for sensitizing patients to treatment with a corticosteroid.

The compounds herein may also be useful for the treatment of rheumatoid arthritis.

Further, the present invention provides a pharmaceutical composition comprising a compound according to the disclosure optionally in combination with one or more pharmaceutically acceptable diluents or carriers and use of the same in the methods of treatment and prophylaxis herein.

Diluents and carriers may include those suitable for parenteral, oral, topical, mucosal and rectal administration.

As stated above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence we provide according to the invention a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean aerodynamic diameter (MMAD) of 1-20 μm more typically 1-10 μm, such as 1-4 μm. The formulation will typically contain a topically acceptable diluent such as lactose, usually of large particle size e.g. a mass mean diameter (MMAD) of 100 μm or more. Example dry powder delivery systems include SPINHALER®, DISKHALER®, TURBOHALER®, DISKUS® and CLICKHALER®.

Formulations for use in the present invention also extend to solutions or suspensions for nebulisation.

Compounds according to the disclosure are intended to have therapeutic activity. In a further aspect, the present invention provides a compound of the disclosure for use as a medicament.

Thus in one aspect there is provided a pharmaceutical formulation for topical administration by inhalation comprising a population of particles of compound disclosed herein or a pharmaceutically acceptable salt thereof, including all stereoisomers, tautomers and isotopic derivatives, wherein the mass mean aerodynamic diameter (MMAD) of the population of particles is in the range 1 to 20 μm, for example with a mean particle size of the population of particles of compound is in the range 1 to 10 μm e.g. 1 to 4 μm.

Size reduction of particles may be achieved, for example, by conventional micronisation apparatus. MMAD may, for example, be measured by cascade impaction e.g. using an Andersen Impactor.

In one embodiment 50% of the particles of the population by number have a particle size within the specified range, for example 60, 70 or 80% t of the population have a particle size within the specified range, such as 90% of the population have a particle size within the specified range.

In one embodiment the formulation further comprises an excipient or carrier, for example the excipient is lactose, such as lactose monohydrate.

In one embodiment the mean particle size (MMAD) of the excipient is in the range 5 to 75 μm. In one embodiment 50, 60, 70, 80 or 90% of the excipient has a mean particle size (MMAD) within the range.

In one embodiment the formulation is a dry powder formulation.

In one embodiment the formulation is provided in a dry powder device, such as Diskus®, Rotahaler® or Turbohaler®.

In one embodiment the formulation is an aerosol formulation and for example comprises a carrier which is a liquefied propellant gas, in particular selected from HFA 134a (1,1,1,2-tetrafluoroethane), HFA 227 (hepatfluropropane) and mixtures thereof in which particles of compound are suspended.

In one embodiment the formulation is provided in a metered dose inhaler.

In one embodiment a device according to the present disclosure is overwrapped to minimize moisture ingression.

In one embodiment there is provided a formulation or a device as defined herein for use in treatment, for example as particularised below.

Compounds according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, chronic bronchitis and COPD.

Compounds of the disclosure may also re-sensitise the patient's condition to treatment with a corticosteroid, when the patient's condition has become refractory to the same.

Compounds according to the disclosure are also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

Compounds of the disclosure are also expected to be useful in the treatment of pancreatitis and cachexia.

Compounds of the disclosure may be useful in the treatment of proliferative conditions in general, including cancers, for example compounds of the disclosure may be useful in the inhibition of the growth and metastasis of tumours including non-small cell lung carcinoma, breast carcinoma, gastric carcinoma, colorectal carcinomas and malignant melanoma.

Compounds of the disclosure are believed to be useful as anti-viral agents, for example in the treatment of conditions including influenza infection and/or rhinovirus infection. They may also be useful in the treatment of respiratory syncytial virus (RSV)). In particular the compounds of the present disclosure may be suitable for use in the treatment or prevention of viral infection e.g. infection by influenza virus and/or rhinovirus (e.g. HRV) and/or RSV and in particular may be capable of reducing viral load and/or ameliorating symptoms after infection, in particular viral mediated or viral exacerbated respiratory disease/disorder or respiratory infections.

Compounds of the disclosure may also be useful in treatment of inflammatory diseases of the gastrointestinal tract including bowel diseases such as Crohn's disease, collagenous colitis, diverticulitis, lymphocytic colitis, ischemic colitis, diversion colitis, Behcet's syndrome, indeterminate colitis and eosinophilic esophagitis as well as ulcerative colitis which is above mentioned.

Compounds of the disclosure may also be useful in treatment of inflammatory diseases of the eye including anterior uveitis, posterior uveitis, panuveitis, keratitis, corneal ulcer, corneal edema, sterile corneal infiltrates, anterior scleritis, episcleritis, blepharitis, and post-operative (or post-surgical) ocular inflammation resulting from procedures such as photorefractive keratectomy, cataract removal surgery, intraocular lens implantation, laser-assisted in situ keratomileusis ("LASIK"), conductive keratoplasty, radial keratotomy, dry eye, macular degeneration, macular edema, diabetic retinopathy, wet age-related macular degeneration, dry age-related macular degeneration and diabetic retinopathy as well as conjunctivitis (including allergic conjunctivitis, vernal keratoconjunctivitis and atopic keratoconjunctivitis).

Compounds of the disclosure may also be useful in the treatment of inflammation associated with bacterial or viral infection of the eye. Specifically, compounds of the disclosure may be useful in the treatment of inflammation and infection of the eye associated with viral infection, such as infection by cytomegalovirus, adenovirus and herpes virus.

Compounds of the disclosure may be useful in the treatment of inflammatory diseases of the skin, such as psoriasis, allergic dermatitis and contact dermatitis which are above mentioned.

Compounds of the disclosure may be useful in the treatment of inflammatory diseases of joints, especially synovial joints, such as arthritis including rheumatoid arthritis or osteoarthritis which are above mentioned.

Thus, in a further aspect, the present invention provides a compound as described herein for use in the treatment of the above mentioned conditions.

In a further aspect, the present invention provides use of a compound as described herein for the manufacture of a medicament for the treatment of the above mentioned conditions.

In a further aspect, the present invention provides a method of treatment of the above mentioned conditions which comprises administering to a subject an effective amount of a compound of the disclosure or a pharmaceutical composition thereof.

As used herein, the word "treatment" is intended to embrace prophylaxis as well as therapeutic treatment.

A compound of the disclosure will suitably be administered to a subject, typically a human subject, in a therapeutically effective amount. A therapeutically effective amount may be determined by a skilled person bearing in mind the type of condition to be treated, the severity of the condition, the weight and condition of the subject, and the potency of the compound inter alia.

An effective amount will be an amount effective to cause reduction in symptoms of respiratory disorder for example a chronic respiratory disorder such as asthma or COPD or a viral infection, for example an amount which causes a reduction in viral load, and may be determined by a skilled person by reference to the severity of the condition in the subject. Typically an amount of 0.1 to 10 e.g. 1 to 5 µg/kg or a dose of 7 to 700 e.g. 70 to 350 µg per day will be suitable.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline).

EXPERIMENTAL SECTION

Abbreviations used herein are defined below (Table 1). Any abbreviations not defined are intended to convey their generally accepted meaning.

TABLE 1

| Abbreviations | |
|---|---|
| AcOH | glacial acetic acid |
| aq | aqueous |
| Ac | acetyl |
| ATP | adenosine-5'-triphosphate |
| BALF | bronchoalveolae lavage fluid |
| Boc | tert-butoxycarbonyl |
| br | broad |
| BSA | bovine serum albumin |
| CatCart ® | catalytic cartridge |
| CDI | 1,1-carbonyl-diimidazole |
| COPD | chronic obstructive pulmonary disease |
| d | doublet |
| DCM | dichloromethane |
| DIAD | diisopropylazadicarboxylate |
| DIBAL-H | diisobutylaluminium hydride |
| DIPEA | N,N-diisopropylethylamine |
| DMF | N,N-dimethylformamide |
| DMSO | dimethyl sulfoxide |
| d-U937 cells | PMA differentiated U-937 cells |
| (ES$^+$) | electrospray ionization, positive mode |
| Et | ethyl |
| EtOAc | ethyl acetate |
| FCS | foetal calf serum |
| FRET | fluorescence resonance energy transfer |
| HOBt | 1-hydroxybenzotriazole |
| hr | hour(s) |
| HRP | horseradish peroxidise |
| HRV | human rhinovirus |
| ICAM-1 | inter-cellular adhesion molecule 1 |
| JNK | c-Jun N-terminal kinase |
| LPS | lipopolysaccharide |
| (M + H)$^+$ | protonated molecular ion |
| MAPK | mitogen protein activated protein kinase |
| MAPKAP-K2 | mitogen-activated protein kinase-activated protein kinase-2 |
| Me | methyl |
| MeCN | acetonitrile |
| MeOH | methanol |
| MHz | megahertz |
| MMAD | mass median aerodynamic diameter |
| min | minute(s) |
| MTT | 3-(4,5-dimethylthiazol-2-yl)-2,5-diphenyltetrazolium bromide |
| m/z: | mass-to-charge ratio |
| NMM | N-methylmorpholine; (4-methylmorpholine) |
| NMP | 1-methylpyrrolidin-2-one (N-methyl-2-pyrrolidone) |
| NMR | nuclear magnetic resonance (spectroscopy) |

TABLE 1-continued

| Abbreviations | |
|---|---|
| Ph | phenyl |
| PBS | phosphate buffered saline |
| PMA | phorbol myristate acetate |
| PPh$_3$ | triphenylphosphine |
| q | quartet |
| RT | room temperature |
| RP HPLC | reverse phase high performance liquid chromatography |
| RSV | Respiratory syncytical virus |
| s | singlet |
| sat | saturated |
| SCX | solid supported cation exchange (resin) |
| SDS | sodium dodecyl sulphate |
| S$_N$Ar | nucleophilic aromatic substitution |
| t | triplet |
| TBAF | tetrabutylammonium fluoride |
| TBDMS-Cl | tert-butyldimethylchlorosilane |
| TCID$_{50}$ | 50% tissue culture infectious dose |
| TFA | trifluoroacetic acid |
| THF | tetrahydrofuran |
| TIPS-Cl | chlorotriisopropylsilane |
| TMB | 3,3',5,5'-tetramethylbenzidine |
| TNFα | tumor necrosis factor alpha |
| XantPhos | 4,5-bis(diphenylphosphino)-9,9-dimethylxanthene |

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were preformed on a Thales H-cube flow reactor under the conditions stated.

Column chromatography was performed on pre-packed silica (230-400 mesh, 40-63 µm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Preparative Reverse Phase High Performance Liquid Chromatography: Agilent Scalar column C18, 5 µm (21.2× 50 mm), flow rate 28 mL min$^{-1}$ eluting with a $H_2O$-MeCN gradient containing 0.1% v/v formic acid over 10 min using UV detection at 215 and 254 nm. Gradient information: 0.0-0.5 min; 95% $H_2O$-5% MeCN; 0.5-7.0 min; ramped from 95% $H_2O$-5% MeCN to 5% $H_2O$-95% MeCN; 7.0-7.9 min; held at 5% $H_2O$-95% MeCN; 7.9-8.0 min; returned to 95% $H_2O$-5% MeCN; 8.0-10.0 min; held at 95% $H_2O$-5% MeCN.

Analytical Methods

Reverse Phase High Performance Liquid Chromatography: Method 1): Agilent Scalar column C18, 5 µm (4.6×50 mm) or Waters XBridge C18, 5 µm (4.6×50 mm) flow rate 2.5 mL min$^{-1}$ eluting with a $H_2O$-MeCN gradient containing either 0.1% v/v formic acid (Method 1 acidic) or $NH_3$ (Method 1 basic) over 7 min employing UV detection at 215 and 254 nm. Gradient information: 0.0-0.1 min, 95% $H_2O$-5% MeCN; 0.1-5.0 min, ramped from 95% $H_2O$-5% MeCN to 5% $H_2O$-95% MeCN; 5.0-5.5 min, held at 5% $H_2O$-95% MeCN; 5.5-5.6 min, held at 5% $H_2O$-95% MeCN, flow rate increased to 3.5 mL min$^{-1}$; 5.6-6.6 min, held at 5% $H_2O$-95% MeCN, flow rate 3.5 mL min-; 6.6-6.75 min, returned to 95% $H_2O$-5% MeCN, flow rate 3.5 mL min$^{-1}$; 6.75-6.9 min, held at 95% $H_2O$-5% MeCN, flow rate 3.5 mL·min$^{-1}$; 6.9-7.0 min, held at 95% $H_2O$-5% MeCN, flow rate reduced to 2.5 mL min$^{-1}$.

Reverse Phase High Performance Liquid Chromatography: Method 2: Agilent Extend C18 column, 1.8 μm (4.6×30 mm) at 40° C.; flow rate 2.5-4.5 mL min$^{-1}$ eluting with a H$_2$O-MeCN gradient containing 0.1% v/v formic acid over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^-$; 3.01 3.50 min, held at 5% H$_2$O-95% MeCN; 3.50-3.60 min, returned to 95% H$_2$O-5% MeCN, flow rate reduced to 3.50 mL min$^-$; 3.60-3.90 min, held at 95% H$_2$O-5% MeCN; 3.90-4.00 min, held at 95% H$_2$O-5% MeCN, flow rate reduced to 2.5 mL min$^-$.

$^1$H NMR Spectroscopy: $^1$H NMR spectra were acquired on a Bruker Avance III spectrometer at 400 MHz using residual undeuterated solvent as reference.

Generic Routes to Compound Examples.

1. Compound Examples that Contain a 5-6 Ring System (Z=NR$^4$)

Compounds examples that comprise of a naphthalene core (R$^2$ and R$^3$ and the carbon atoms to which they are attached comprise a fused phenyl ring) or dichlorophenyl core (R$^2$ and R$^3$=Cl) were prepared by a final coupling reaction, to generate the central urea, between compounds represented by Intermediate A with compounds represented by Intermediate B.

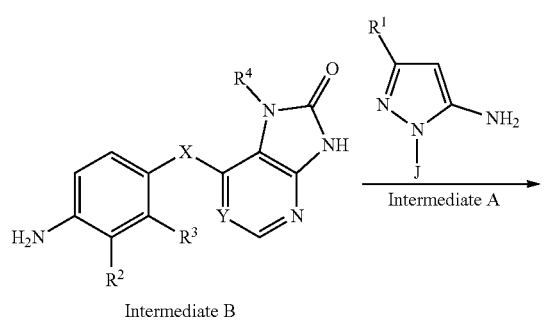

Intermediate B

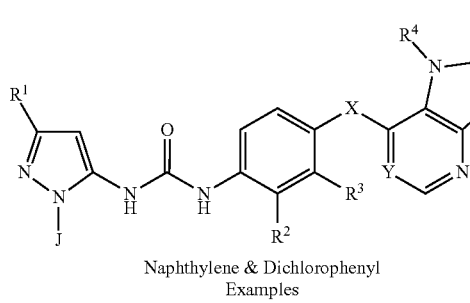

Naphthylene & Dichlorophenyl Examples

For quinoline analogues, (R$^2$ and R$^3$ and the carbon atoms to which they are attached comprise a fused pyridine ring) compound examples were prepared by the formation of the terminal imidazopyridinone ring system (Y=CH) from compounds represented by Intermediate C by reduction of the nitroarene, followed by cyclisation of the resulting diamine.

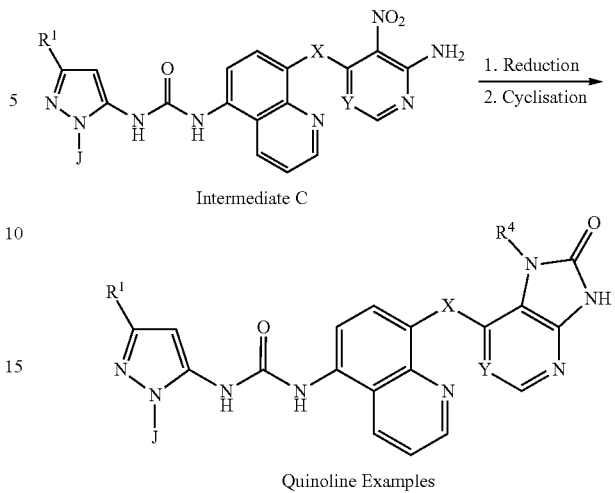

Intermediate C

Quinoline Examples

2. Compound Examples that Contain a 6-6 Ring System (Z=N=CR$^4$)

Compounds examples that comprise of a naphthalene core (R$^2$ and R$^3$ and the carbon atoms to which they are attached comprise a fused phenyl ring) or a dichlorophenyl core (R$^2$ and R$^3$ =Cl) were prepared by a final coupling reaction, to generate the central urea, between compounds represented by Intermediate A with compounds represented by Intermediate D.

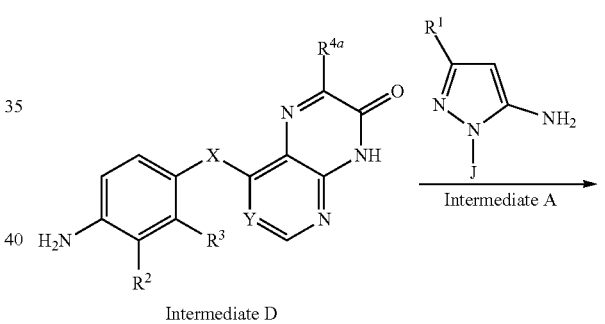

Intermediate D

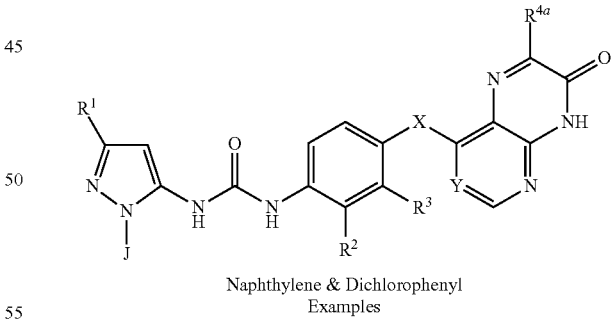

Naphthylene & Dichlorophenyl Examples

3. The Preparation of Generic Compound Intermediates

Compounds represented by Intermediate B (Z=NR$^4$) were obtained from compounds represented by Intermediate E by chemoselective N-alkylation of the carbamate nitrogen followed by base induced cyclisation to generate the imidazolone ring system. Examples of Intermediate B that contain an unsubstituted imidazolone ring (R$^4$=H), were prepared using an alternative method, from compounds represented by Intermediate F, by cyclisation of the aryl 1,2-diamine with an electrophilic carbonyl equivalent such as CDI.

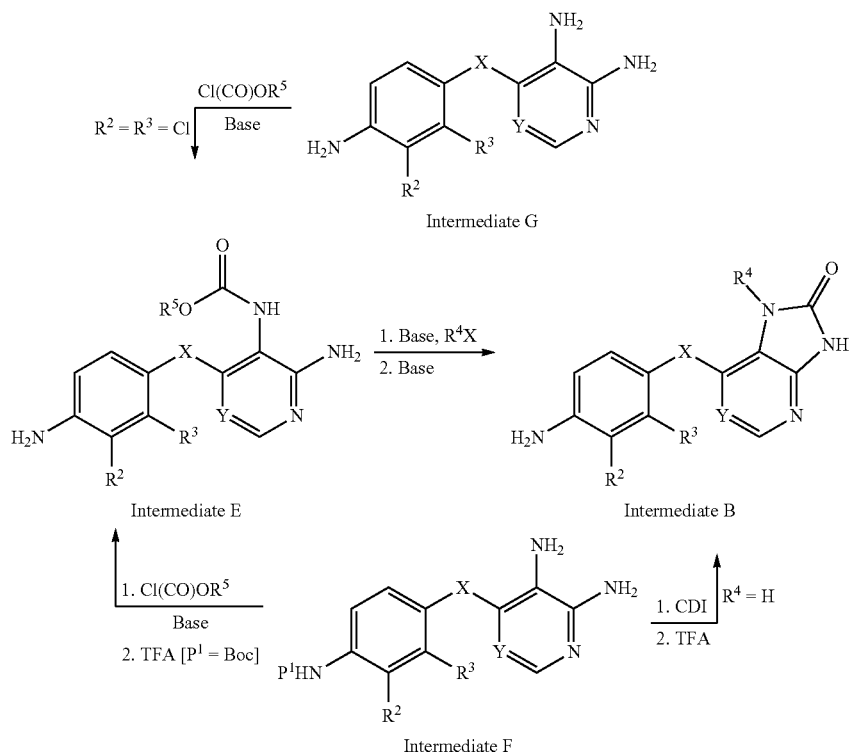

Compounds represented by Intermediate F were transformed into compounds represented by Intermediate E by selective acylation with an alkyl chloroformate, followed by removal of the protective group [P$^1$]. An example of a suitable protective group for this series of transformations is a tert-butyloxycarbonyl (Boc) group which may be removed by acidolysis For those cases in which Intermediate B comprises of an electron poor aniline (for example when R$^2$=R$^3$=Cl), the requisite precursors represented by Intermediate E were prepared by the direct regioselctive acylation of a diaryl triamine represented by Intermediate G.

Compounds represented by Intermediate C are accessible from precursors represented by Intermediate H by a urea coupling reaction with an compound represented by Intermediate A.

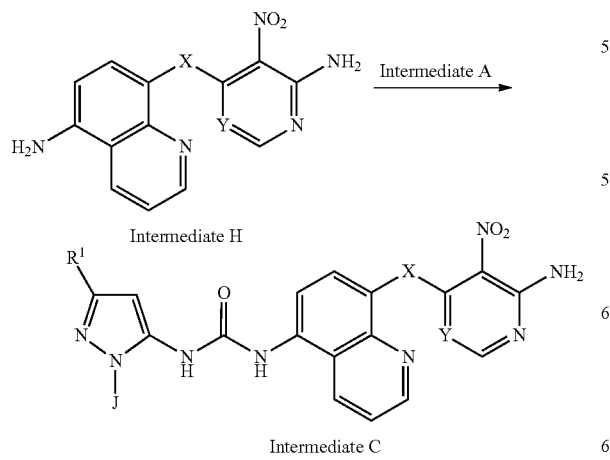

Structures represented by Intermediate D, required for the preparation of compound examples of the disclosure that incorporate a pyridopyrazinone (Y=CH) or a pteridinone (Y=N) ring system were derived from compounds represented by Intermediate F by condensation with an α-carbonyl ester, followed by deprotection of the anilino nitrogen. For example, in those cases wherein R$^{4a}$=Me the α-carbonyl ester is a pyruvate ester such as ethyl pyruvate. Alternatively, those examples of Intermediate D that comprise of an electron

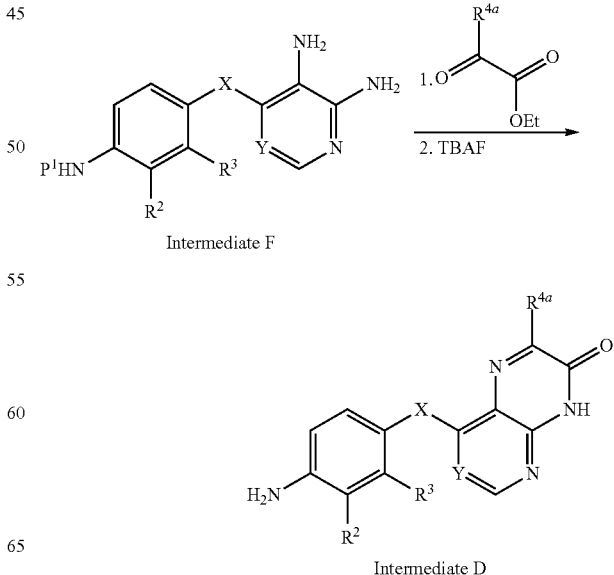

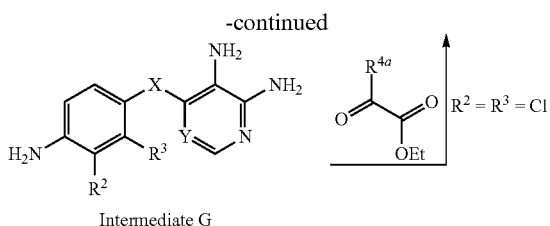

Intermediate G poor aniline (for example when $R^2=R^3=Cl$), and for those examples of Intermediate D for which X is represented by $OCH_2$ may be prepared by the condensation of an α-carbonyl ester with compounds represented by Intermediate G in which selective protection/deprotection of the anilino nitrogen is not required. For example, in those cases wherein $R^{4a}=H$ the α-carbonyl ester is a glyoxalate ester such as ethyl glyoxalate. An example of a suitable protective group for this series of transformations is the Boc group which may be removed by exposure to fluoride, for example by treatment with TBAF.

Compounds represented by Intermediate F and Intermediate G were obtained by reduction of nitroarenes represented by Intermediate J. In the former case a nitrogen protective group [$P^1$] is selected that is orthogonal, that is, one which is stable and not removed under the conditions used to affect the reduction step. An example of a reductive process that is suitable for this transformation is catalytic hydrogenation and an example of a suitable protective group which is orthogonal to these conditions and may be conveniently selected is a Boc group. In the second instance it may be advantageous to employ a protective group [$P^1$] that is labile under the conditions used to reduce the nitroarene. An example of a

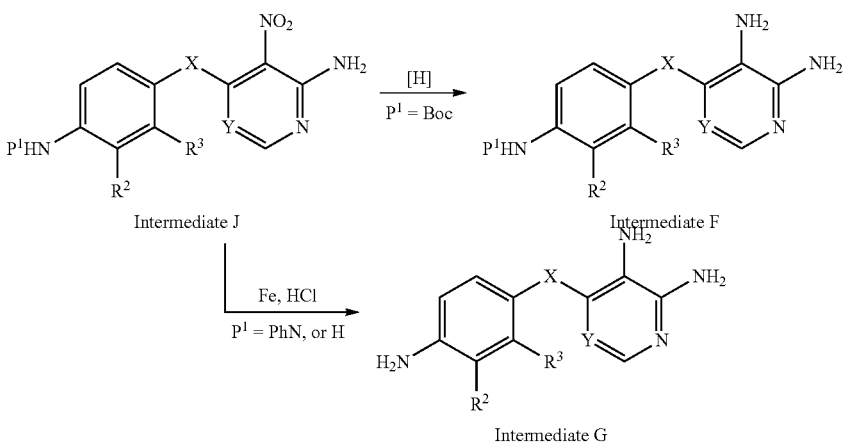

reductive procedure that is suitable for this conversion is a dissolving metal reduction, such as iron in hydrochloric acid and an example of a protective group which is labile and may be conveniently selected for this process is an aryldiazene such as a phenyl diazene. [i.e. $P^1=PhN=$]. In some instances (for example when $R^2=R^3=Cl$) no protective group may be required [i.e. $P^1=H$]

Compounds represented by Intermediate J were assembled from suitably protected aryl amine derivatives by $S_NAr$ reactions with activated halopyridines and halopyrimidines under basic conditions. These starting materials are either commercially available or are known compounds or may be prepared from readily available precursors by standard procedures, known in the art. In some instances, for example, where the aniline component is electron deficient (for example when $R^2=R^3=Cl$) no nitrogen protective group may be required [i.e. $P^1=H$] to maintain chemoselectivity during the $S_NAr$ coupling step.

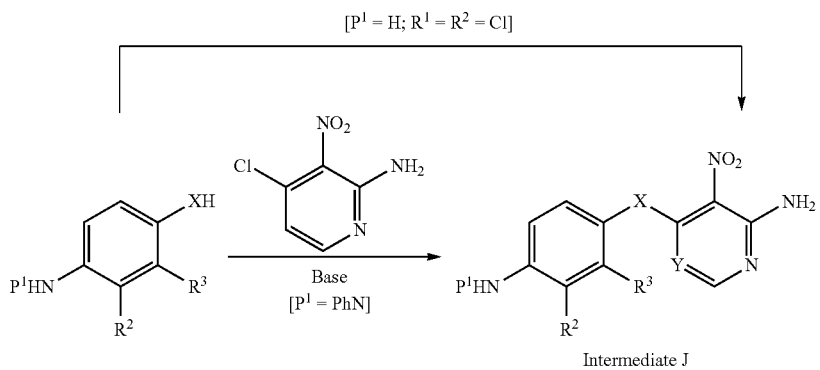

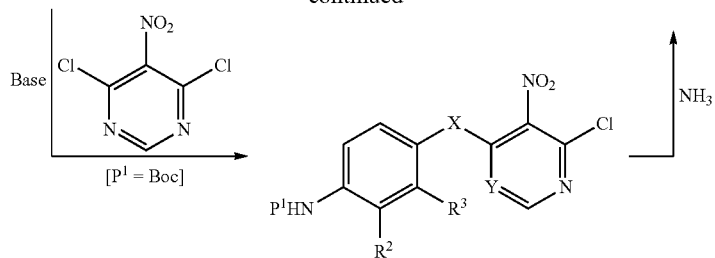

Compounds represented by Intermediates H were similarly obtained by SNAr condensation of 4-chloro-3-nitropyridin-2-amine with an aminoquinoline nucleophile under basic conditions.

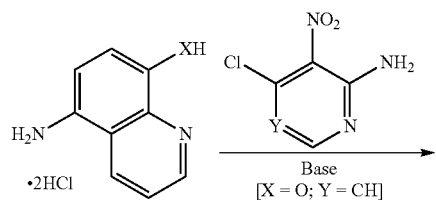

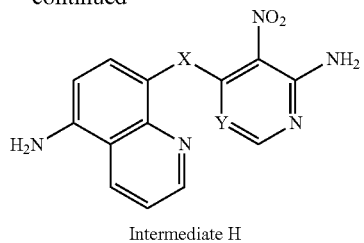

Intermediate H

INTERMEDIATES TO COMPOUND EXAMPLES

The following Intermediates used to prepare compound examples of the disclosure have been previously described or are available from commercial sources and were either purchased or prepared using the procedures in the references cited below (Table 2).

TABLE 2

Commercially Available and Previously Described Intermediates.

| Intermediate | Structure | Name, LCMS Data and Reference |
|---|---|---|
| A1 | (structure) | 3-tert-butyl-1-p-tolyl-1H-pyrazol-5-amine. $R^t$ 2.46 min (Method 1 basic); m/z 230 $(M + H)^+$, $(ES^+)$. Cirillo, P. F. et al., WO 2000/43384, 27 Jul. 2000. |
| A2 | (structure) | 3-tert-butyl-1-(4-methoxyphenyl)-1H-pyrazol-5-amine. $R^t$ 1.32 min (Method 2); m/z 246 $(M + H)^+$, $(ES^+)$. Mathias, J. P. et al., US 2006/0035922, 10 Aug. 2005. |

TABLE 2-continued

Commercially Available and Previously Described Intermediates.

| Intermediate | Structure | Name, LCMS Data and Reference |
|---|---|---|
| A3 | 3-tert-butyl-1-(4-OTBDMS-phenyl)-pyrazol-5-amine structure | 3-tert-butyl-1-(4-(tert-butyldimethylsilyloxy)phenyl)-1H-pyrazol-5-amine.<br>$R^t$ 2.80 min (Method 2); m/z 346 (M + H)$^+$, (ES$^+$).<br>Mathias, J. P. et al., US 2006/0035922, 10 Aug. 2005. |
| A4 | 3-tert-butyl-1-(4-SMe-phenyl)-pyrazol-5-amine structure | 3-tert-butyl-1-(4-(methylthio)phenyl)-1H-pyrazol-5-amine.<br>$R^t$ 1.70 min (Method 2); m/z 262 (M + H)$^+$, (ES$^+$).<br>Mathias, J. P. et al., US 2006/0035922, 10 Aug. 2005. |
| A5 | 3-tert-butyl-1-(4-SO2Me-phenyl)-pyrazol-5-amine structure | 3-tert-butyl-1-(4-(methylsulfonyl)phenyl)-1H-pyrazol-5-amine.<br>$R^t$ 3.65 min (Method 1 basic); m/z 294 (M + H)$^+$, (ES$^+$).<br>Springer, C. J. et al., WO 2009/077766, 25 Jun. 2009. |
| A6 | 3-tert-butyl-1-(4-chlorophenyl)-pyrazol-5-amine structure | 3-tert-butyl-1-(4-chlorophenyl)-1H-pyrazol-5-amine.<br>$R^t$ 1.92 min (Method 2); m/z 250/252 (M + H)$^+$, (ES$^+$).<br>Abraham, S. et al., WO 2009/117080, 24 Sep. 2009. |
| A7 | 3-tert-butyl-1-(3,4-dichlorophenyl)-pyrazol-5-amine structure | 3-tert-butyl-1-(3,4-dichlorophenyl)-1H-pyrazol-5-amine.<br>$R^t$ 2.51 min (Method 2); m/z 284/286 (M + H)$^+$, (ES$^+$).<br>Li, S. et al., WO 2008/125014, 13 Oct. 2008. |

TABLE 2-continued

Commercially Available and Previously Described Intermediates.

| Intermediate | Structure | Name, LCMS Data and Reference |
|---|---|---|
| A8 | 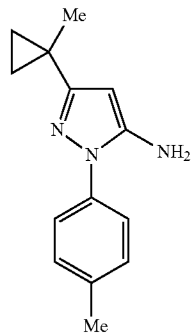 [SMILES: Cc1ccc(-n2nc(C3(C)CC3)cc2N)cc1] | 3-(1-methylcyclopropyl)-1-(p-tolyl)-1H-pyrazol-5-amine.<br>$R^r$ 3.72 min (Method 1 basic); m/z 228 (M + H)$^+$, (ES$^+$).<br>Bastian, J. A. et al., WO 2007/053394, 10 May 2007. |
| A9 | 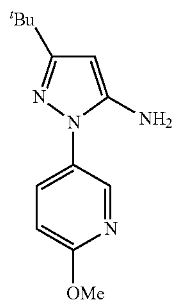 [SMILES: COc1ccc(-n2nc(C(C)(C)C)cc2N)cn1] | 3-tert-butyl-1-(6-methoxypyridin-3-yl)-1H-pyrazol-5-amine.<br>$R^r$ 3.85 min (Method 1 basic); m/z 247 (M + H)$^+$, (ES$^+$).<br>Betageri, R., et al., WO 2000/55139, 21 Sep. 2000. |
| A10 | 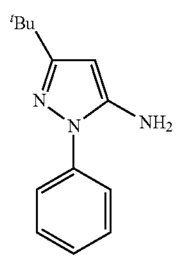 [SMILES: CC(C)(C)c1cc(N)n(-c2ccccc2)n1] | 3-(tert-butyl)-1-phenyl-1H-pyrazol-5-amine<br>Compound is commercially available. |
| A11 | 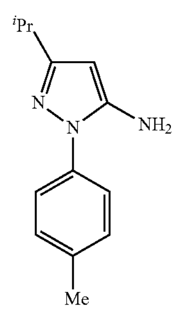 [SMILES: Cc1ccc(-n2nc(C(C)C)cc2N)cc1] | 3-isopropyl-1-p-tolyl-1H-pyrazol-5-amine.<br>$R^r$ 1.32 min (Method 2); m/z 216 (M + H)$^+$, (ES$^+$).<br>Ito, K. et al., WO 2010/067130, 17 Jun. 2010. |
| B1 | 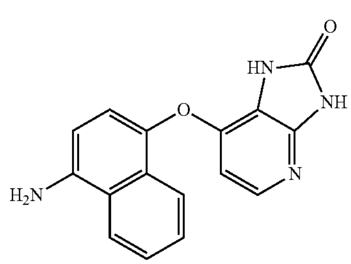 [SMILES: Nc1ccc(Oc2ccnc3[nH]c(=O)[nH]c23)c2ccccc12] | 7-((4-aminonaphthalen-1-yl)oxy)-1H-imidazo[4,5-b]pyridin-2(3H)-one.<br>$R^r$ 1.18 min (Method 2); m/z 293 (M + H)$^+$ (ES$^+$).<br>Niculescu-Duvaz, D., et al WO 2006/043090, 27 Apr. 2006 |

TABLE 2-continued

Commercially Available and Previously Described Intermediates.

| Intermediate | Structure | Name, LCMS Data and Reference |
|---|---|---|
| B2 | 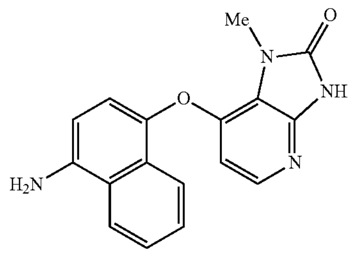 [SMILES: Cn1c(=O)[nH]c2nccc(Oc3ccc(N)c4ccccc34)c21] | 7-((4-aminonaphthalen-1-yl)oxy)-1-methyl-1H-imidazo[4,5-b]pyridin-2(3H)-one<br>$R^t$ 1.39 min (Method 2); m/z 307 (M + H)$^+$ (ES$^+$).<br>Menard et al., *J. Med. Chem.*, 2009, 52(13), 2881-3991. |
| D1 | 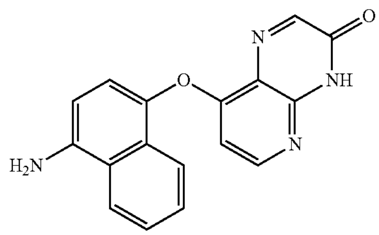 [SMILES: Nc1ccc(Oc2ccnc3[nH]c(=O)cnc23)c2ccccc12] | 8-((4-aminonaphthalen-1-yl)oxy)pyrido[2,3-b]pyrazin-3(4H)-one<br>$R^t$ 2.05 min (Method 1 basic); m/z 305 (M + H)$^+$ (ES$^+$).<br>Zambon, Alfonso; et al., *J. Med. Chem.*, 2010, 53(15), 5639-5655. |
| E1 | 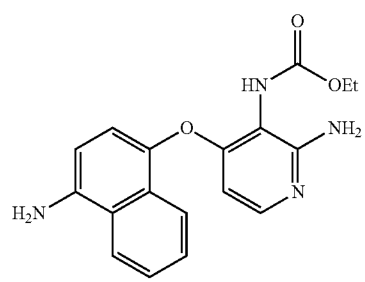 [SMILES: CCOC(=O)Nc1c(Oc2ccc(N)c3ccccc23)ccnc1N] | ethyl (2-amino-4-((4-aminonaphthalen-1-yl)oxy)pyridin-3-yl)carbamate<br>$R^t$ 1.05 min (Method 2); m/z 339 (M + H)$^+$ (ES$^+$).<br>Menard et al., *J. Med. Chem.*, 2009 52(13), 2881-3991. |

Additional intermediates that were required for the synthesis of compound examples of the disclosure were prepared as described below.

Intermediate A12

3-(tert-Butyl)-1-(4-(((triisopropylsilyl)oxy)methyl)phenyl)-1H-pyrazol-5-amine

To a solution of (4-(5-amino-3-tert-butyl-1H-pyrazol-1-yl)phenyl)methanol (Ito, K. et al., WO 2010/067131) (8.50 g, 35.0 mmol) and 1H-imidazole (2.71 g, 39.8 mmol) in dry THF (100 mL) under N$_2$ was added chlorotriisopropylsilane (8.16 mL, 38.1 mmol) and the reaction mixture maintained at RT for 5 days. The resulting mixture was evaporated in vacuo and the residue was partitioned between EtOAc (250 mL) and water (100 mL). The organic layer was separated and was washed with (water (100 mL) and brine (80 mL) and then dried and evaporated in vacuo to afford the title compound, Intermediate A12 as a dark red solid (14.6 g, 97%); $R^t$ 3.26 min (Method 2); m/z 402 (M+H)$^+$, (ES$^+$).

Intermediate A13

1-(4-(5-Amino-3-tert-butyl-1H-pyrazol-1-yl)phenyl)-N-methyl methanesulfonamide

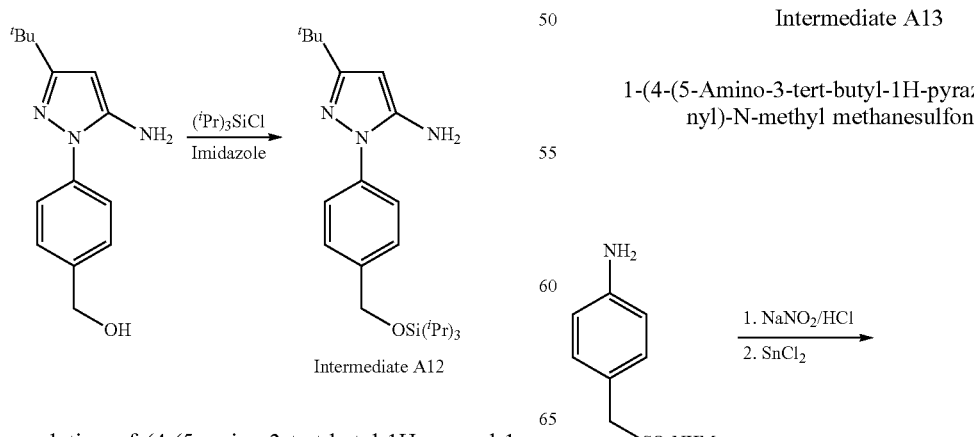

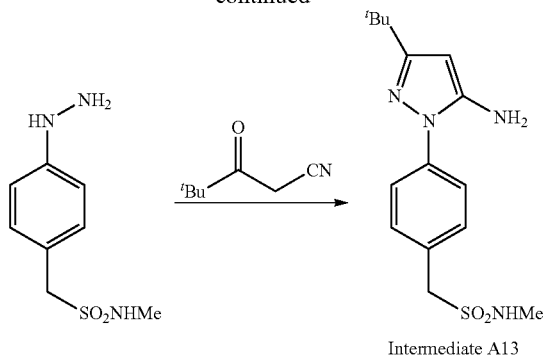

To a suspension of 1-(4-aminophenyl)-N-methylmethanesulfonamide (500 mg, 2.50 mmol) in hydrochloric acid (6 M, 10 mL) at 0° C. was added a solution of sodium nitrite (181 mg, 2.62 mmol) in water (3.0 mL) over 5 min. The reaction mixture was maintained at 0° C. for 2.5 hr, was treated with tin(II) chloride (1.33 g, 6.99 mmol) in hydrochloric acid (6M, 15 mL) and was then warmed to RT for 64 hr. The resulting mixture was basified to pH 12 with aq NaOH (6.0 M) and was extracted with EtOAc (2×100 mL). The combined organic extracts were washed with water and then dried and evaporated in vacuo to give a residue that was suspended in ethanol (10 mL) and treated with 4,4-dimethyl-3-oxopentanenitrile (160 mg, 1.3 mmol) and conc hydrochloric acid (12 M, 106 μL, 1.27 mmol). The resulting mixture was heated at reflux for 5 hr and after a further 23 hr at RT was evaporated in vacuo, to remove the ethanol. The resulting aq mixture was basified with aq NaOH (2.0 M) and was then extracted with DCM (2×30 mL). The combined organic extracts were dried and evaporated in vacuo to afford the title compound, Intermediate A13, as an orange solid (146 mg, 85% purity, 15%); R$^t$ 1.34 min (Method 2); m/z 323 (M+H)$^+$, (ES$^+$). This material was used in subsequent steps without further purification.

Intermediate A14

3-tert-Butyl-1-(4-methylthiophen-2-yl)-1H-pyrazol-5-amine

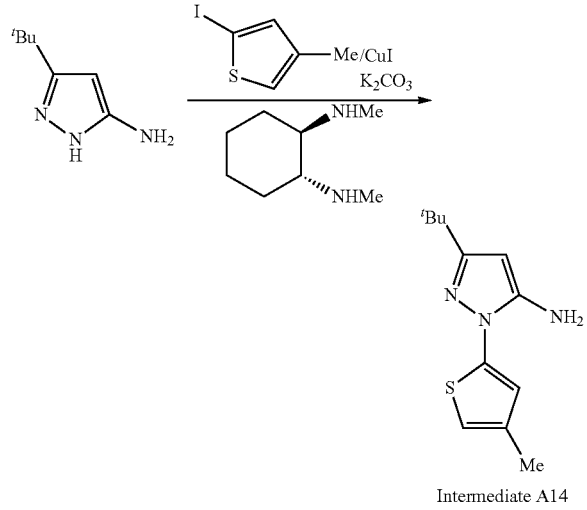

To a solution of 2-iodo-4-methylthiophene (WO 2008/121666) (1.00 g, 4.50 mmol) in anhydrous toluene (15.0 mL) was added 3-tert-butyl-1H-pyrazol-5-amine (683 mg, 4.91 mmol) followed by (1R,2R)—N$^1$,N$^2$-dimethylcyclohexane-1,2-diamine (140 μL, 0.89 mmol) and potassium carbonate (1.30 g, 9.37 mmol). The mixture was purged with N$_2$, copper(I) iodide (42 mg, 0.22 mmol) was added and the reaction mixture was heated at reflux under N$_2$ for 16 hr during which time most of the solvent was lost. The resulting mixture was partitioned between ethyl acetate (150 mL) and water (150 mL) and the organic layer was separated and extracted with aq. citric acid solution (10% w/v, 150 mL) followed by brine (50 mL), and then dried and evaporated in vacuo. The residue was purified by flash column chromatography (SiO$_2$, 120 g, DCM, isocratic elution) to afford the title compound, Intermediate A14, as a brown solid (340 mg, 32%); R$^t$ 1.94 min (Method 2); m/z 236 (M+H)$^+$ (ES$^+$).

Intermediate A15

3-Cyclopropyl-1-p-tolyl-1H-pyrazol-5-amine

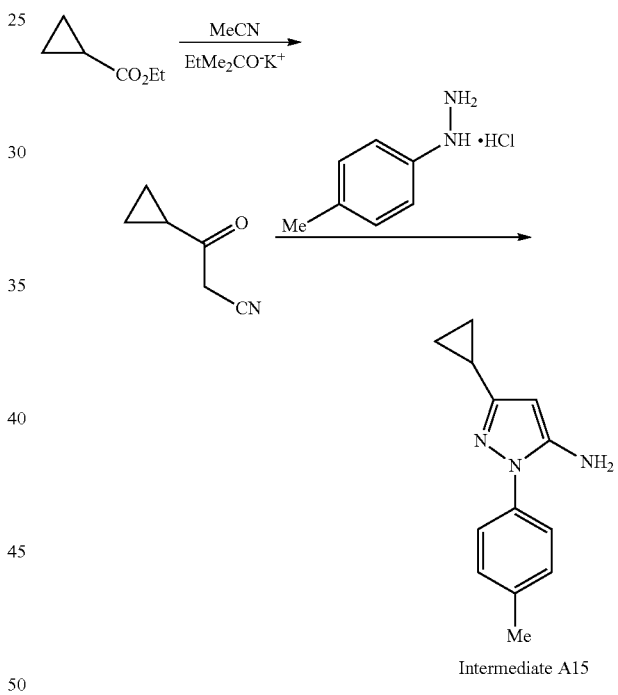

To a solution of acetonitrile (500 μL, 390 mg, 9.6 mmol) in THF (30 mL) at RT was added a solution of potassium 2-methylbutan-2-olate in toluene (1.7 M, 17.0 mL, 29.0 mmol) followed by the dropwise addition of ethyl cyclopropanecarboxylate (4.56 mL, 4.37 g, 38.0 mmol) and the reaction mixture maintained at RT for 16 hr. The resulting mixture was concentrated in vacuo to a volume of ~15 mL and was then diluted with EtOH (20 mL) and p-tolylhydrazine hydrochloride (1.52 g, 9.57 mmol) was added. The mixture was acidified to pH 1 by the addition of conc hydrochloric acid and the resulting heterogeneous mixture was heated to 70° C. for 2 hr, then cooled to RT and concentrated in vacuo to a volume of ~20 mL. The mixture was diluted with water (30 mL) and was adjusted to pH 12 by the addition of 2M aq NaOH and extracted with diethyl ether (2×20 mL). The combined organic extracts were washed with brine (30 mL) and then dried and evaporated in vacuo. The residue was triturated with isohexane (20 mL) to afford the title compound, Intermediate A15, as a beige solid (1.60 g, 77%); R$^t$ 3.35 min (Method 1 basic); m/z 214 (M+H)$^+$, (ES$^+$).

Intermediate A16

3-tert-Butyl-1-(3-methoxy-4-((triisopropylsilyloxy) methyl)phenyl)-1H-pyrazol-5-amine

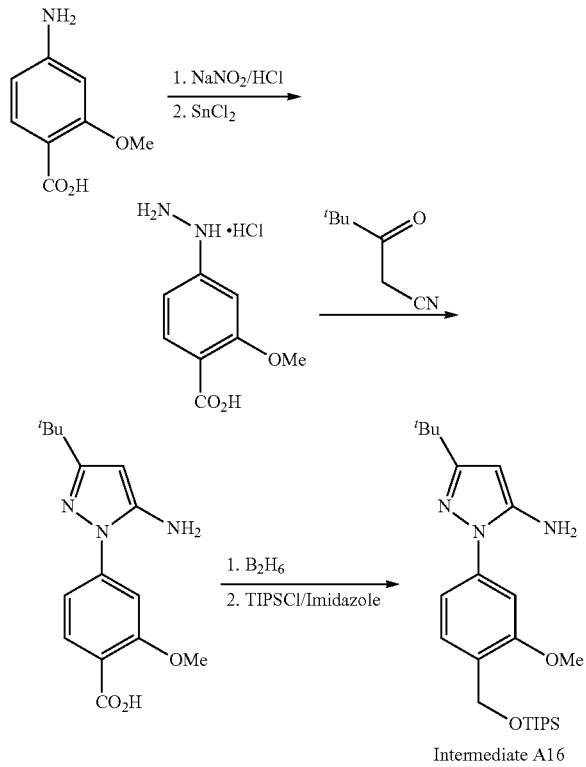

Intermediate A16

To a suspension of 4-amino-2-methoxybenzoic acid (3.00 g, 18.0 mmol) in hydrochoric acid (1.0 M, 30 mL) at 0° C. was added a solution of sodium nitrite (1.28 g, 18.5 mmol) in water (5.0 mL) over 5 min. The reaction mixture was maintained at 0° C. for 5 hr and was then treated with tin(II) chloride (9.53 g, 50.3 mmol) in hydrochloric acid (1M, 60 mL) and warmed to RT for 64 hr. A thick precipitate formed which was isolated by filtration, washed with water (50 mL) and ether (15 mL) and dried in vacuo to afford 2-methoxy-4-hydrazinylbenzoic acid hydrochloride as a beige solid (1.05 g, 90% purity, 24%); R$^t$ 0.17 min (Method 2); m/z 181 (M+H)$^+$, (ES$^+$). This material was used in the subsequent step without further purification.

A suspension of 2-methoxy-4-hydrazinylbenzoic acid hydrochloride (1.05 g, 90% purity, 4.34 mmol) and 4,4-dimethyl-3-oxopentanenitrile (664 mg, 5.31 mmol) in ethanol (20 mL) containing conc hydrochloric acid (12 M, 0.44 mL, 5.0 mmol) was heated at reflux for 28 hr and then cooled to RT. The reaction mixture was treated with aq NaOH (2.0 M, 8.6 mL, 17 mmol) and was maintained at RT for 20 hr and then concentrated to half its original volume in vacuo. Then residue was washed with DCM (2×15 mL) and the aq layer was acidified to pH 5 with conc hydrochloric acid (12 M, 1.0 mL) and re-extracted with DCM (5×30 mL). The combined organic extracts were washed with brine (10 mL) and then dried and evaporated in vacuo to afford 4-(5-amino-3-tert-butyl-1H-pyrazol-1-yl)-2-methoxybenzoic acid as a brown solid (900 mg, 61%); R$^t$ 1.47 min (Method 2); m/z 290 (M+H)$^+$, (ES$^+$).

To a solution of 4-(5-amino-3-(tert-butyl)-1H-pyrazol-1-yl)-2-methoxybenzoic acid (900 mg, 3.11 mmol) in THF (6.0 mL) at 0° C. under N$_2$ was added a solution of borane in THF (1.0 M 8.0 mL, 8.0 mmol) over 5 min and the reaction mixture warmed to RT. Additional aliquots of the borane solution were added after 22 hr (1.0 mL, 1.0 mmol) and 27 hr (1.7 mL, 1.7 mmol) and after 46 hr the reaction was quenched with MeOH (30 mL), kept at RT for 10 min and then evaporated in vacuo. The residue was partitioned between DCM (20 mL) and brine (10 mL) and the aq layer was separated and extracted with DCM (10 mL). The combined organic layers were dried and evaporated in vacuo to afford 3-tert-butyl-1-(3-chloro-4-(hydroxy methyl)phenyl)-1H-pyrazol-5-amine as a dark orange oil (840 mg, 90% purity, 88%); R$^t$ 3.62 min (Method 1 basic); m/z 276 (M+H)$^+$, (ES$^+$). This material was used in the subsequent step without further purification To a solution of 3-tert-butyl-1-(3-chloro-4-(hydroxymethyl)phenyl)-1H-pyrazol-5-amine (840 mg, 90% purity, 2.75 mmol) in dry THF (10 mL) under N$_2$ was added imidazole (240 mg, 3.5 mmol) and chlorotriisopropylsilane (720 µL, 650 mg, 3.40 mmol) and the reaction mixture kept at RT for 18 hr. The resulting mixture was diluted with DCM (5.0 mL) and was treated with a second aliquot of chlorotriisopropylsilane (720 µL, 650 mg, 3.40 mmol) and after a further 5 hr with additional imidazole (240 mg, 3.50 mmol). After 20 hr the reaction mixture was treated for a third time with chlorotriisopropylsilane (360 µL, 330 mg, 1.70 mmol) and imidazole (120 mg, 1.8 mmol) and after 3 days was evaporated in vacuo. The residue was taken up into EtOAc (50 mL) and was washed with water (20 mL) and brine (10 mL) and then dried and evaporated in vacuo. The residue was purified by flash column chromatography (SiO$_2$, 40 g, EtOAc in isohexane, 0-100%, gradient elution) and then by SCX capture and release to afford a brown oil which comprised of a mixture of starting material and the desired product. This mixture was taken up into THF (1.0 mL) and was treated with chlorotriisopropylsilane (200 µL, 200 mg, 0.30 mmol) and imidazole (75 mg, 1.1 mmol) and was maintained at RT for 24 hr and then evaporated in vacuo. The residue was partitioned between EtOAc (10 mL) and water (10 mL) and the organic phase was separated and extracted brine (10 mL) and then dried and evaporated in vacuo. The residue was purified by flash column chromatography (SiO$_2$, 40 g, EtOAc in isohexane, 0-100%, gradient elution) to afford the title compound, Intermediate A16 as a yellow oil (510 mg, 37%); R$^t$ 5.74 min (Method 1 basic); m/z 432 (M+H)$^+$, (ES$^+$).

Intermediate B3

7-((4-Aminonaphthalen-1-yl)oxy)-1-ethyl-1H-imidazo[4,5-b]pyridin-2(3H)-one

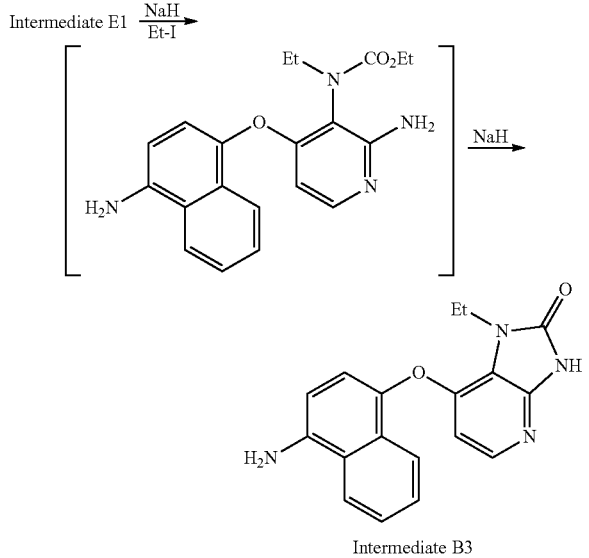

Intermediate B3

To a solution of Intermediate E1 (500 mg, 1.48 mmol) in DMF (10 mL) at 0° C. under N₂ was added sodium hydride (60% wt in mineral oil, 59 mg, 1.5 mmol) and after 1 hr the mixture was treated drop-wise, over 1 hr, with a solution of iodoethane (120 µL, 230 mg, 1.5 mmol) in DMF (1.5 mL). The resulting mixture was warmed to RT and after 2 hr was re-cooled to 0° C., and sodium hydride (60% wt in mineral oil, 120 mg, 3.0 mmol) was added. The reaction mixture was warmed to RT for 1 hr and was then poured onto ice-water (100 mL). The mixture was extracted with EtOAc (3×60 mL) and the combined organic extracts were washed with brine (3×50 mL) and then dried and evaporated in vacuo to afford a brown oil. This residue was triturated with ether and the resulting solid was isolated by filtration and washed with ether to afford Intermediate B3 as a pale brown solid (332 mg, 89% purity by HPLC, 63%); $R^t$ 1.50 min (Method 2, 89% pure); m/z 321 (M+H)⁺ (ES⁺).

Intermediate B4

7-((4-Aminonaphthalen-1-yl)oxy)-1-isopropyl-1H-imidazo[4,5-b]pyridin-2(3H)-one

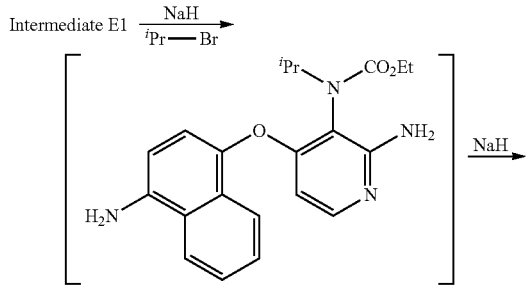

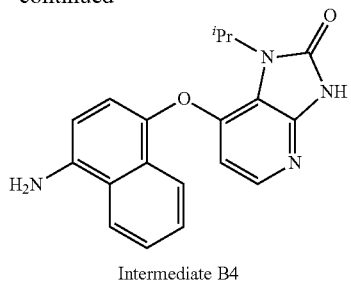

Intermediate B4

To a solution of Intermediate E1 (500 mg, 1.48 mmol) in DMF (10 mL) at 0° C. under N₂ was added sodium hydride (60% wt in mineral oil, 59 mg, 1.5 mmol) and after 1 hr the resulting mixture was treated drop-wise over 1 hr with a solution of 2-bromopropane (140 µL, 180 mg, 1.5 mmol) in DMF (1.5 mL). The mixture was warmed to RT for 48 hr and was then heated to 80° C. and treated with a second aliquot of 2-bromopropane (33 µL, 42 mg, 0.35 mmol) in DMF (0.5 mL), followed immediately by sodium hydride (60% wt in mineral oil, 14 mg, 0.35 mmol). The reaction mixture was maintained at 80° C. for 1 hr and was then cooled to RT. After a further 4 days sodium hydride (60% wt in mineral oil, 120 mg, 3.0 mmol) was added and the reaction mixture was maintained at RT for 1 hr and then poured onto ice-water (100 mL). The mixture was extracted with EtOAc (3×60 mL) and the combined organic extracts were washed with brine (3×50 mL), dried and evaporated in vacuo to afford a brown oil. This residue was triturated with ether and the resulting solid was isolated by filtration and washed with ether to afford Intermediate B4 as a pale brown solid (223 mg, 81% purity by HPLC, 36%); $R^t$ 1.66 min (Method 2, 81% pure); m/z 335 (M+H)⁺ (ES⁺).

Intermediate B5

7-(4-Amino-2,3-dichlorophenoxy)-1-methyl-1H-imidazo[4,5-b]pyridin-2(3H)-one

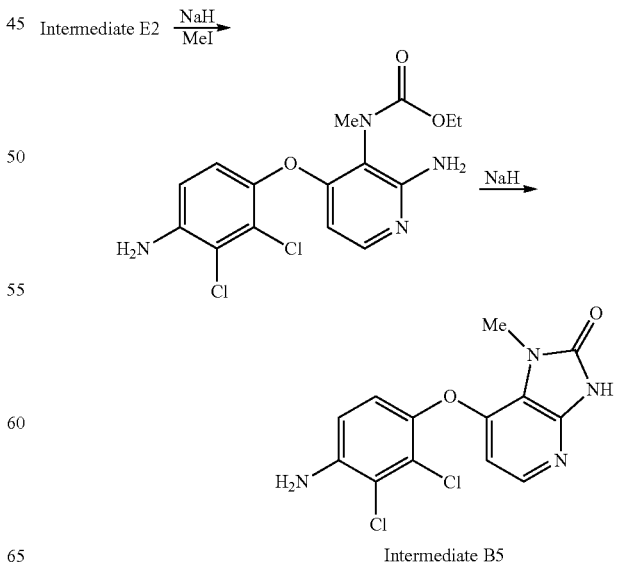

Intermediate B5

To a solution of Intermediate E2 (230 mg, 0.640 mmol) in dry DMF (4.0 mL) at 0° C. under N₂ was added sodium hydride (60% dispersion in mineral oil, 26 mg, 0.64 mmol) portionwise, over 2 min. After 45 min at 0° C. the reaction mixture was treated dropwise, over 2 min, with iodomethane (40 μL, 0.64 mmol) in DMF (1.0 mL) and was then warmed to RT for 6.5 hr and treated with a second aliquot of iodomethane (8 μL, 0.1 mmol) in dry DMF (0.1 mL). After 3 days the reaction mixture was re-cooled to 0° C. and sodium hydride (60% dispersion in mineral oil, 52 mg, 1.3 mmol) was added portionwise over 2 min. The resulting mixture was warmed to RT for 22 hr and was then partitioned between EtOAc (30 mL), and a mixture of water (30 mL) and sat brine (15 mL). The aq layer was separated and was extracted with EtOAc (3×25 mL) and the combined organic extracts were dried and evaporated in vacuo. The residue was purified by flash column chromatography (SiO₂, 40 g, MeOH in DCM, 0-8%, gradient elution) to afford Intermediate B5 as a brown solid (11 mg, 5%); R$^t$ 1.64 min (Method 2); m/z 325/327 (M+H)⁺ (ES⁺).

Intermediate B6

6-((4-Aminonaphthalen-1-yl)oxy)-7H-purin-8(9H)-one

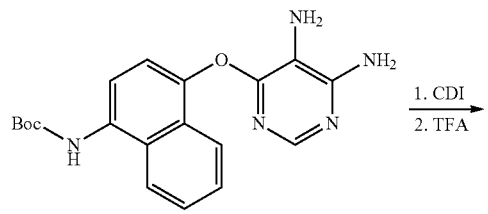

Intermediate F1

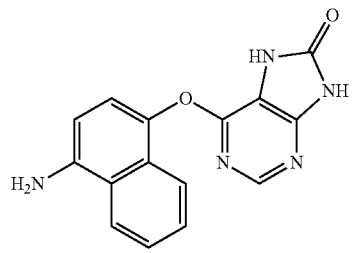

Intermediate B6

To a solution of Intermediate F1 (330 mg, 56% pure, 0.50 mmol) in DMF (6.0 mL) at RT under N₂ was added CDI (168 mg, 1.04 mmol) and the reaction mixture maintained at RT and treated with additional portions of CDI (168 mg, 1.04 mmol) after 4.5 hr, after 22.5 hr and after 27 hr. After a total of 48 hr the resulting mixture was partitioned between EtOAc (35 mL) and sat aq. NaHCO₃ (35 mL). The aq layer was separated and extracted with EtOAc (4×35 mL) and the combined organic extracts were washed with brine (30 mL) and then dried and evaporated in vacuo. The residue was purified by flash column chromatography (SiO₂, 40 g, [5% MeOH in EtOAc] in isohexane, 0-100%, gradient elution) to afford tert-butyl (4-((8-oxo-8,9-dihydro-7H-purin-6-yl)oxy) naphthalen-1-yl)carbamate as a pale brown solid (119 mg, 59%); R$^t$ 1.81 min (Method 2); m/z 394 (M+H)⁺ (ES⁺).

To a solution of the product obtained above (119 mg, 0.302 mmol) in DCM (6.0 mL) at 0° C. under N₂ was added TFA (2.0 mL, 30 mmol) and the reaction mixture warmed to RT for 3 hr and then evaporated in vacuo. The residue was purified by SCX capture and release to afford Intermediate B6; R$^t$ 0.94 min (Method 2, 89% pure); m/z 294 (M+H)⁺ (ES⁺). This material was used as obtained, without further purification.

Intermediate C1

1-(8-((2-Amino-3-nitropyridin-4-yl)oxy)quinolin-5-yl)-3-(3-(tert-butyl)-1-(4-methoxyphenyl)-1H-pyrazol-5-yl)urea

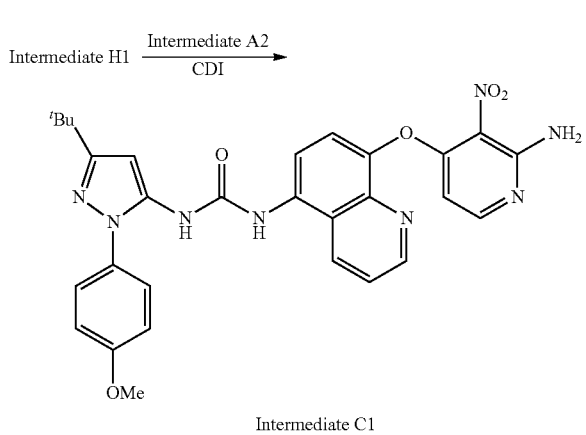

Intermediate C1

To a solution of CDI (500 mg, 3.00 mmol) in dry DCM (6.0 mL) at RT was added Intermediate A2 (760 mg, 3.10 mmol) and the mixture kept at RT for 4 hr and then treated with a solution of Intermediate H1 (600 mg, 2.00 mmol) in dry THF (5.0 mL). After 2 hr the reaction was quenched with MeOH (3.0 mL) for 5 min at RT and was then evaporated in vacuo. The residue was triturated with water (50 mL) and then purified by flash column chromatography (SiO₂, 80 g, MeOH in DCM, 0-5%, gradient elution) to afford Intermediate C1 as a yellow solid (520 g, 45%); R$^t$ 2.12 min (Method 2); m/z 569 (M+H)⁺, (ES⁺);

Intermediate D2

8-(4-Amino-2,3-dichlorophenoxy)pyrido[2,3-b]pyrazin-3(4H)-one

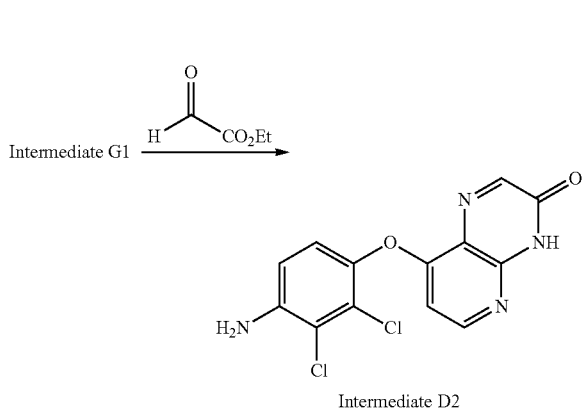

Intermediate D2

To a solution of Intermediate G1 (440 mg, 1.54 mmol) in EtOH (10 mL) under N₂ at reflux was added ethyl glyoxolate (0.5 M in toluene, 400 µL, 2.0 mmol). The reaction mixture was maintained at reflux for 1.5 hr and was then cooled to RT, during which time a precipitate formed. This precipitate was isolated by filtration and washed with isohexane to afford the title compound, Intermediate D2 as a brick red solid (128 mg, 92% purity, 24%); R$^t$ 1.72 min (Method 2, 92% pure); m/z 323 (M+H)$^+$ (ES$^+$).

Intermediate D3

4-((4-aminonaphthalen-1-yl)oxy)pteridin-7(8H)-one

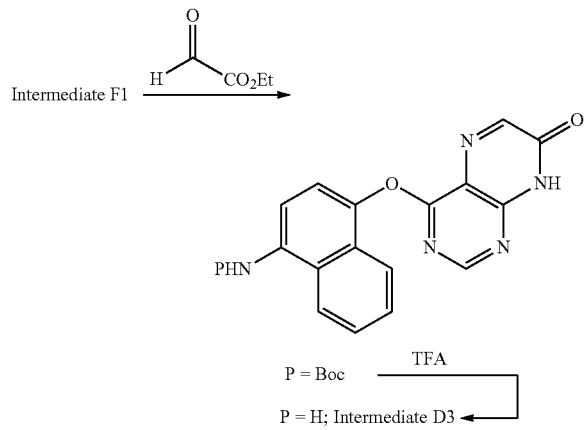

To a solution of the Intermediate F1 (6.9 g, 19 mmol) in EtOH (6.0 mL) at RT under N₂ was added ethyl 2-oxoacetate (50% solution in toluene, 5.6 mL, 28 mmol) and the reaction mixture maintained at RT for 16 hr and then heated at reflux for 5 hr, during which time a precipitate formed. The reaction mixture was cooled to RT and the precipitate was isolated by filtration to afford tert-butyl 4-(7-oxo-7,8-dihydropteridin-4-yloxy)naphthalen-1-ylcarbamate as a pale pink solid (3.5 g, 42%); R$^t$ 1.90 min (Method 2); m/z 406 (M+H)$^+$ (ES$^+$).

To a solution of the product obtained above (50 mg, 0.12 mmol) in DCM (1.0 mL) at RT was added TFA (0.47 mL, 0.70 g, 6.2 mmol). After 30 min at RT the reaction mixture was evaporated in vacuo to afford Intermediate D3 as a dark brown oil (90 mg, 80% purity by HPLC, >100%); R$^t$ 1.10 min (Method 2); m/z 306 (M+H)$^+$ (ES$^+$). This material was used in subsequent steps without further purification.

Intermediate D4

8-((4-aminonaphthalen-1-yloxy)methyl)pyrido[2,3-b]pyrazin-3(4H)-one

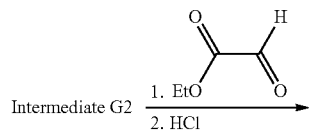

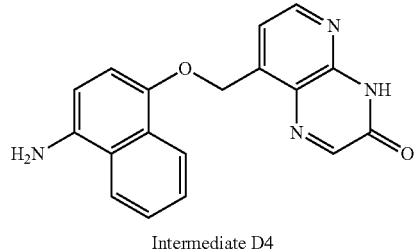

Intermediate D4

To a solution of Intermediate G2 (170 mg, 0.56 mmol) in EtOH (5.0 mL) at reflux was added ethyl 2-oxoacetate (50% v/v in toluene, 190 µL, 0.97 mmol) and the reaction mixture was maintained at 80° C. for 30 min during which time a brown precipitate formed. The reaction mixture was cooled to RT and the solid was isolated by filtration, triturated with methanol and purified by flash column chromatography (SiO₂, 40 g, 5% MeOH in DCM, isocratic elution). The crude product so obtained was triturated with MeOH, washed with ether and then suspended in THF (3.0 mL). Hydrochloric acid (1M, 0.4 mL, 0.4 mmol) was added and the mixture was sonicated for 5 min during which time a white precipitate formed. The solid which was collected by filtration and was washed with THF (2×1.0 mL) to afford the title compound, Intermediate D4 as a pale yellow solid (7.5 mg, 85% purity by HPLC, 4%); R$^t$1.14 min (Method 2 basic); m/z 317 (M−H)$^−$, (ES$^−$).

Intermediate E2

Ethyl (2-amino-4-(4-amino-2,3-dichlorophenoxy)pyridin-3-yl) carbamate

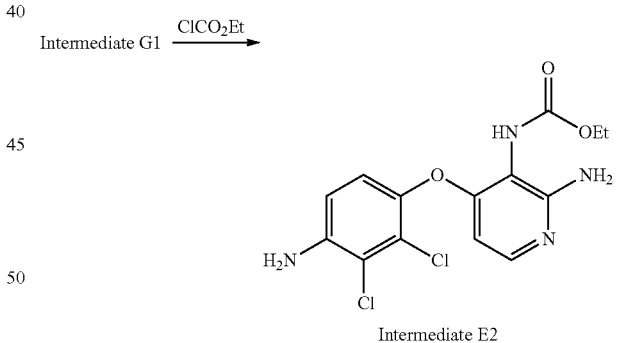

Intermediate E2

To a solution of Intermediate G1 (440 mg, 1.54 mmol) and pyridine (250 µL, 3.00 mmol) in THF (20 mL) at 0° C. under N₂ was added ethyl chloroformate (1 M solution in THF, 1.62 mL, 1.62 mmol) over 5 min. The reaction mixture was maintained at 0° C. for 1.5 hr and was then partitioned between EtOAc (50 mL) and sat aq. NaHCO₃ (40 mL). The aq layer was separated and was extracted with EtOAc (50 mL) and the combined organic extracts were dried and evaporated in vacuo. The residue was purified by flash column chromatography (SiO₂, 40 g, MeOH in DCM, 0-10%, gradient elution) to afford Intermediate E2 as a pale purple solid (235 mg, 90% purity by HPLC, 38%); R$^t$ 1.36 min (Method 2); m/z 357 (M+H)$^+$(ES$^+$)

Intermediate F1

6-((4-Aminonaphthalen-1-yl)oxy)-7H-purin-8(9H)-one

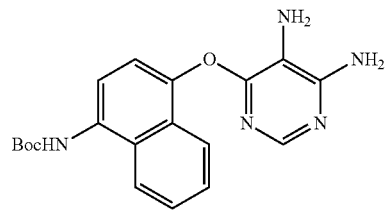

To a solution of Intermediate J1 (8.02 g, 21.8 mmol) in AcOH (100 mL). was added iron powder (6.75 g, 121 mmol) and the resulting mixture was heated to 50° C. for 1 hr and was then filtered through a pad of celite. The pad was washed with EtOAc/THF (3:1 v/v, 500 mL), and the filtrate and washings were combined and evaporated in vacuo. The residue was partitioned between EtOAc/THF (3:1 v/v, 400 mL) and water (300 mL). The aq layer was separated and adjusted to pH8 with solid $Na_2CO_3$) and was then extracted with EtOAc/THF (3:1 v/v, 200 mL). The combined organic extracts were washed with water (300 mL) and brine (300 mL) and then dried ($Na_2SO_4$) and evaporated in vacuo to afford Intermediate F1 as a brown solid (6.9 g, 93%); $R^t$ 1.59 min (Method 2); m/z 368 $(M+H)^+$ $(ES^+)$.

Intermediate G1

4-(4-Amino-2,3-dichlorophenoxy)pyridine-2,3-diamine

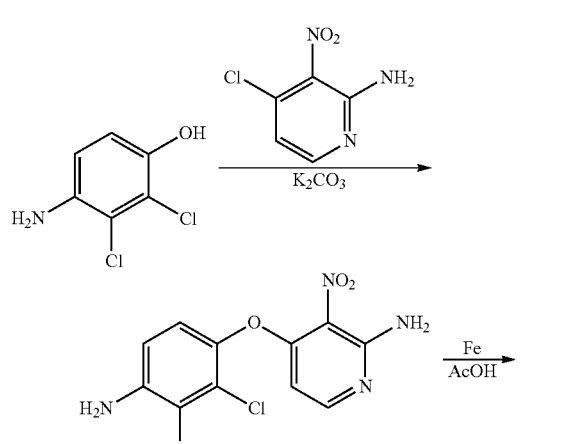

To a stirred solution of 4-amino-2,3-dichlorophenol (1.00 g, 5.62 mmol) in dry DMF (20 mL) under $N_2$ was added $K_2CO_3$ (854 mg, 6.18 mmol) and the mixture kept at RT for 10 min and then treated with a solution of 4-chloro-3-nitropyridin-2-amine (1.024 g, 5.90 mmol) in dry DMF (5.0 mL) in a single portion. The reaction mixture was maintained at RT for 19 hr and was then partitioned between EtOAc (100 mL) and water (100 mL). The aq layer was separated and was extracted with EtOAc (4×70 mL) and the combined organic extracts were dried and evaporated in vacuo. The residue was purified by flash column chromatography ($SiO_2$, 80 g, EtOAc in isohexane, 0-70%, gradient elution) to afford 4-(4-amino-2,3-dichlorophenoxy)-3-nitro-pyridin-2-amine as a dark solid (1.28 g, 70%); $R^t$ 1.85 min (Method 2); m/z 315 $(M+H)^+$ $(ES^+)$.

A suspension of the nitroarene obtained above (1.28 g, 4.06 mmol) and iron powder (1.36 g, 24.4 mmol) in AcOH (200 mL) was heated to 55° C. for 1.5 hr and was then cooled to RT and diluted with EtOAc (20 mL). The mixture was filtered through a pad of celite, which was then washed with EtOAc and with THF. The filtrate and washings were combined and evaporated in vacuo and the residue was partitioned between sat aq $NaHCO_3$ and EtOAc/THF (3:1 v/v, 100 mL). The aq layer was separated and extracted with EtOAc/THF (3:1 v/v, 2×80 mL) and the combined organic extracts were dried and evaporated in vacuo to afford Intermediate G1 as a dark purple oil (886 mg, 75%); $R^t$ 0.99 min (Method 2); m/z 285 $(M+H)^+$ $(ES^+)$.

Intermediate G2

4-((4-aminonaphthalen-1-yloxy)methyl)pyridine-2,3-diamine

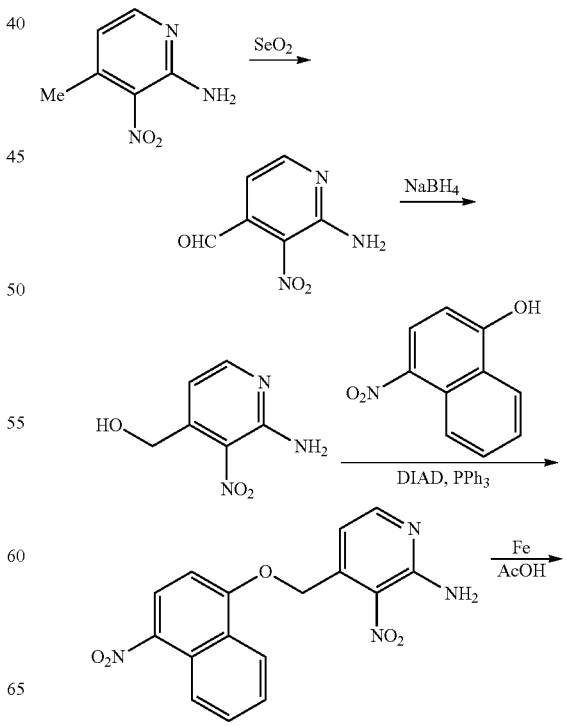

-continued

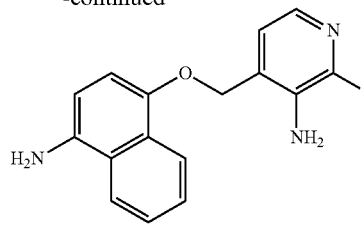

Intermediate G2

To a solution of 4-methyl-3-nitropyridin-2-amine (10.0 g, 65.0 mmol) in a mixture of dioxane (400 mL) and water (50 mL) was added selenium dioxide (29.0 g, 260 mmol) and the reaction mixture was heated to 100° C. for 16 hr and then cooled to RT and filtered through a pad of celite. The pad was washed with a mixture of EtOAc/THF (3:1 v/v, 100 mL) and the combined filtrate and washings were evaporated in vacuo. The residue was partitioned between EtOAc/THF (3:1 v/v, 100 mL) and sat aq. NaHCO$_3$ (150 mL) diluted with water (150 mL). The aq layer was separated and was extracted with EtOAc/THF (3:1 v/v, 4×100 mL) and the combined organic extracts were dried and evaporated in vacuo to afford 2-amino-3-nitroisonicotinaldehyde as a brown solid (2.73 g, 25%); R$^t$ 0.75 min (Method 2); m/z 168 (M+H)$^+$, (ES$^+$).

To a suspension of the aldehyde obtained above (850 mg, 5.1 mmol) in MeOH (25 mL) at 0° C. was added sodium tetrahydroborate (190 mg, 5.10 mmol) and the reaction mixture warmed to RT for 2 hr and then quenched by the addition of hydrochloric acid (1 M, 5.0 mL) The mixture was diluted with sat aq. NaHCO$_3$ (40 mL) and was extracted with DCM (80 mL, 6×100 mL). The combined organic extracts were dried and evaporated in vacuo to afford (2-amino-3-nitropyridin-4-yl)methanol as an orange solid (630 mg, 69%); R$^t$ 0.40 min (Method 2); m/z 170 (M+H)$^+$, (ES$^+$).

To a suspension of the alcohol obtained above (500 mg, 2.70 mmol), 4-nitronaphthalen-1-ol (500 mg, 2.70 mmol) and triphenylphosphine (980 mg, 3.70 mmol) in THF (5.0 mL) at −78° C. was added DIAD (780 μL, 810 mg, 4.00 mmol). Upon completion of the addition the reaction mixture was warmed to RT for 3 hr and was then quenched by the addition of methanol and evaporated in vacuo. The residue was triturated with MeOH to afford 3-nitro-4-(((4-nitronaphthalen-1-yl)oxy)methyl)pyridin-2-amine as a yellow solid (170 mg, 19%); R$^t$ 2.30 min (Method 2); m/z 341 (M+H)$^+$, (ES$^+$).

A suspension of the nitroarene obtained above (170 mg, 0.51 mmol) and iron powder (170 mg, 3.0 mmol) in AcOH (3.0 mL) was heated to 60° C. for 3 hr. An additional portion of iron powder (0.85 g, 1.5 mmol) was added and the mixture heated for a further 2 hr and then filtered through a pad of celite. The celite pad was washed with EtOAc/THF (3:1 v/v, 50 mL) and the filtrate and washings were combined and evaporated in vacuo. The residue was co-evaporated with toluene in vacuo and the residue was partitioned between EtOAc/THF (3:1 v/v, 100 mL) and water. Solid Na$_2$CO$_3$ was added to the mixture until the aq layer was basic (universal indicator paper). The layers were separated and the aq layer was extracted with EtOAc/THF (3:1 v/v, 2×50 mL). The organic extracts were combined, washed with brine (2×50 mL) and then dried and evaporated in vacuo to afford Intermediate G2 as a brown/black solid (140 mg, 85% purity by HPLC, 85%). R$^t$ 0.81 min (Method 2); m/z 281 (M+H)$^+$, (ES$^+$).

Intermediate H1

8-((2-Amino-3-nitropyridin-4-yl)oxy)quinolin-5-amine

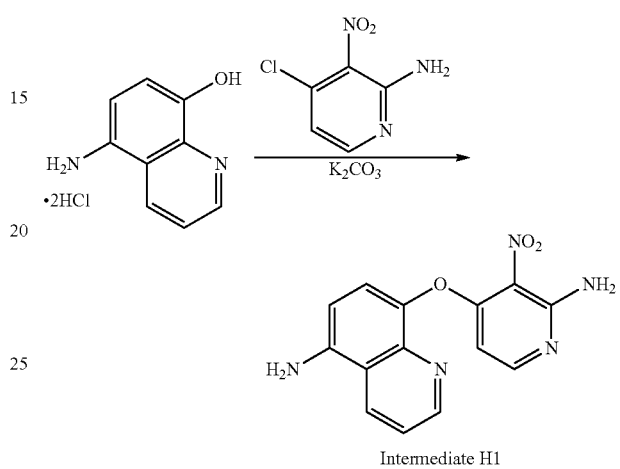

Intermediate H1

To a stirred solution of 5-aminoquinolin-8-ol dihydrochloride (2.00 g, 8.60 mmol) in DMSO (30 mL) under N$_2$ was added K$_2$CO$_3$ (3.79 g, 27.5 mmol) and after 1 hr at RT the mixture was treated with 4-chloro-3-nitropyridin-2-amine (1.34 g, 7.72 mmol) in a single portion. The reaction mixture was heated to 70° C. for 2 hr and was then cooled to RT and diluted with water (500 mL). A precipitate formed which was isolated by filtration, washed with water (2×20 mL) and then dried in vacuo at 40° C. to afford the title compound, Intermediate H1 as a dark brown solid (1.50 g, 53%); R$^t$ 0.99 min (Method 2); m/z 298 (M+H)$^+$ (ES$^+$).

Intermediate J1 tert-Butyl (4-((6-amino-5-nitropyrimidin-4-yl)oxy)naphthalen-1-yl) carbamate

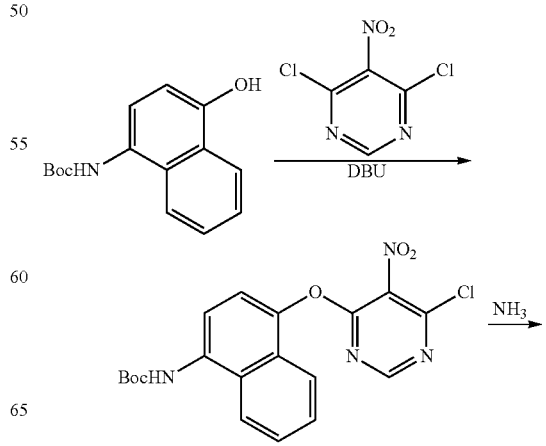

-continued

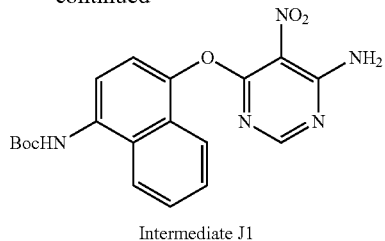

Intermediate J1

To a stirred solution of tert-butyl (4-hydroxynaphthalen-1-yl)carbamate (20.0 g, 73.0 mmol) in MeCN (200 mL) under $N_2$ was added DBU (13 mL, 87 mmol) and after 1 hr at RT the resulting mixture was treated dropwise with a solution of 4,6-dichloro-5-nitropyrimidine (15.5 g, 80.0 mmol) in MeCN (150 mL). After 2.5 hr at RT the mixture was evaporated in vacuo and the residue was triturated with DCM (150 mL) and isohexane (200 mL). The insoluble residue was separated and set aside and the triturant was evaporated in vacuo. The residue so obtained was partitioned between DCM (200 mL) and sat aq $NaHCO_3$ (200 mL) and the organic layer was separated and evaporated in vacuo. The residue was triturated with EtOAc to give an off white solid (batch 1). The EtOAc triturant was concentrated in vacuo to ~20 mL and the precipitate which formed was isolated by filtration and washed with EtOAc to afford a second batch of same material, also as an off white solid. The first and second batches of product were combined to afford tert-butyl (4-((6-chloro-5-nitropyrimidin-4-yl)oxy)naphthalen-1-yl)carbamate (10.4 g, 34%); R'2.69 min (Method 2); m/z 439/441 (M+Na)$^+$ (ES$^+$).

The original insoluble residue was suspended in DCM (150 mL) and isohexane (200 mL) and the mixture was stirred vigorously for 16 hr. The supernatant liquor was decanted from the mixture and filtered. The filtrate was evaporated in vacuo and the residue was triturated with isohexane/EtOAc (2:1 v/v) to afford a third batch of the same product, as a pale pink solid (6.3 g, 21%).

To a solution of the di-aryl ether obtained above (15.7 g, 37.7 mmol) in THF (160 mL) at RT was added $NH_3$ (2M solution in IPA, 75 mL, 150 mmol) and after 1 hr at RT the reaction mixture was evaporated in vacuo. The residue was partitioned between a mixture of $CHCl_3$/MeOH (9:1 v/v, 350 mL) and water (350 mL). The organic layer was separated, dried and evaporated in vacuo and the residue was triturated with ether (200 mL) to afford Intermediate J1 as a yellow solid (8.2 g, 55%); R' 2.17 min (Method 2); m/z 398 (M+H)$^+$ (ES$^+$).

COMPOUND EXAMPLES

Those reference compounds employed as biological screening standards and compound examples of the invention that have been previously disclosed were prepared according to the procedures described in the literature sources cited (Table 3).

TABLE 3

Screening Standards and Compound Examples

| Example No. | Structure | Compound Name & Lit. Reference |
|---|---|---|
| BIRB 796 | 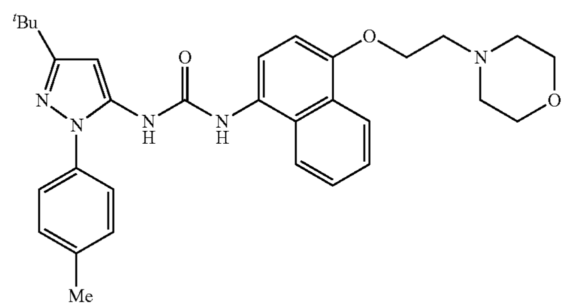 [SMILES: Cc1ccc(-n2nc(C(C)(C)C)cc2NC(=O)Nc2ccc(OCCN3CCOCC3)c3ccccc23)cc1] | 1-(3-tert-butyl-1-p-tolyl-1H-pyrazol-5-yl)-3-(4-(2-morpholinoethoxy)naphthalen-1-yl)urea<br>Kuma, Y. et al., *J. Biol. Chem.*, 2005, 280, 19472-19479 |
| Ref. 1 | 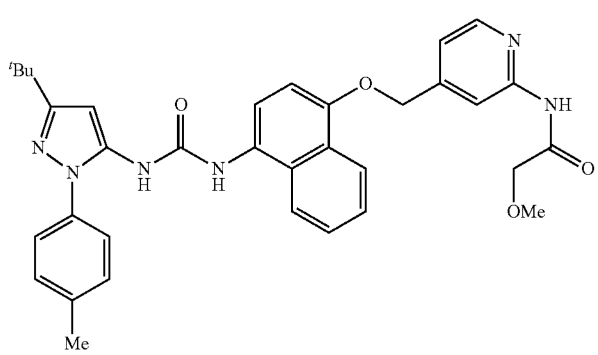 [SMILES: COCC(=O)Nc1cc(COc2ccc(NC(=O)Nc3cc(C(C)(C)C)nn3-c3ccc(C)cc3)c3ccccc23)ccn1] | N-(4-((4-(3-(3-tert-butyl-1-p-tolyl-1H-pyrazol-5-yl)ureido)naphthalen-1-yloxy)methyl)pyridin-2-yl)-2-methoxyacetamide.<br>Ito, K. et al., WO 2010/038086. |

TABLE 3-continued

Screening Standards and Compound Examples

| Example No. | Structure | Compound Name & Lit. Reference |
|---|---|---|
| Ref 2 | 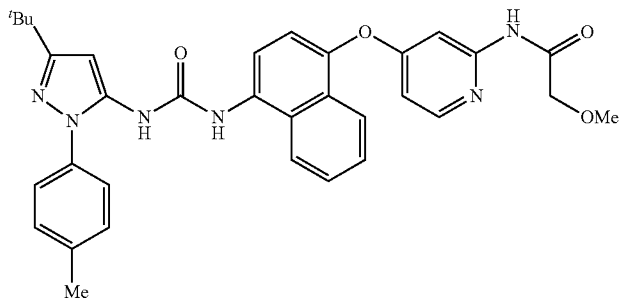 [SMILES: COCC(=O)Nc1cc(Oc2ccc(NC(=O)Nc3cc(C(C)(C)C)nn3-c3ccc(C)cc3)c3ccccc23)ccn1] | N-(4-(4-(3-(3-tert-butyl-1-p-tolyl-1H-pyrazol-5-yl)ureido)naphthalen-1-yloxy)pyridin-2-yl)-2-methoxy acetamide.<br>Ito, K. et al., WO 2010/112936. |
| 1 | 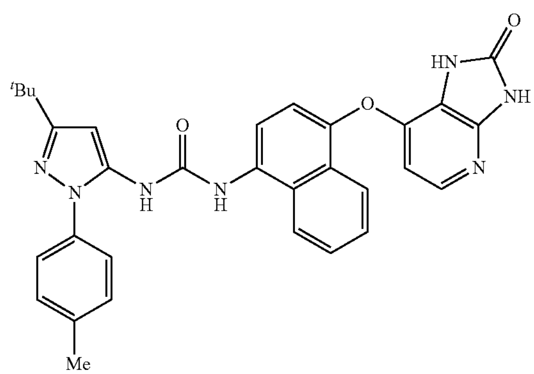 [SMILES: Cc1ccc(-n2nc(C(C)(C)C)cc2NC(=O)Nc2ccc(Oc3ccnc4[nH]c(=O)[nH]c34)c3ccccc23)cc1] | 1-(3-tert-butyl-1-p-tolyl-1H-pyrazol-5-yl)-3-(4-(2-oxo-2,3-dihydro-1H-imidazo[4,5-b]pyridin-7-yloxy)naphthalen-1-yl)urea.<br>Niculescu-Duvaz, D. et al., WO 2006/043090, 27 Apr. 2006.<br>Suijkerbuijk, B. M. J. M. et al., *J. Med. Chem.*, 2010, 53(7), 2741-56. |
| 2 | 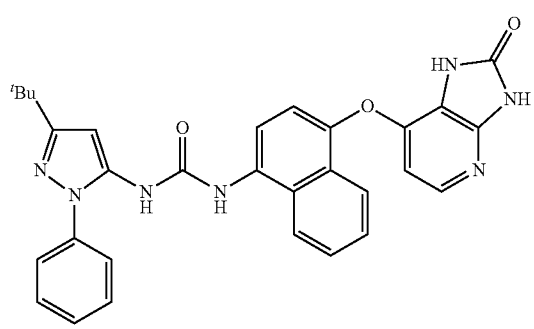 [SMILES: CC(C)(C)c1cc(NC(=O)Nc2ccc(Oc3ccnc4[nH]c(=O)[nH]c34)c3ccccc23)n(-c2ccccc2)n1] | 1-(3-tert-butyl-1-phenyl-1H-pyrazol-5-yl)-3-(4-(2-oxo-2,3-dihydro-1H-imidazo[4,5-b]pyridin-7-yloxy)naphthalen-1-yl)urea.<br>WO 2006/043090.<br>Suijkerbuijk, B. M. J. M. et al., *J. Med. Chem.*, 2010, 53(7), 2741-56. |
| 3 | 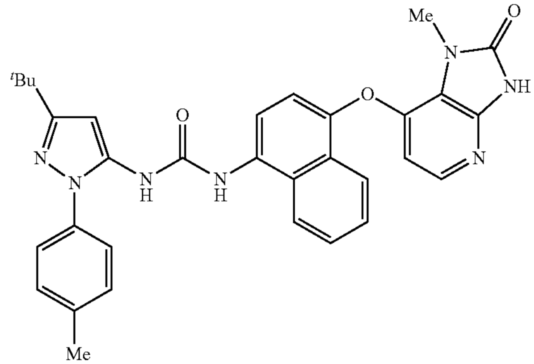 [SMILES: Cc1ccc(-n2nc(C(C)(C)C)cc2NC(=O)Nc2ccc(Oc3ccnc4[nH]c(=O)n(C)c34)c3ccccc23)cc1] | 1-(3-tert-butyl-1-p-tolyl-1H-pyrazol-5-yl)-3-(4-(1-methyl-2-oxo-2,3-dihydro-1H-imidazo[4,5-b]pyridin-7-yloxy)naphthalen-1-yl)urea.<br>WO 2006/043090.<br>Suijkerbuijk, B. M. J. M. et al., *J. Med. Chem.*, 2010, 53(7), 2741-56. |

TABLE 3-continued

Screening Standards and Compound Examples

| Example No. | Structure | Compound Name & Lit. Reference |
|---|---|---|
| 4 | 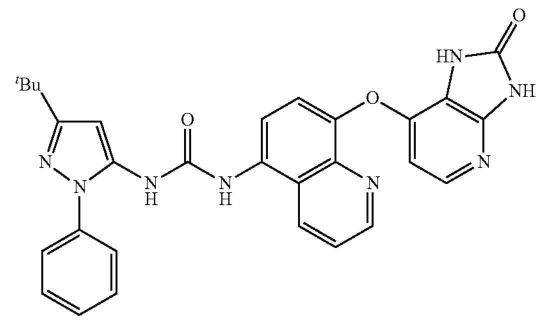 [SMILES: CC(C)(C)c1cc(NC(=O)Nc2ccc(Oc3ccnc4[nH]c(=O)[nH]c34)c3ncccc23)n(-c2ccccc2)n1] | 1-(3-tert-butyl-1-phenyl-1H-pyrazol-5-yl)-3-(8-(2-oxo-2,3-dihydro-1H-imidazo[4,5-b]pyridin-7-yloxy)quinolin-5-yl) urea.<br>Niculescu-Duvaz, I. et al., WO 2009/130487, 29 Oct. 2009. |
| 5 | 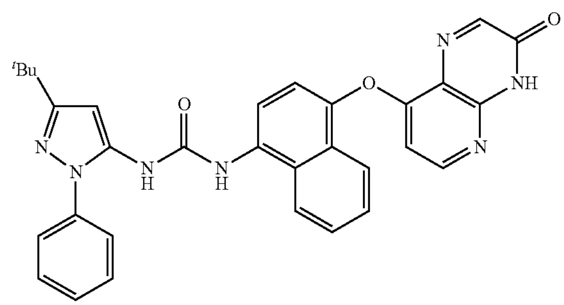 [SMILES: CC(C)(C)c1cc(NC(=O)Nc2ccc(Oc3ccnc4[nH]c(=O)cnc34)c3ccccc23)n(-c2ccccc2)n1] | 1-(3-(tert-butyl)-1-phenyl-1H-pyrazol-5-yl)-3-(4-((3-oxo-3,4-dihydropyrido[2,3-b]pyrazin-8-yl)oxy)naphthalen-1-yl) urea.<br>Zambon, A. et al., *J. Med. Chem.*, 2010, 53(15), 5639-5655. |
| 6 | 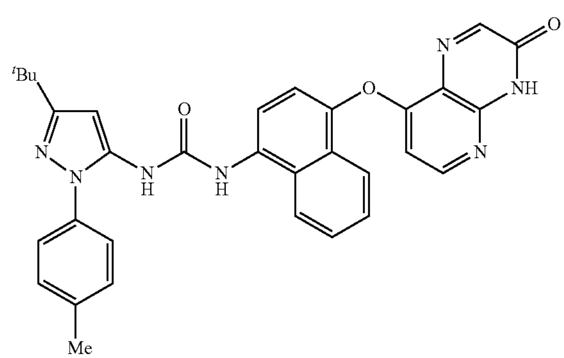 [SMILES: Cc1ccc(-n2nc(C(C)(C)C)cc2NC(=O)Nc2ccc(Oc3ccnc4[nH]c(=O)cnc34)c3ccccc23)cc1] | 1-(3-(tert-butyl)-1-(p-tolyl)-1H-pyrazol-5-yl)-3-(4-((3-oxo-3,4-dihydropyrido[2,3-b]pyrazin-8-yl)oxy)naphthalen-1-yl)urea.<br>Zambon, A. et al., *J. Med. Chem.*, 2010, 53(15), 5639-5655. |
| 7 | 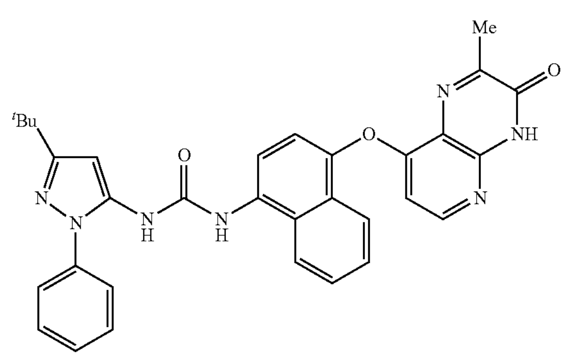 [SMILES: Cc1nc2c(Oc3ccc(NC(=O)Nc4cc(C(C)(C)C)nn4-c4ccccc4)c4ccccc34)ccnc2[nH]c1=O] | 1-(3-(tert-butyl)-1-phenyl-1H-pyrazol-5-yl)-3-(4-((2-methyl-3-oxo-3,4-dihydropyrido[2,3-b]pyrazin-8-yl)oxy)naphthalen-1-yl)urea.<br>Zambon, A. et al., *J. Med. Chem.*, 2010, 53(15), 5639-5655. |

TABLE 3-continued

Screening Standards and Compound Examples

| Example No. | Structure | Compound Name & Lit. Reference |
|---|---|---|
| 8 | 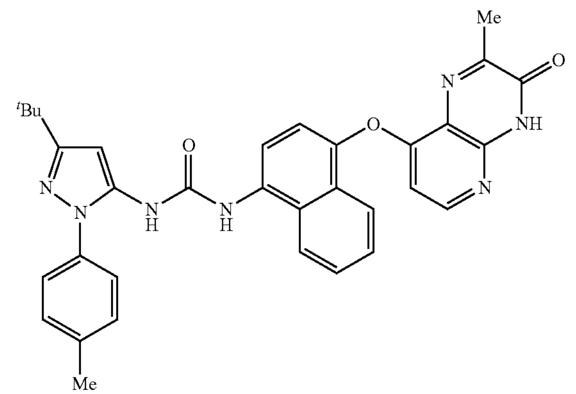 [SMILES: Cc1ccc(-n2nc(C(C)(C)C)cc2NC(=O)Nc2ccc(Oc3ccnc4[nH]c(=O)c(C)nc34)c3ccccc23)cc1] | 1-(3-(tert-butyl)-1-(p-tolyl)-1H-pyrazol-5-yl)-3-(4-((2-methyl-3-oxo-3,4-dihydro pyrido[2,3-b]pyrazin-8-yl)oxy) naphthalen-1-yl)urea. Zambon, A. et al., *J. Med. Chem.*, 2010, 53(15), 5639-5655. |

Example 9

1-(3-(tert-Butyl)-1-(4-methoxyphenyl)-1H-pyrazol-5-yl)-3-(4-((2-oxo-2,3-dihydro-1H-imidazo[4,5-b]pyridin-7-yl)oxy)naphthalen-1-yl)urea

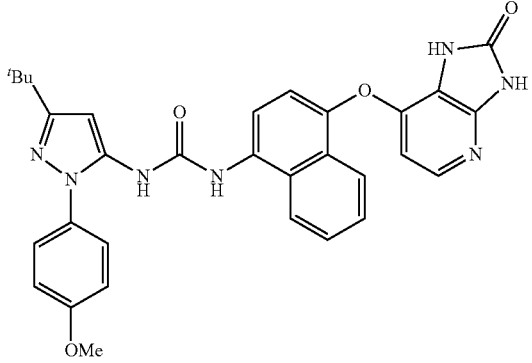

Example 9

Example 10

1-(3-(tert-Butyl)-1-(4-methoxyphenyl)-1H-pyrazol-5-yl)-3-(4-((1-methyl-2-oxo-2,3-dihydro-1H-imidazo[4,5-b]pyridin-7-yl)oxy)naphthalen-1-yl)urea

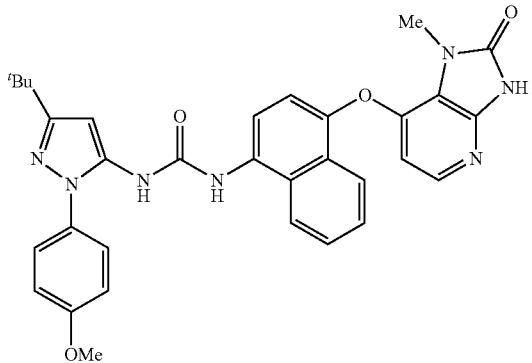

Example 10

To a solution of CDI (63 mg, 0.39 mmol) in dry DCM (1.0 mL) at RT was added Intermediate A2 (95 mg, 0.39 mmol), the reaction mixture kept at RT for 4 days and then treated with Intermediate B1 (70 mg, 0.24 mmol) and diluted with DCM (2.0 mL). After a further 16 hr the reaction was quenched with MeOH (1.0 mL) for 5 min at RT and evaporated in vacuo. The residue was triturated with water (50 mL) and with ether (10 mL) to afford the title compound, Example 9 as a dark brown solid (72 mg, 52%); $R^t$ 2.02 min (Method 2); m/z 564 (M+H)$^+$, (ES$^+$); $^1$H NMR (400 MHz, DMSO-$d_6$) δ: 1.27 (9H, s), 3.83 (3H, s), 6.20 (1H, d), 6.38 (1H, s), 7.12 (2H, d), 7.29 (1H, d), 7.48 (2H, d), 7.59 (1H, m), 7.65 (1H, m), 7.69 (1H, d), 7.90 (1H, d), 7.94 (1H, dd), 8.06 (1H, d), 8.71 (1H, s), 9.09 (1H, s), 11.36 (1H, br s), 11.42 (1H, br s).

To a solution of CDI (500 mg, 3.00 mmol) in dry DCM (6.0 mL) at RT was added Intermediate A2 (760 mg, 3.1 mmol) and the reaction mixture kept at RT for 4 hr. An aliquot of the resulting solution (0.70 mL, 0.40 mmol) was added to a suspension of Intermediate B2 (60 mg, 20 μmol) in dry THF (1.5 mL) and the reaction mixture was maintained at RT for 16 hr and was then quenched with MeOH (1.0 mL). After a further 5 min at RT the mixture was evaporated in vacuo and the residue was purified by flash column chromatography (SiO$_2$, 12 g, EtOAc in isohexane, 0-100%, gradient elution) to afford the title compound, Example 10 as a pale brown solid (99 mg, 86%); $R^t$ 2.16 min (method 2); m/z 578 (M+H)$^+$, (ES$^+$); $^1$H NMR (400 MHz, DMSO-$d_6$) δ: 1.28 (9H, s), 3.53 (3H, s), 3.83 (3H, s), 6.29 (1H, d), 6.38 (1H, s), 7.12 (2H, d), 7.25 (1H, d), 7.48 (2H, d), 7.60 (1H, m), 7.66 (1H, m), 7.74 (1H, d), 7.89 (1H, d), 8.07-8.09 (2H, overlapping m), 8.69 (1H, br s), 9.07 (1H, br s), 11.67 (1H, br s).

Example 11

1-(3-(tert-Butyl)-1-(4-methoxyphenyl)-1H-pyrazol-5-yl)-3-(4-((1-ethyl-2-oxo-2,3-dihydro-1H-imidazo[4,5-b]pyridin-7-yl)oxy)naphthalen-1-yl)urea

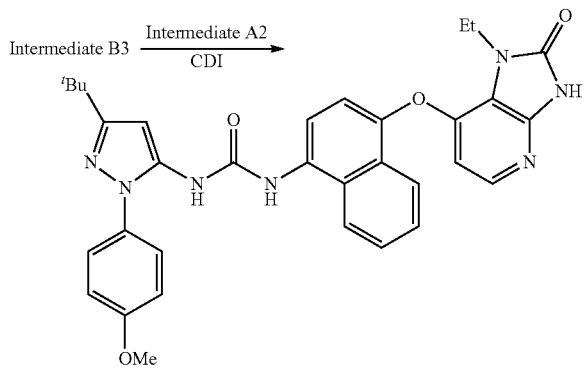

Example 11

To a solution of CDI (140 mg, 0.84 mmol) in dry DCM (1.0 mL) at RT was added Intermediate A2 (210 mg, 0.84 mmol) and the reaction mixture maintained at RT for 2 hr. An aliquot of the resulting solution (0.90 mL, 0.70 mmol) was added dropwise to a solution of Intermediate B3 (100 mg, 0.31 mmol) in dry THF (2.0 mL) and the reaction mixture was kept at RT for 3 days and was then partitioned between DCM (5.0 mL) and sat aq NaHCO$_3$ (5.0 mL). The organic layer was separated and dried and was treated with activated charcoal and evaporated in vacuo. The residue was purified by flash column chromatography (SiO$_2$, 12 g, MeOH in DCM, 0-5%, gradient elution) to afford the title compound, Example 11 as a pale brown solid (112 mg, 58%); R$^t$ 2.24 min (Method 2); m/z 592 (M+H)$^+$, (ES$^+$); $^1$H NMR (400 MHz, DMSO-d$_6$) δ: 1.28 (9H, s), 1.32 (3H, t), 3.84 (3H, s), 4.03 (2H, q), 6.28 (1H, d), 6.39 (1H, s), 7.13 (2H, d), 7.29 (1H, d), 7.49 (2H, d), 7.62 (1H, ddd), 7.68 (1H, ddd), 7.75 (1H, d), 7.91 (1H, d), 8.04 (1H, dd), 8.08 (1H, d), 8.72 (1H, brs), 9.11 (1H, brs), 11.71 (1H, br s).

Example 12

1-(3-(tert-Butyl)-1-(4-methoxyphenyl)-1H-pyrazol-5-yl)-3-(4-((1-isopropyl-2-oxo-2,3-dihydro-1H-imidazo[4,5-b]pyridin-7-yl)oxy)naphthalen-1-yl)urea

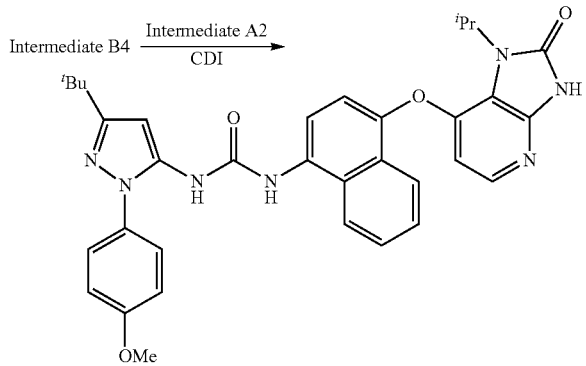

Example 12

To a solution of CDI (130 mg, 0.81 mmol) in dry DCM (1.0 mL) at RT was added Intermediate A2 (0.20 mg, 0.81 mmol) and the reaction mixture kept at RT for 2 hr. An aliquot of the resulting solution (0.90 mL, 0.70 mmol) was added dropwise to a solution of Intermediate B4 (100 mg, 0.30 mmol) in dry THF (1.0 mL) and the reaction mixture was maintained at RT and after 1 hr was treated with an additional portion of the preformed CDI adduct (25 μL, 20 μmol). After 3 days at RT the resulting mixture was partitioned between DCM (5.0 mL) and sat aq. NaHCO$_3$ (5.0 mL). The organic layer was separated and dried and then treated with activated charcoal and evaporated in vacuo. The residue was purified by flash column chromatography (SiO$_2$, 12 g, MeOH in DCM, 0-5%, gradient elution) to afford the title compound, Example 12 as a pale brown solid (95 mg, 51%); R$^t$ 2.34 min (Method 2); m/z 606 (M+H)$^+$, (ES$^+$); $^1$H NMR (400 MHz, DMSO-d$_6$) δ: 1.27 (9H, s), 1.52 (6H, d), 3.83 (3H, s), 4.92 (1H, m), 6.22 (1H, d), 6.38 (1H, s), 7.12 (2H, d), 7.30 (1H, d), 7.48 (2H, d), 7.62 (1H, ddd), 7.67 (1H, ddd), 7.73 (1H, d), 7.92 (1H, d), 7.97 (1H, dd), 8.09 (1H, d), 8.72 (1H, br s), 9.12 (1H, br s), 11.71 (1H, br s).

Example 13

1-(3-(tert-Butyl)-1-(4-methoxyphenyl)-1H-pyrazol-5-yl)-3-(2,3-dichloro-4-((1-methyl-2-oxo-2,3-dihydro-1H-imidazo[4,5-b]pyridin-7-yl)oxy)phenyl)urea

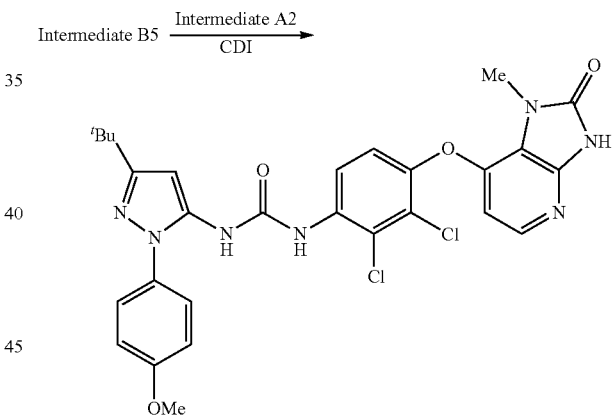

Example 13

To a solution of CDI (170 mg, 1.0 mmol) in dry DCM (1.5 mL) at RT was added Intermediate A2 (260 g, 1.00 mmol) in DCM (2.0 mL) and the reaction mixture maintained at RT for 18 hr. An aliquot of the resulting solution (0.15 mL, 0.1 mmol) was added to a solution of Intermediate B5 (11 mg, 0.035 mmol) in dry THF (2.0 mL) and the reaction mixture was kept at RT for 7 hr and then treated with an additional aliquot of the preformed CDI adduct (30 μL). After 24 hr the reaction was partitioned between DCM (25 mL) and sat aq. NaHCO$_3$ (25 mL). The aq layer was separated and was extracted with DCM (20 mL) and the combined organic extracts were dried and evaporated in vacuo. The residue was purified by flash column chromatography (SiO$_2$, 4.0 g, MeOH in DCM, 0-5%, gradient elution) to afford the title compound, Example 13 as a pale brown solid (11 mg, 48%); R$^t$ 2.26 min (Method 2); m/z 596/598 (M+H)$^+$ (ES$^+$); $^1$H NMR (400 MHz, DMSO-d$_6$) δ: 1.27 (9H, s), 3.49 (3H, s), 3.82 (3H, s), 6.37 (2H, overlapping m), 7.10 (2H, m), 7.38 (1H, d), 7.42 (2H, m), 7.79 (1H, d), 8.14 (1H, d), 8.5 (1H, br s), 9.14 (1H, br s), 11.70 (1H, br s).

Example 14

1-(3-(tert-Butyl)-1-(4-methoxyphenyl)-1H-pyrazol-5-yl)-3-(8-((2-oxo-2,3-dihydro-1H-imidazo[4,5-b]pyridin-7-yl)oxy)quinolin-5-yl)urea Intermediate C1 $\xrightarrow{\text{1. Fe/AcOH}}_{\text{2. CDI}}$

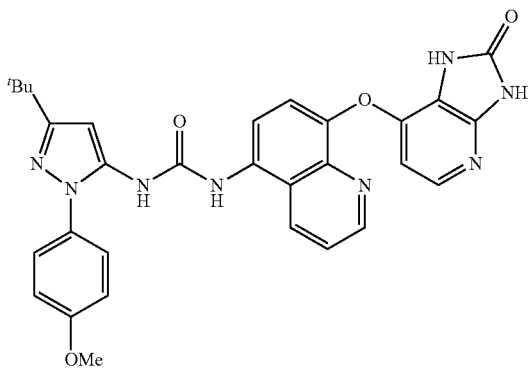

Example 14

A mixture of Intermediate C1 (510 mg, 0.900 mmol) and iron powder (250 mg, 4.5 o mmol) in AcOH (15 mL) was heated to 50° C. for 1.5 hr and was then cooled to RT and poured onto solid $K_2CO_3$ (18 g). The resulting mixture was extracted with THF (2×50 mL) and the combined extracts were evaporated in vacuo. The residue was partitioned between a mixture of EtOAc (100 mL) and MeOH (30 mL) and sat aq $NaHCO_3$ (30 mL). The organic layer was separated and was washed with water (30 mL) and brine (30 mL) and was then dried and evaporated in vacuo. The residue was triturated with ether (15 mL) to afford 1-(3-tert-butyl-1-(4-methoxyphenyl)-1H-pyrazol-5-yl)-3-(8-(2,3-diaminopyridin-4-yloxy)quinolin-5-yl)urea as a grey solid (230 mg, 45%); R$^t$ 1.58 min (Method 2); m/z 539 (M+H)$^+$, (ES$^+$).

To a solution of CDI (38 mg, 0.23 mmol) in dry DMF (1.0 mL) was added the diamine obtained above (100 g, 0.20 mmol) in a single portion and the reaction mixture maintained at RT for 4 days. An additional portion of CDI (30 mg, 0.20 mmol) was then added and after further 24 hr the reaction mixture was diluted with water (40 mL). The resulting precipitate was collected by filtration and was purified by flash column chromatography (SiO$_2$, 12 g, MeOH in DCM, 0-10%, gradient elution) to afford the title compound, Example 14, as a pale yellow solid (36 mg, 34%); R$^t$ 1.80 min (Method 2); m/z 565 (M+H)$^+$, (ES$^+$); $^1$H NMR (400 MHz, DMSO-d$_6$) δ: 1.28 (9H, s), 3.83 (3H, s), 5.97 (1H, d), 6.38 (1H, s), 7.11 (2H, d), 7.48 (2H, d), 7.59 (1H, d), 7.61-7.63 (2H, overlapping m), 7.97 (1H, d), 8.43 (1H, dd), 8.72 (1H, br d), 8.85 (1H, dd), 9.24 (1H, br s), 11.30 (1H, br s), 11.34 (1H, br s)

Example 15

1-(3-(tert-Butyl)-1-(p-tolyl)-1H-pyrazol-5-yl)-3-(4-((8-oxo-8,9-dihydro-7H-purin-6-yl)oxy)naphthalen-1-yl)urea Intermediate B6 $\xrightarrow{\text{Intermediate A1}}_{\text{CDI}}$

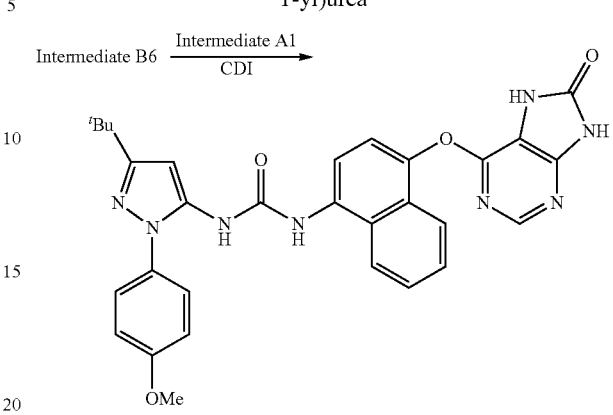

Example 15

To a solution of CDI (200 mg, 1.20 mmol) in dry DCM (2.5 mL) at RT was added Intermediate A1 (280 mg, 1.20 mmol) and the reaction mixture maintained at RT for 15 hr. An aliquot of the resulting solution (1.0 mL, 0.50 mmol) was added to a solution of Intermediate B6 (89 mg, 0.30 mmol) in dry THF (5.0 mL) and the reaction mixture was kept at RT for 3 days and was then partitioned between DCM (40 mL) and sat aq NaHCO$_3$ (40 mL). The aq layer was separated and was extracted with EtOAc (2×40 mL) and the combined organic extracts were dried over MgSO$_4$. The desiccant was removed by filtration and washed with THF/EtOAc (3:1 v/v, ×3). These washes were combined and evaporated in vacuo and the residue was purified by flash column chromatography (SiO$_2$, 12 g, MeOH in DCM, 0-8%, gradient elution). The impure product so obtained was triturated with ether to afford the title compound, Example 15 as a pale brown solid (57 mg, 33%); R$^t$ 1.80 min (Method 2); m/z 549 (M+H)$^+$, (ES$^+$); $^1$H NMR (400 MHz, DMSO-d$_6$) δ: 1.28 (9H, s), 2.40 (3H, s), 6.40 (1H, s), 7.37-7.39 (3H, overlapping m), 7.46 (2H, d), 7.54 (1H, ddd), 7.62 (1H, ddd), 7.86 (1H, d), 7.88 (1H, d), 8.02 (1H, s), 8.05 (1H, d), 8.76 (1H, br s), 9.09 (1H, br s), 11.6 (1H, br s), 11.9 (1H, br s).

Example 16

1-(3-(tert-Butyl)-1-(4-hydroxyphenyl)-1H-pyrazol-5-yl)-3-(4-((3-oxo-3,4-dihydropyrido[2,3-b]pyrazin-8-yl)oxy)naphthalen-1-yl)urea Intermediate D1 $\xrightarrow{\text{Intermediate A3}}_{\text{CDI}}$

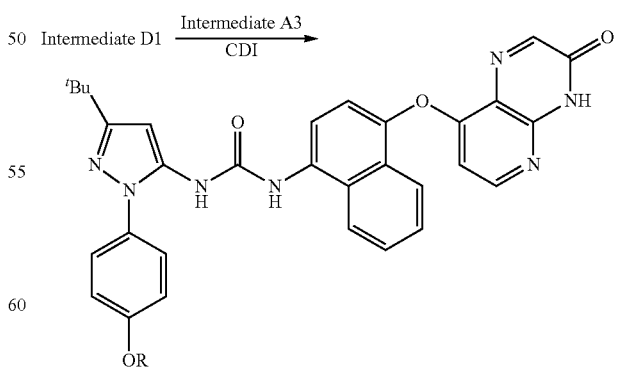

R = TBDMS $\xrightarrow{\text{TBAF}}$ R = H; Example 16

To a solution of CDI (160 mg, 0.99 mmol) in dry DCM (2.0 mL) at RT was added Intermediate A3 (340 mg, 0.99 mmol) and the reaction mixture maintained at RT for 4 days. An aliquot of the resulting solution (1.2 mL, 0.60 mmol) was added dropwise to a solution of Intermediate D1 (100 mg, 0.33 mmol) in dry THF (2.5 mL) and the reaction mixture kept at RT for 24 hr and then evaporated in vacuo. The residue was triturated with MeOH to furnish 1-(3-(tert-butyl)-1-(4-(((tert-butyldimethylsilyl)oxy)phenyl)-1H-pyrazol-5-yl)-3-(4-((3-oxo-3,4-di hydropyrido[2,3-b]pyrazin-8-yl)oxy)naphthalen-1-yl)urea as a grey solid (68 mg, 30%); $R^t$ 2.84 min (method 2); m/z 676 (M+H)$^+$, (ES$^+$).

To a solution of the silyl protected intermediate obtained above (68 mg, 0.10 mmol) in THF (1.5 mL) was added TBAF (1 M in THF, 100 μL, 0.1 mmol) and the reaction mixture kept at RT for 2.5 hr and then partitioned between EtOAc/THF (3:1 v/v, 50 mL) and sat aq NaHCO$_3$. The organic layer was separated and was washed with brine (50 mL) and with water (50 mL) and then dried and evaporated in vacuo. The residue was triturated with MeOH to afford the title compound, Example 16 as a beige solid (26 mg, 46%); $R^t$ 1.83 min (Method 2); m/z 562 (M+H)$^+$ (ES$^+$); $^1$H NMR (400 MHz, DMSO-d$_6$) δ: 1.28 (9H, s), 6.38-6.40 (2H, overlapping m), 6.94 (2H, m), 7.35 (2H, m), 7.40 (1H, d), 7.58 (1H, m), 7.67 (1H, m), 7.84 (1H, d), 7.99 (1H, d), 8.10 (1H, d), 8.26-8.28 (2H, overlapping m), 8.71 (1H, s), 9.17 (1H, br s), 9.83 (1H, br s), 12.98 (1H, br s).

Example 17

1-(3-(tert-Butyl)-1-(4-(hydroxymethyl)phenyl)-1H-pyrazol-5-yl)-3-(4-((3-oxo-3,4-dihydropyrido[2,3-b]pyrazin-8-yl)oxy)naphthalen-1-yl)urea

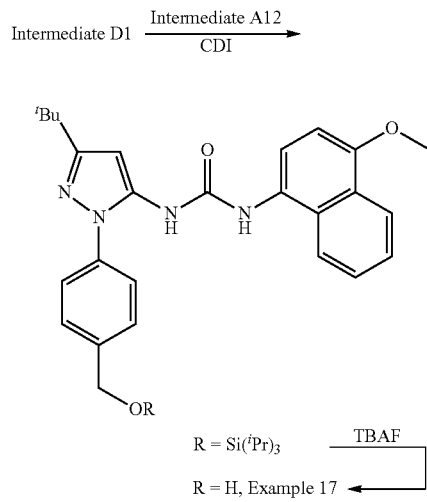

To a solution of CDI (2.06 g, 12.7 mmol) in dry DCM (40 mL) at RT was added Intermediate A12 (5.10 g, 12.7 mmol) in DCM (10 mL) and the reaction mixture kept at RT for 4 hr. An aliquot of the resulting solution (2.1 mL, 0.53 mmol) was added to a solution of Intermediate D1 (89 mg, 0.29 mmol) in dry THF (4.0 mL) and the reaction mixture maintained at RT and treated with additional aliquots of CDI adduct after 17 hr (1.1 mL, 0.28 mmol) and 23 hr (1.1 mL, 0.28 mmol). After 2 days the reaction mixture was partitioned between DCM (40 mL) and sat aq. NaHCO$_3$ (40 mL). The aq layer was separated and was extracted with DCM (40 mL) and the combined organic extracts were dried and evaporated in vacuo. The residue was purified by flash column chromatography (SiO$_2$, 12 g, MeOH in DCM, 0-4%, gradient elution) to afford 1-(3-(tert-butyl)-1-(4-(((triisopropylsilyl)oxy)methyl)phenyl)-1H-pyrazol-5-yl)-3-(4-((3-oxo-3,4-dihydropyrido[2,3-b]pyrazin-8-yl)oxy)naphthalen-1-yl)urea as an off-white solid (52 mg, 22%); $R^t$ 3.21 min (Method 2); m/z 732 (M+H)$^+$, (ES$^+$).

To a solution of the silyl protected intermediate obtained above (51 mg, 0.070 mmol) in THF (1.75 mL) under N$_2$ at 0° C. was added TBAF (1M solution in THF, 77 μL, 0.077 mmol) and the reaction mixture then warmed to RT. After 2 hr the mixture was partitioned between water (25 mL) and 2-methyltetrahydrofuran (25 mL). The organic layer was separated and washed with brine (25 mL) and was then dried and evaporated in vacuo. The residue was triturated with ether and the residue was purified by flash column chromatography (SiO$_2$, 12 g, MeOH in DCM, 0-10%, gradient elution) to afford the title compound, Example 17 as a pale yellow solid (24 mg, 58%); $R^t$ 1.87 min (Method 2); m/z 576 (M+H)$^+$, (ES$^+$); $^1$H NMR (400 MHz, DMSO-d$_6$) δ: 1.31 (9H, s), 4.59 (2H, d), 5.09 (1H, br s), 6.39 (1H, s), 6.44 (1H, d), 7.32 (1H, d), 7.49 (2H, d), 7.55 (2H, d), 7.56 (1H, t), 7.65 (1H, t), 7.90 (1H, s), 7.92 (1H, s), 8.12 (1H, d), 8.21 (1H, s), 8.27 (1H, d), 8.66 (1H, br s), 9.00 (1H, brs), 12.7 (1H, br s).

Example 18

1-(3-(tert-Butyl)-1-(4-(hydroxymethyl)-3-methoxyphenyl)-1H-pyrazol-5-yl)-3-(4-((3-oxo-3,4-dihydropyrido[2,3-b]pyrazin-8-yl)oxy)naphthalen-1-yl)urea

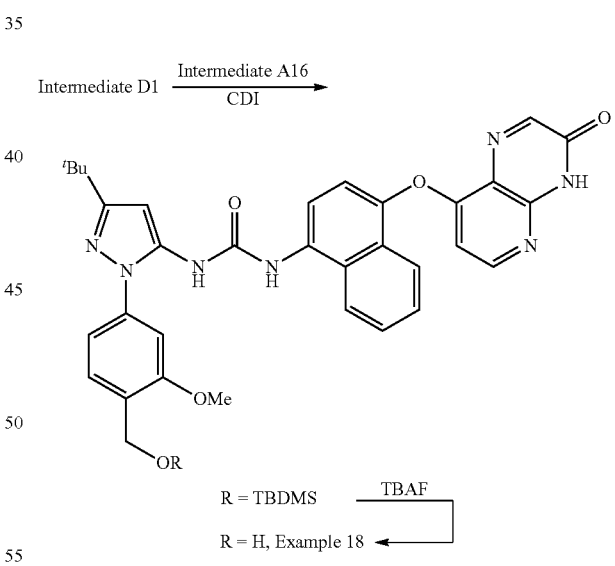

To a solution of CDI (96 mg, 0.59 mmol) in dry DCM (1.2 mL) at RT was added Intermediate A16 (240 mg, 0.59 mmol) and the reaction mixture maintained at RT for 24 hr. An aliquot of the resulting solution (0.60 mL, 0.30 mmol) was added to a solution of Intermediate D1 (60 mg, 0.20 mmol) in dry THF (2.0 mL) and the reaction mixture was kept at RT for 3 hr and was then partitioned between DCM (20 mL) and sat aq. NaHCO$_3$ (20 mL). The organic layer was separated and was washed with brine (20 mL) and dried and evaporated in vacuo. The residue was triturated with DCM to afford 1-(3-tert-butyl-1-(4-((tert-butyldimethylsilyloxy) methyl)-3-methoxyphenyl)-1H-pyrazol-5-yl)-3-(4-(3-oxo-3,4-dihydropyrido[2,3-b]pyrazin-8-yl oxy)naphthalen-1-yl)urea as a yellow solid (113 mg, 78%); R$^t$ 2.95 min (method 2); m/z 720 (M+H)$^+$, (ES$^+$).

To a solution of the silyl protected intermediate obtained above (110 mg, 0.150 mmol) in THF (2.5 mL) under N$_2$ at 00° C. was added TBAF (1M solution in THF, 0.19 mL, 0.19 mmol) and the mixture warmed to RT for 2.5 hr. An additional aliquot of TBAF (1M solution in THF, 0.19 mL, 0.19 mmol) was added and after 16 hr the mixture was partitioned between DCM (5.0 mL) and sat aq NaHCO$_3$ (10 mL). The organic layer was separated and was washed with brine (10 mL) and then dried and evaporated in vacuo. The residue was triturated with MeOH to afford the title compound, Example 18 as a yellow solid (28 mg, 30%); R$^t$ 1.84 min (Method 2); m/z 606 (M+H)$^+$, (ES$^+$); $^1$H NMR (400 MHz, DMSO-d$_6$) δ: 1.29 (9H, s), 3.85 (3H, s), 4.57 (2H, d), 5.15 (1H, t), 6.39 (1H, d), 6.43 (1H, s), 7.14-7.16 (2H, overlapping m), 7.39 (1H, d), 7.54 (1H, d), 7.57 (1H, ddd), 7.66 (1H, ddd), 7.85 (1H, dd), 7.97 (1H, d), 8.11 (1H, d), 8.25 (1H, d), 8.27 (1H, d), 8.81 (1H, br s), 9.18 (1H, br s), 12.95 (1H, br s).

Example 19

1-(3-(tert-Butyl)-1-(4-methoxyphenyl)-1H-pyrazol-5-yl)-3-(2,3-dichloro-4-((3-oxo-3,4-dihydropyrido[2,3-b]pyrazin-8-yl)oxy)phenyl)urea

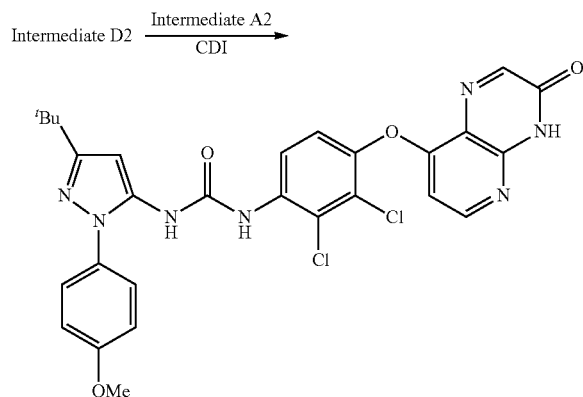

Example 19

To a solution of CDI (110 mg, 0.700 mmol) in dry DCM (1.5 mL) at RT was added Intermediate A2 (170 mg, 1.20 mmol) and the reaction mixture maintained at RT for 4 hr. An aliquot of the resulting solution (1.2 mL, 0.60 mmol) was added to a solution of Intermediate D2 (650 mg, 0.200 mmol) in dry THF (3.0 mL) and the reaction mixture was kept at RT for 3 days and was then partitioned between DCM (30 mL) and sat aq NaHCO$_3$ (30 mL). The aq layer was separated and was extracted with DCM (20 mL) and the combined organic extracts were washed with brine (25 mL), dried and evaporated in vacuo. The residue was purified by flash column chromatography (SiO$_2$, 12 g, MeOH in DCM, 0-7%, gradient elution) to afford the title compound, Example 19 as a pale brown solid (52 mg, 43%); R$^t$ 2.27 min (Method 2); m/z 594/596 (M+H)$^+$, (ES$^+$); $^1$H NMR (400 MHz, DMSO-d$_6$) δ: 1.27 (9H, s), 3.82 (3H, s), 6.37 (1H, s), 6.55 (1H, d), 7.10 (2H, d), 7.40 (1H, d), 7.43 (1H, d), 8.17 (1H, d), 8.20 (1H, s), 8.36 (1H, d) 8.86 (1H, br s), 9.15 (1H, br s), 13.0 (1H, br s).

Example 20

1-(3-(tert-Butyl)-1-(6-methoxypyridin-3-yl)-1H-pyrazol-5-yl)-3-(4-((3-oxo-3,4-dihydropyrido[2,3-b]pyrazin-8-yl)oxy)naphthalen-1-yl)urea

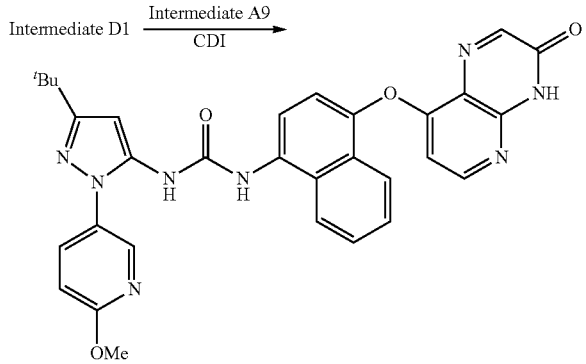

Example 20

To a solution of CDI (160 mg, 0.98 mmol) in dry DCM (2.5 mL) at RT was added Intermediate A9 (270 mg, 0.99 mmol) and the reaction mixture kept at RT for 2 hr. The resulting solution was added dropwise to a solution of Intermediate D1 (100 mg, 0.33 mmol) in dry THF (2.5 mL) and the reaction mixture was maintained at RT for 18 hr and was then evaporated in vacuo. The residue was triturated with MeOH to furnish a lilac-coloured solid (63 mg). A portion of this solid (30 mg) was purified by preparative HPLC to afford the title compound, Example 20 as an off-white solid (15 mg, 16% pro rata); R$^t$ 1.97 min (Method 2); m/z 577 (M+H)$^+$, (ES$^+$); $^1$H NMR (400 MHz, DMSO-d$_6$) δ: 1.29 (9H, s), 3.94 (3H, s), 6.39-6.42 (2H, overlapping m), 7.02 (1H, d), 7.39 (1H, d), 7.54 (1H, m), 7.66 (1H, m), 7.85 (1H, d), 7.89-7.95 (2H, overlapping m), 8.08 (1H, d), 8.25-8.27 (2H, overlapping m), 8.39 (1H, d), 8.80 (1H, br s), 9.10 (1H, br s), 12.95 (1H, br s).

Example 21

1-(3-(tert-Butyl)-1-(5-methylthiophen-2-yl)-1H-pyrazol-5-yl)-3-(4-((3-oxo-3,4-dihydropyrido[2,3-b]pyrazin-8-yl)oxy)naphthalen-1-yl)urea

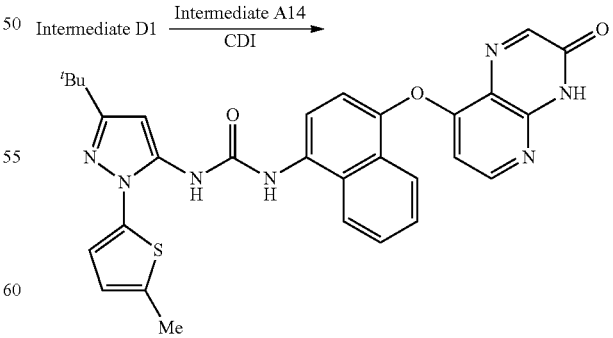

Example 21

To a solution of CDI (100 mg, 0.590 mmol) in dry DCM (1.0 mL) at RT was added Intermediate A14 (140 mg, 0.590 mmol) and the reaction mixture was maintained at RT for 16 hr. A portion of the resulting solution (0.60 mL, 0.30 mmol) was added dropwise to a solution of Intermediate D1 (60 mg, 0.20 mmol) in dry THF (2.0 mL) and the reaction mixture was kept at RT. A precipitate formed after 5 min and after 1 hr this was collected by filtration and washed with MeOH to afford the title compound, Example 21 as a yellow solid (80 mg, 71%); R$^t$ 2.18 min (Method 2); m/z 564 (M+H)$^+$, (ES$^+$); $^1$H NMR (400 MHz, DMSO-d$_6$) δ: 1.28 (9H, s), 2.28 (3H, s), 6.41-6.42 (2H, overlapping m), 7.10-7.12 (2H, overlapping m), 7.40 (1H, d), 7.59 (1H, m), 7.70 (1H, m), 7.88 (1H, d), 7.97 (1H, d), 8.17 (1H, d), 8.26-8.28 (2H, overlapping m), 8.87 (1H, s), 9.26 (1H, s), 12.96 (1H, s).

Example 22

1-(3-(tert-Butyl)-1-(4-methoxyphenyl)-1H-pyrazol-5-yl)-3-(4-((7-oxo-7,8-dihydropteridin-4-yl)oxy)naphthalen-1-yl)urea

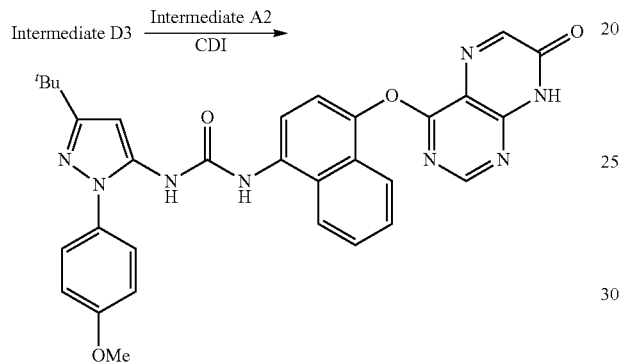

Example 22

To a solution of CDI (66 mg, 0.40 mmol) in dry DCM (1.5 mL) at RT was added Intermediate A2 (99 mg, 0.41 mmol) in DCM (1.5 mL) and the reaction mixture maintained at RT for 18 hr. The resulting solution was added to a solution of Intermediate D3 (90 mg, 0.12 mmol) in dry DCM (2.5 mL), after which DIPEA (47 μL, 0.27 mmol) was added and the mixture kept at RT for 2 hr. The reaction was quenched with MeOH (6.0 mL) and the mixture was evaporated onto silica and then purified by flash column chromatography (SiO$_2$, 12 g, MeOH in DCM, 0-100%, gradient elution). The impure material so obtained was purified by preparative HPLC to afford the title compound, Example 22 as an off white solid (1.5 mg, 2%); R$^t$ 2.10 min (Method 2); m/z 577 (M+H)$^+$ (ES$^+$); $^1$H NMR (400 MHz, DMSO-d$_6$) δ: 1.28 (9H, s), 3.84 (3H, s), 6.40 (1H, s), 7.12 (2H, d), 7.37 (1H, d), 7.48 (2H, d), 7.52 (1H, ddd), 7.61 (1H, ddd), 7.77 (1H, d), 7.90 (1H, d), 8.05 (1H, d), 8.07 (1H, s), 8.26 (1H, d), 8.76 (1H, s), 9.13 (1H, s).

Example 23

1-(3-tert-butyl-1-(4-methoxyphenyl)-1H-pyrazol-5-yl)-3-(4-((3-oxo-3,4-dihydropyrido[3,2-b]pyrazin-8-yl)methoxy)naphthalen-1-yl)urea

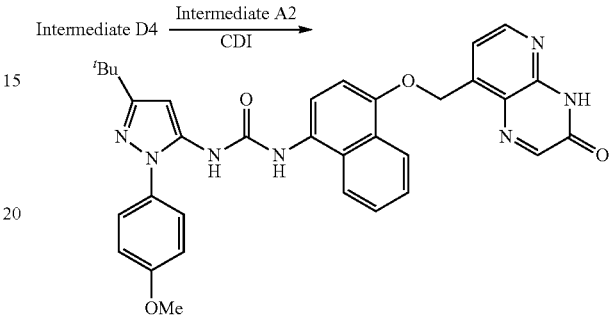

Example 23

To a solution of CDI (77 mg, 0.47 mmol) in dry DCM (500 μL) at RT was added Intermediate A2 (120 mg, 0.81 mmol) and the reaction mixture maintained at RT for 10 min, warmed to 40° C. for 5 min and then re-cooled to RT. After a further 1 hr the solution was diluted with DCM (500 μL) and an aliquot of this solution (75 μL, 0.06 mmol) was added to a suspension of Intermediate D4 (7.5 mg, 85% pure, 0.02 mmol) in dry THF (1.0 mL) The reaction mixture was kept at RT for 1.5 hr and was then quenched by the addition of MeOH (1.0 mL) and evaporated in vacuo. The residue was triturated with MeOH (1.5 mL) then washed with MeOH (2×1 mL) and dried in vacuo to afford the title compound, Example 23 as a yellow solid (8.5 mg, 68%); R$^t$ 2.26 min (Method 2); m/z 590 (M+H)$^+$, (ES$^+$); $^1$H NMR (400 MHz, DMSO-d$_6$) δ: 1.26 (9H, s), 3.83 (3H, s), 5.81 (2H, s), 6.34 (1H, s), 7.06 (1H, d), 7.11 (2H, m), 7.46 (2H, m), 7.58-7.62 (4H, overlapping m), 7.64 (1H, d), 7.92 (1H, m), 8.30 (1H, s), 8.35 (1H, m), 8.55 (1H, s), 8.60 (1H, d), 8.80 (1H, s), 13.0 (1H, br s).

Further compound examples of the invention were prepared employing the generic synthetic processes and the intermediates described herein above (Table 4).

TABLE 4

Additional Compound Examples of the Invention.

| Ex. No. | Structure | Compound Name & Analytical Data |
|---|---|---|
| 24 | (structure shown) | 1-(3-(tert-butyl)-1-(6-methoxypyridin-3-yl)-1H-pyrazol-5-yl)-3-(4-((1-methyl-2-oxo-2,3-dihydro-1H-imidazo[4,5-b]pyridin-7-yl)oxy)naphthalen-1-yl)urea. R$^t$ 2.09 min (Method 2); m/z 579 (M + H)$^+$ (ES$^+$); $^1$H NMR δ: 1.28 (9H, s), 3.53 (3H, s), 3.94 (3H, s), 6.30 (1H, d), 6.41 (1H, s), 7.02 (1H, d), 7.25 (1H, d), 7.61 (1H, ddd), 7.66 (1H, ddd), 7.74 (1H, d), 7.86 (1H, d), 7.90 (1H, dd), 8.04-8.09 (2H, overlapping m), 8.39 (1H, d), 8.78 (1H, s), 9.06 (1H, s), 11.69 (1H, s). |

TABLE 4-continued

Additional Compound Examples of the Invention.

| Ex. No. | Structure | Compound Name & Analytical Data |
|---|---|---|
| 25 | 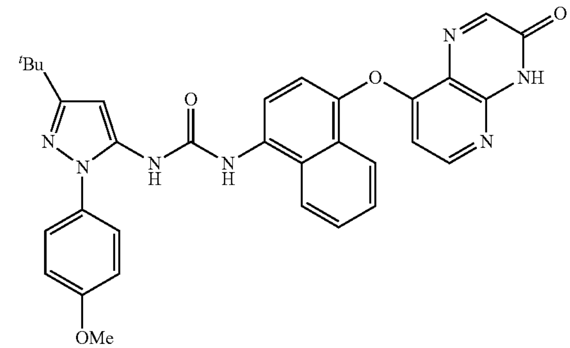 | 1-(3-(tert-butyl)-1-(4-methoxyphenyl)-1H-pyrazol-5-yl)-3-(4-((3-oxo-3,4-dihydropyrido[2,3-b]pyrazin-8-yl)oxy)naphthalen-1-yl)urea. $R^t$ 2.04 min (Method 2); m/z 576 $(M + H)^+$ $(ES^+)$; $^1H$ NMR δ: 1.29 (9H, s), 3.84 (3H, s), 6.38-6.40 (2H, overlapping m), 7.12-7.15 (2H, overlapping m), 7.40 (1H, d), 7.47-7.50 (2H overlapping m), 7.58 (1H, m), 7.66 (1H, m), 7.85 (1H, d), 7.98 (1H, d), 8.11 (1H, d), 8.26-8.28 (2H, overlapping m), 8.78 (1H, s), 9.18 (1H, s), 12.98 (1H, s) |
| 26 | 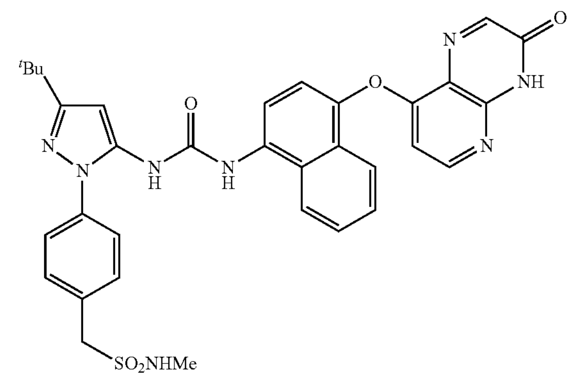 | 1-(4-(3-(tert-butyl)-5-(3-(4-((3-oxo-3,4-dihydropyrido[2,3-b]pyrazin-8-yl)oxy)naphthalen-1-yl)ureido)-1H-pyrazol-1-yl)phenyl)-N-methylmethanesulfonamide. $R^t$ 1.88 min (Method 2); m/z 653 $(M + H)^+$ $(ES^+)$; $^1H$ NMR δ: 1.29 (9H, s), 2.63 (3H, d), 4.43 (2H, s), 6.39 (1H, d), 6.43 (1H, s), 7.00 (1H, q), 7.39 (1H, d), 7.55 (2H, d), 7.57 (1H, m), 7.61 (2H, d), 7.68 (1H, ddd), 7.85 (1H, d), 7.95 (1H, d), 8.13 (1H, d), 8.25 (1H, s) 8.27 (1H, d), 8.86 (1H, s), 9.16 (1H, s), 12.95 (1H, s) |
| 27 | 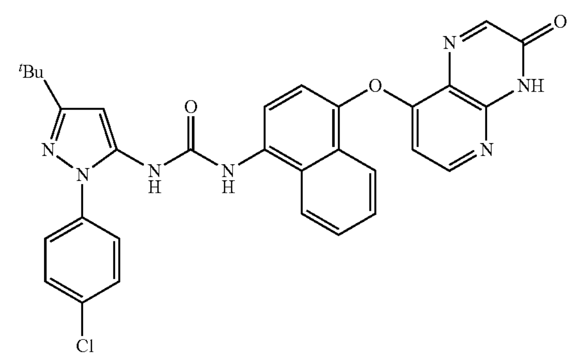 [SMILES: CC(C)(C)c1cc(NC(=O)Nc2ccc(Oc3ccnc4[nH]c(=O)cnc34)c3ccccc23)n(-c2ccc(Cl)cc2)n1] | 1-(3-(tert-butyl)-1-(4-chlorophenyl)-1H-pyrazol-5-yl)-3-(4-((3-oxo-3,4-dihydropyrido[2,3-b]pyrazin-8-yl)oxy)naphthalen-1-yl)urea. $R^t$ 2.23 min (Method 2); m/z 582 $(M + H)^+$ $(ES^+)$; $^1H$ NMR δ: 1.29 (9H, s), 6.39-6.42 (2H, overlapping m), 7.38 (1H, d), 7.56-7.69 (6H, overlapping m), 7.86 (1H, d), 7.92 (1H, d) 8.09 (1H, d), 8.25-8.27 (2H, overlapping m), 8.82 (1H, s), 9.11 (1H, s), 12.96 (1H, s). |
| 28 | 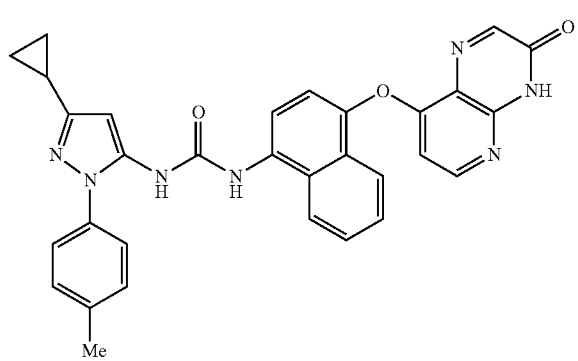 [SMILES: Cc1ccc(-n2nc(C3CC3)cc2NC(=O)Nc2ccc(Oc3ccnc4[nH]c(=O)cnc34)c3ccccc23)cc1] | 1-(3-cyclopropyl-1-(p-tolyl)-1H-pyrazol-5-yl)-3-(4-((3-oxo-3,4-dihydropyrido[2,3-b]pyrazin-8-yl)oxy)naphthalen-1-yl)urea. $R^t$ 1.95 min (Method 2); m/z 544 $(M + H)^+$ $(ES^+)$; $^1H$ NMR δ: 0.69 (2H, m), 0.89 (2H, m), 1.89 (1H, m), 2.40 (3H, s), 6.21 (1H, s), 6.39 (1H, d), 7.36-7.40 (3H, overlapping m), 7.44-7.46 (2H, overlapping m), 7.58 (1H, m), 7.67 (1H, m), 7.85 (1H, br d), 7.96 (1H, d), 8.09 (1H, br d), 8.25-8.27 (2H, overlapping m), 8.78 (1H, br s), 9.12 (1H, br s), 12.95 (1H, br s). |

TABLE 4-continued

Additional Compound Examples of the Invention.

| Ex. No. | Structure | Compound Name & Analytical Data |
|---|---|---|
| 29 | 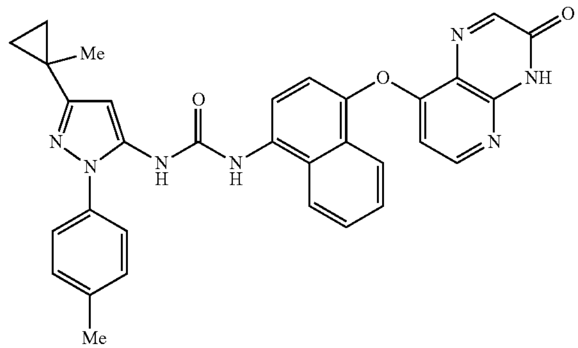 [SMILES: Cc1ccc(-n2nc(C3(C)CC3)cc2NC(=O)Nc2ccc(Oc3ccnc4[nH]c(=O)cnc34)c3ccccc23)cc1] | 1-(3-(1-methylcyclopropyl)-1-(p-tolyl)-1H-pyrazol-5-yl)-3-(4-((3-oxo-3,4-dihydropyrido[2,3-b]pyrazin-8-yl)oxy)naphthalen-1-yl)urea. R$^t$ 1.97 min (Method 2); m/z 558 (M + H)$^+$ (ES$^+$); $^1$H NMR δ: 0.73 (2H, m), 0.92 (2H, m), 1.41 (3H, s), 2.40 (3H, s), 6.28 (1H, s), 6.39 (1H, d), 7.37-7.40 (3H, overlapping m), 7.44-7.46 (2H, overlapping m), 7.58 (1H, m), 7.67 (1H, m), 7.86 (1H, d), 7.96 (1H, d), 8.10 (1H, d), 8.26-8.28 (2H, overlapping m), 8.77 (1H, br s), 9.13 (1H, br s), 12.95 (1H, br s). |
| 30 | 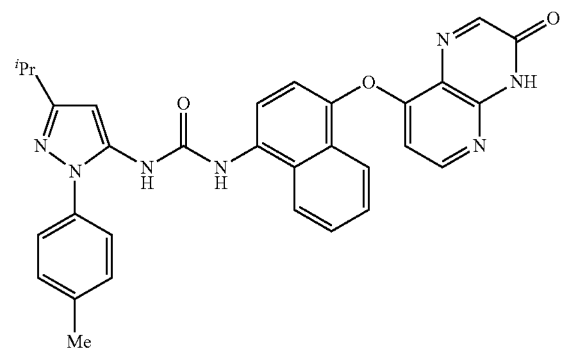 [SMILES: Cc1ccc(-n2nc(C(C)C)cc2NC(=O)Nc2ccc(Oc3ccnc4[nH]c(=O)cnc34)c3ccccc23)cc1] | 1-(3-isopropyl-1-(p-tolyl)-1H-pyrazol-5-yl)-3-(4-((3-oxo-3,4-dihydropyrido[2,3-b]pyrazin-8-yl)oxy)naphthalen-1-yl)urea. R$^t$ 2.05 min (Method 2); m/z 547 (M + H)$^+$ (ES$^+$); $^1$H NMR δ: 1.24 (6H, d), 2.41 (3H, s), 2.90 (1H, m), 6.37 (1H, s), 6.40 (1H, d), 7.37-7.41 (3H, overlapping m), 7.46-7.48 (2H, overlapping m), 7.58 (1H, m), 7.67 (1H, m), 7.86 (1H, br d), 7.98 (1H, d), 8.11 (1H, br d), 8.26-8.28 (2H, overlapping m), 8.79 (1H, br s), 9.14 (1H, br s), 12.95 (1H, br s). |
| 31 | 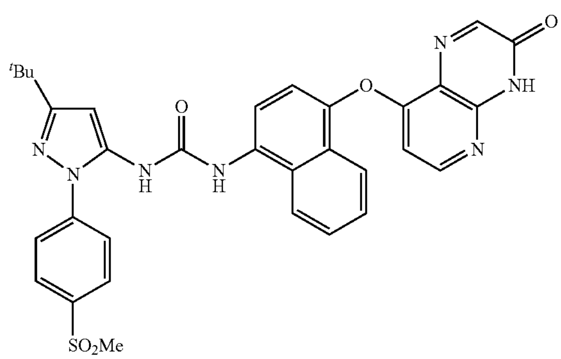 [SMILES: CC(C)(C)c1cc(NC(=O)Nc2ccc(Oc3ccnc4[nH]c(=O)cnc34)c3ccccc23)n(-c2ccc(S(C)(=O)=O)cc2)n1] | 1-(3-(tert-butyl)-1-(4-(methylsulfonyl)phenyl)-1H-pyrazol-5-yl)-3-(4-((3-oxo-3,4-dihydropyrido[2,3-b]pyrazin-8-yl)oxy)naphthalen-1-yl)urea. R$^t$ 1.93 min (Method 2); m/z 624 (M + H)$^+$ (ES$^+$); $^1$H NMR δ:1.31 (9H, s), 3.28 (3H, s), 6.40 (1H, d), 6.48 (1H, s), 7.39 (1H, d), 7.58 (1H, m), 7.68 (1H, m), 7.86 (1H, d), 7.90-7.92 (3H, overlapping m), 8.09-8.13 (3H, overlapping m), 8.25-8.27 (2H, overlapping m), 8.98 (1H, s), 9.14 (1H, s), 12.95 (1H, s). |
| 32 | 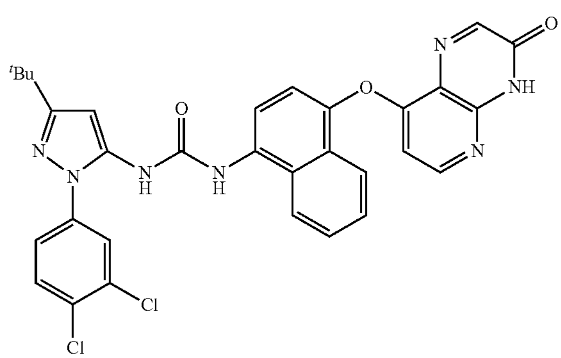 [SMILES: CC(C)(C)c1cc(NC(=O)Nc2ccc(Oc3ccnc4[nH]c(=O)cnc34)c3ccccc23)n(-c2ccc(Cl)c(Cl)c2)n1] | 1-(3-(tert-butyl)-1-(3,4-dichlorophenyl)-1H-pyrazol-5-yl)-3-(4-((3-oxo-3,4-dihydropyrido[2,3-b]pyrazin-8-yl)oxy)naphthalen-1-yl)urea. R$^t$ 2.40 min (Method 2); m/z 615 (M + H)$^+$ (ES$^+$); $^1$H NMR δ: 1.29 (9H, s), 6.40 (1H, d), 6.43 (1H, s), 7.38 (1H, d), 7.58 (1H, m), 7.63-7.69 (2H, overlapping m), 7.81-7.87 (3H, overlapping m), 7.91 (1H, d), 8.09 (1H, d), 8.25-8.27 (2H, overlapping m), 8.84 (1H, s), 9.12 (1H, s), 12.95 (1H, s). |

TABLE 4-continued

Additional Compound Examples of the Invention.

| Ex. No. | Structure | Compound Name & Analytical Data |
|---|---|---|
| 33 | 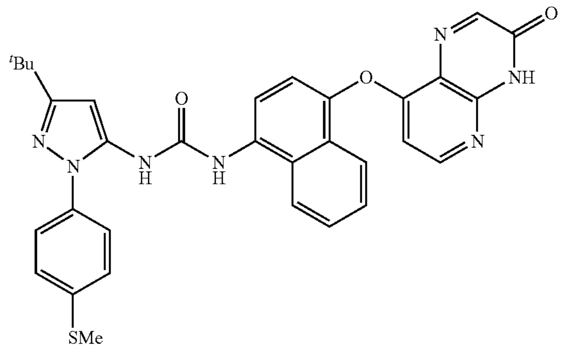 | 1-(3-(tert-butyl)-1-(4-(methylthio)phenyl)-1H-pyrazol-5-yl)-3-(4-((3-oxo-3,4-dihydro pyrido[2,3-b]pyrazin-8-yl)oxy)naphthalen-1-yl)urea. $R^t$ 2.19 min (Method 2); m/z 592 (M + H)$^+$ (ES$^+$); $^1$H NMR δ: 1.29 (9H, s), 2.54 (3H, s), 6.38-6.41 (2H, overlapping m), 7.39 (1H, d), 7.43-7.46 (2H, overlapping m), 7.51-7.54 (2H, overlapping m), 7.57 (1H, m), 7.66 (1H, m), 7.85 (1H, d), 7.96 (1H, d), 8.10 (1H, d), 8.25-8.27 (2H, overlapping m), 8.79 (1H, s), 9.13 (1H, s), 12.95 (1H, s). |

Example 34

A dry powder formulation may be prepared as follows:

A compound according to the invention such as 0.20 mg of a compound of formula (I) with a mass median diameter of 3 μm is blended with 12 mg milled lactose (wherein not greater than 85% of the particles have a mass median diameter of 60-90 μm and not less than 15% of particles have a mass median diameter of 15 μm. The resulting melange can then be filled into blisters, for example a peelable blister strip containing 60 blisters.

Example 35

An aerosol formulation containing a compound of formula (I) may be prepared as follows:

A compound according to the invention such as 250 μg of a compound of formula (I) with a mass median diameter of 3 μm, is mixed with 1,1,1,2-tetrafluoroethane 50 μL (amounts per actuation) in a total amount for 120 actuations. The formulation is then filled into a canister fitted with a metering valve adapted to dispense 50 μL.

Biological Profiling

The known p38 MAPK inhibitor BIRB 796 was tested in the assay systems for comparison purposes. The inhibitory potencies observed for the compound against the α isoform of the isolated p38 enzyme and against LPS-induced TNFα release from THP-1 cells were consistent with published results. A description of these assays follows below.

The inhibitory effects of compounds versus HRV-16 replication and poly I:C induced ICAM-1 expression were also determined.

Enzyme Inhibition Assay

The enzyme inhibitory activity of test compounds was determined by fluorescence resonance energy transfer (FRET) using synthetic peptides labelled with both donor and acceptor fluorophores (Z-LYTE, Invitrogen). Recombinant, phosphorylated p38 MAPK γ (MAPK12:Millipore) was diluted in HEPES buffer, mixed with compound at the desired final concentrations and incubated for 2 hr at RT. The FRET peptide (2 μM) and ATP (100 μM) were next added to the enzyme/compound mixture and incubated for 1 hr. Development reagent (protease) was added for 1 hr prior to detection in a fluorescence microplate reader.

The site-specific protease only cleaves non-phosphorylated peptide and eliminates the FRET signal. Phosphorylation levels of each reaction were calculated using the ratio of coumarin emission (donor) over fluorescein emission (acceptor) with high ratios indicating high phosphorylation levels and low ratios indicating low phosphorylation levels. The percentage inhibition of each reaction was calculated relative to non-inhibited control, and the 50% inhibitory concentration (IC$_{50}$ value) then calculated from the concentration-response curve.

For p38 MAPK alpha (MAPK14: Invitrogen), enzyme activity was evaluated indirectly by determining activation/phosphorylation of the down-stream molecule, MAPKAP-K2. The p38 MAPK α protein was mixed with compound for 2 hr at RT. The FRET peptide (2 μM), which is a phosphorylation target for MAPKAP-K2, inactive MAPKAP-K2 (Invitrogen) and ATP (10 μM) were then added to the enzymes/compound mixture and incubated for 1 hr. Development reagent was then added and the mixture incubated for 1 hr before detection by fluorescence completed the assay protocol.

The enzyme inhibitory activity of compound was determined by fluorescence resonance energy transfer (FRET) using synthetic peptides labelled with both donor and acceptor fluorophores (Z'-LYTE, Invitrogen).

For HCK assay, HCK enzyme (Invitrogen) was incubated with compound for 2 hr at RT. The FRET peptides (Z'-LYTE™ kit-Tyrosine 2 peptide) (2 μM) and 15 μM ATP solution were then added to the enzymes/compound mixtures and incubated for 1 hr. For the c-SRC assay, the FRET peptides (Z'-LYTE™ kit-Tyrosine 2 peptide) (2 μM) and 200 μM ATP solutions were then added to the cSrc enzyme (invitrogen)/compound mixtures and incubated for 1 hr. After development reagent was added, the mixtures were incubated for 1 hr and the assay protocol was completed by detection of the fluorescence levels in a microplate reader (Varioskan® Flash, ThermoFisher Scientific).

As we have reported in WO2011/070369 (herein incorporated by reference in its entirety), HCK inhibitory activity is associated with activity against influenza virus. The inventors have also discovered that inhibition of c-SRC is associated with activity against rhinovirus (see unpublished international patent application based on GB1010196.2, herein incorporated by reference in its entirety).

LPS-Induced TNFα/IL-8 Release in d-U937Cells.

U937 cells, a human monocytic cell line, were differentiated to macrophage-type cells by incubation with phorbol myristate acetate (PMA; 100 ng/mL) for 48 to 72 hr, whereupon the cells become adherent. Cells were pre-incubated with final concentrations of test compound for 2 hr and were then stimulated with 0.1 µg/mL of LPS (from E. Coli: 0111:B4, Sigma) for 4 hr. The supernatant was collected for determination of TNFα and IL-8 concentrations by sandwich ELISA (Duo-set, R&D systems). The inhibition of TNFα production was calculated as a percentage of that achieved by 10 µg/mL of BIRB796 at each concentration of test compound by comparison against vehicle control. The relative 50% effective concentration ($REC_{50}$) was determined from the resultant concentration-response curve. The inhibition of IL-8 production was calculated at each concentration of test compound by comparison with vehicle control. The 50% inhibitory concentration ($IC_{50}$) was determined from the resultant concentration-response curve.

LPS-Induced TNFα Release in THP-1 Cells.

THP-1 cells, a human monocytic cell line, were stimulated with 3 µg/mL of LPS (from E. Coli; 0111:B4, Sigma) for 4 hr and the supernatant collected for determination of the TNFα concentration by sandwich ELISA (Duo-set, R&D systems). The inhibition of TNFα production was calculated at each concentration by comparison with vehicle control. The 50% inhibitory concentration ($IC_{50}$) was determined from the resultant concentration-response curve.

Poly I:C-Induced ICAM-1 Induction in BEAS2B Cells.

Poly I:C (1 µg/mL) (Invivogene Ltd., San Diego, Calif.) was transfected into BEAS2B cells (human bronchial epithelial cells, ATCC) with Oligofectamine (Invitrogen, Carlsbad, Calif.). Cells were pre-incubated with final concentrations of test compounds for 2 hr and the level of ICAM1 expression on the cell surface was determined by cell-based ELISA. At a time point 18 hr after poly I:C transfection, cells were fixed with 4% formaldehyde in PBS and then endogenous peroxidase was quenched by the addition of 0.1% sodium azide and 1% hydrogen peroxide. Cells were washed with wash-buffer (0.1% Tween in PBS: PBS-Tween) and after blocking the wells with 5% milk in PBS-Tween for 1 hr, the cells were incubated with anti-human ICAM-1 antibody (Cell Signaling Technology, Danvers, Mass.) in 1% BSA PBS overnight at 4° C. The cells were washed with PBS-Tween and incubated with the secondary antibody (HRP-conjugated anti-rabbit IgG, Dako Ltd., Glostrup, Denmark). The ICAM-1 signal was detected by adding substrate and reading the absorbance at 450 nm against a reference wavelength of 655 nm using a spectrophotometer. The cells were then washed with PBS-Tween and total cell numbers in each well were determined by reading absorbance at 595 nm after Crystal Violet staining and elution by 1% SDS solution. The measured OD 450-655 readings were corrected for cell number by dividing with the OD595 reading in each well. The inhibition of ICAM-1 expression was calculated at each concentration of test compound by comparison with vehicle control. The 50% inhibitory concentration ($IC_{50}$) was determined from the resultant concentration-response curve.

We have used poly I:C challenge as a simple pharmacological challenge which mimics many of the consequences of virus infection.

Rhinovirus-Titre Assay.

MRC5 cells (human lung fibroblast, ATCC) were infected with 1 MOI (multiplicity of infection of 1.0) of HRV16 and incubated for 1 hr at 33° C. with gentle shaking to stimulate adsorption. The cells were then washed with PBS, fresh media was added and the cells were incubated for a further 96 hr. The supernatant was collected and 10-fold serial dilutions of virus containing supernatant were prepared. All titrations were performed by infecting confluent Hela cell monolayers with serially diluted supernatant ($10^{-1}$-$10^{-5}$) and assessing the cytopathic effect by visual inspection 4 days after infection. The amount of virus required to infect 50% of Hela cells was calculated in each treatment as $TCID_{50}$. Test compounds (0.04 µg/mL) were added 2 hr before HRV infection and 1 hr after infection when non-infected HRV was washed out. The anti-HRV activity of each test compound was determined as the difference of the log $TCID_{50}$ of HRV16 in the presence of the compound with the log $TCID_{50}$ of HRV16 in the absence of compound. The comparative potency of test compounds was then expressed as a ratio of their anti-viral activity, relative to the known anti-HRV agent Pleconaril, at a fixed dose (0.1 µg/mL). Anti-HRV activities were also shown as inhibitory % of $TCID_{50}$ vs. HRV16 infected control.

MTT Assay: Cell Viability

Differentiated U937 cells were pre-incubated with each test compound under two protocols: the first for 4 hr in 5% FCS and the second in 10% FCS for 24 h. The supernatant was replaced with 200 µL of new media and 10 µL of MTT stock solution (5 mg/mL) was added to each well. After incubation for 1 hr the media were removed, 200 µL of DMSO was added to each well and the plates were shaken lightly for 1 hr prior to reading the absorbance at 550 nm. The percentage loss of cell viability was calculated for each well relative to vehicle (0.5% DMSO) treatment. Consequently an apparent increase in cell viability for drug treatment relative to vehicle is tabulated as a negative percentage.

TABLE 1

Enzyme Inhibitory Profiles of BIRB796 and Compound Examples

| Test Compound Example No | Enzyme Profile: $IC_{50}$ Values (nM) | | | |
|---|---|---|---|---|
| | p38α | p38γ | HCK | cSrc |
| BIRB 796 | 12 | 296 | >1894 | >1894 |
| Ref. 1 | 5 | 402 | 47 | 162 |
| Ref 2 | 12 | 344 | 3 | 5 |
| 1 | 17 | 74 | <2 | 7 |
| 2 | 5 | 67 | <2 | 36 |
| 3 | 1 | 24 | 2 | 4 |
| 4 | 18 | 214 | 7 | 0.9 |
| 5 | 2 | 43 | 3 | 5 |
| 6 | 3 | 72 | 3 | 9 |
| 7 | 3 | 100 | 3 | 7 |
| 8 | 7 | 99 | 5 | 7 |
| 9 | 21 | 119 | <2 | 7 |
| 10 | 6 | 45 | 3 | 7 |
| 11 | 2 | 348 | 5 | 9 |
| 12 | 11 | 495 | 8 | 12 |
| 13 | 7 | 23 | 4 | 5 |
| 14 | 5 | 180 | <2 | 0.8 |
| 15 | 30 | 539 | 36 | 35 |
| 16 | 4 | 45 | 18 | 10 |
| 17 | 7 | 318 | 24 | 11 |
| 18 | 5 | 24 | 5 | 6 |
| 19 | 2 | 35 | 4 | 7 |
| 20 | 6 | 44 | 3 | 8 |
| 21 | 2 | 41 | 3 | 17 |
| 22 | 17 | 2620 | 458 | 406 |
| 23 | 12 | 193 | 22 | 35 |
| 24 | 7 | 126 | 5 | 16 |
| 25 | 4 | 50 | 5 | 12 |
| 26 | 7 | 29 | 3 | 13 |
| 27 | 3 | 237 | 918 | 16 |
| 28 | 2 | >18000 | 9 | 22 |
| 29 | 5 | 19 | 4 | 10 |
| 30 | 2 | 39 | 4 | 8 |

TABLE 1-continued

Enzyme Inhibitory Profiles of BIRB796 and Compound Examples

| Test Compound | Enzyme Profile: IC$_{50}$ Values (nM) | | | |
|---|---|---|---|---|
| Example No | p38α | p38γ | HCK | cSrc |
| 31 | 5 | 47 | 3 | 6 |
| 32 | 4 | 89 | 4 | 6 |
| 33 | 5 | 74 | 4 | 7 |

TABLE 2

Cellular Profiles of BIRB 796 and Compound Examples

| | Test Compd | | | | | | |
|---|---|---|---|---|---|---|---|
| Example No | THP1 (LPS) | d-U937 (LPS) | BEAS2B (polyIC) | NBEC (HRV) | | d-U937 | |
| | TNFα IC$_{50}$ (nM) | TNFα REC$_{50}$ (nM) | IL-8 IC$_{50}$ (nM) | ICAM1 IC$_{50}$ (nM) | HRV titre Relative anti-viral activity$^a$ (inhibitory %)$^b$ | MTT Assay$^c$ 4 h | 24 h |
| BIRB 796 | 4.1 | 4.8 | >1894 | 3530 | NE (28$^b$) | –$^d$ | –$^d$ |
| Ref. 1 | 2.3 | 0.9 | 92 | 618 | 1 (96$^b$) | –$^d$ | –$^d$ |
| Ref. 2 | 13 | 0.13 | 1.3 | 2.1 | 100 (100$^b$) | – | – |
| 1 | 1.6 | 0.2 | 19 | 2.7 | 0.1 (94) | – | – |
| 2 | 1.4 | 3.0 | 7.5 | 9.8 | 1 (60) | – | – |
| 3 | 0.7 | 1.1 | 17 | 4.1 | 0.2 (36) | – | – |
| 4 | 185 | 171 | 378 | 581 | 0.7 (60) | – | – |
| 5 | 13 | 6.2 | 4.1 | 6.6 | (36) | – | – |
| 6 | 0.7 | 1.1 | 5.2 | 11 | (80) | – | – |
| 7 | 7.0 | 1.7 | 4.2 | 3.0 | (60) | – | – |
| 8 | 2.5 | 0.3 | 1.7 | 0.6 | (91) | – | – |
| 9 | 1.6 | 3.1 | 27 | 24 | 3.2 (36) | – | – |
| 10 | 0.6 | 1.3 | 1.0 | 6.0 | (91) | – | – |
| 11 | 4.0 | 0.7 | 1.6 | 3.6 | (60) | – | – |
| 12 | 1.3 | 0.5 | 1.1 | 1.9 | (94) | – | – |
| 13 | 0.6 | 0.6 | 4.6 | 6.2 | ND | – | + |
| 14 | 163 | 166 | 726 | 675 | 1.5 (8) | – | – |
| 15 | 126 | 33 | 164 | >182 | (8) | – | – |
| 16 | 116 | 55 | 47 | 172 | (8) | – | – |
| 17 | 14 | 12 | 24 | 14 | (36) | – | – |
| 18 | 17 | 12 | 7.4 | 15 | (80) | – | – |
| 19 | 2.1 | 1.3 | 1.6 | 0.6 | (80) | – | – |
| 20 | 13 | 3.4 | 16 | 21 | (36) | – | – |
| 21 | 11 | 7.1 | 3.3 | 17 | (80) | – | – |
| 22 | >1733 | >1733 | >1733 | >173 | (8) | – | – |
| 23 | ND | 30 | 90 | 23 | ND | – | – |
| 24 | 4.4 | 1.3 | 11 | 12 | (91) | – | – |
| 25 | 1.6 | 1.8 | 8.1 | 8.3 | (36) | – | – |
| 26 | 75 | 1.9 | 1.6 | 207 | (−300) | – | – |
| 27 | 7.5 | 1.6 | 1.1 | 2.2 | (94) | – | – |
| 28 | 161 | 40 | 71 | >184 | (36) | – | – |
| 29 | 17 | 5.6 | 6.7 | 13 | (60) | – | – |
| 30 | 34 | 1.1 | 4.3 | 27 | (36) | – | – |
| 31 | 62 | 60 | 68 | 178 | (8) | – | – |
| 32 | 8.8 | 5.5 | 7.0 | 10 | (80) | – | – |
| 33 | 13 | 8.2 | 9.4 | 3.2 | (80) | – | – |

$^a$Relative anti-viral activity at 0.04 µg/mL vs. pleconaril at 0.1 µg/mL. Figure in parentheses is the % inhibition observed vs. HRV16 infection control;
$^b$performed at 0.2 µg/mL;
$^c$Cell viability screen:
− and + indicate the result is below and above the no significant effect threshold, respectively (<30% inhibition at a concentration of 1 µg/ml) at the time point indicated;
$^d$ performed at 10 µg/mL
ND: not determined;
NE: no effect These data demonstrate the anti-inflammatory and anti-viral potential of the tested compounds.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:

1. An inhaler device comprising a formulation of compound of formula (I):

(I)

J represents:

Q is N or —CH—;
X is O or O—CH$_2$—;
Y is —CH= or N;
Z is O, NR$^4$, —CR$^{4a}$=N— or —N=CR$^{4a}$— whereby the latter two groups, together with the atoms to which they are attached, form a 6 membered ring;
R$^1$ is C$_{1-6}$ alkyl, branched or unbranched, or C$_{3-6}$ cycloalkyl, each optionally substituted by a hydroxyl group;
R$^{2a}$ is H, halo, saturated or unsaturated branched or unbranched C$_{1-8}$ alkylene chain, wherein one or more carbons are optionally replaced by a heteroatom(s) independently selected from —O—, —N— and/or S(O)$_m$ and the chain is optionally substituted by one or more halogen atoms;
R$^{2b}$ is H, halo, C$_{1-6}$ alkoxy or C$_{1-6}$ alkyl optionally substituted by OH;
R$^2$ and R$^3$ each independently represent H, C$_{1-4}$ alkyl, halogen; C$_{1-4}$ haloalkyl, O(C$_{1-4}$ alkyl), O(C$_{1-4}$ haloalkyl), CN, SO$_2$R$^5$, C(O)OR$^6$ with the proviso that R$^2$ and R$^3$ do not both represent H concomitantly, or
R$^2$ and R$^3$ together with the carbons to which they are attached form a six membered aromatic ring or a heteroaromatic ring comprising a nitrogen atom;
R$^4$ is H, C$_{1-5}$ alkyl, C$_{2-5}$ alkenyl, C$_{2-5}$ alkynyl, C$_{3-6}$ cycloalkyl, C$_{3-6}$ cycloalkenyl, C$_6$ aryl, a 5 or 6 membered heteroaryl or a 5 or 6 membered heterocyclic group, wherein said aryl, heteroaryl or heterocyclic group is substituted with 0 to 3 substituents selected from halogen, hydroxyl, C$_{1-6}$ alkyl, C$_{1-6}$ alkoxy, C$_{1-6}$ haloalkyl, amino, C$_{1-4}$ mono or di-alkyl amino, C$_{1-4}$ mono or di-acyl amino, S(O)$_q$C$_{1-6}$ alkyl, C$_{0-6}$ alkylC(O)C$_{1-6}$ alkyl or C$_{0-6}$ alkylC(O)C$_{1-6}$ heteroalkyl;
R$^{4a}$ is H or C$_{1-3}$ alkyl;
R$^5$ is H or C$_{1-4}$ alkyl;
R$^6$ is H or C$_{1-4}$ alkyl;
m is 0, 1 or 2;
q is 0, 1 or 2;
a pharmaceutically acceptable salt thereof, including all stereoisomers, tautomers and isotopic derivatives thereof in particulate form, wherein the mass mean aerodynamic diameter (MMAD) of the population of particles is in the range 1 to 20 microns.

2. A compound selected from:
1-(3-tert-butyl-1-p-tolyl-1H-pyrazol-5-yl)-3-(4-(2-oxo-2,3-dihydro-1H-imidazo[4,5-b]pyridin-7-yloxy)naphthalen-1-yl)urea;

1-(3-tert-butyl-1-(4-methoxyphenyl)-1H-pyrazol-5-yl)-3-(4-(2-oxo-2,3-dihydro-1H-imidazo[4,5-b]pyridin-7-yloxy)naphthalen-1-yl)urea;

1-(3-tert-butyl-1-phenyl-1H-pyrazol-5-yl)-3-(4-(2-oxo-2,3-dihydro-1H-imidazo[4,5-b]pyridin-7-yloxy)naphthalen-1-yl)urea;

1-(3-tert-butyl-1-p-tolyl-1H-pyrazol-5-yl)-3-(4-(1-methyl-2-oxo-2,3-dihydro-1H-imidazo[4,5-b]pyridin-7-yloxy)naphthalen-1-yl)urea;

1-(3-tert-butyl-1-(4-methoxyphenyl)-1H-pyrazol-5-yl)-3-(4-(1-methyl-2-oxo-2,3-dihydro-1H-imidazo[4,5-b]pyridin-7-yloxy)naphthalen-1-yl)urea;

1-(3-tert-butyl-1-phenyl-1H-pyrazol-5-yl)-3-(8-(2-oxo-2,3-dihydro-1H-imidazo[4,5-b]pyridin-7-yloxy)quinolin-5-)urea;

1-(3-tent-butyl-1-(4-methoxyphenyl)-1H-pyrazol-5-yl)-3-(8-(2-oxo-2,3-dihydro-1H-imidazo[4,5-b]pyridin-7-yloxy)quinolin-5-yl)urea;

1-(3-(tert-Butyl)-1-(4-methoxyphenyl)-1H-pyrazol-5-yl)-3-(4-((2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(4-((1-methyl-2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(4-((1-ethyl-2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(4-((1-isopropyl-2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(2,3-dichloro-4-((1-methyl-2-oxo-2,3-dihydro-1H-imidazo[4,5-b]pyridin-7-yl)oxy)pheny)urea;

1-(3-(tert-Butyl)-1-(4-methoxyphenyl)-1H-pyrazol-5-yl)-3-(8-((2-oxo-2,3-dihydro-1H-imidazo[4,5-b]pyridin-7-yl)oxy)quinolin-5-yl)urea;

1-(3-(tert-Butyl)-1-(p-tolyl)-1H-pyrazol-5-yl)-3-(4-((8-oxo-8,9-dihydro-7H-purin-6-yl)oxy) naphthalen-1-yl)urea;

1-(3-(tert-Butyl)-1-(4-hydroxyphenyl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-(hydroxymethyl)phenyl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-(hydroxymethyl)-3-methoxyphenyl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-methoxyphenyl)-1H-pyrazol-5-yl)-3-(2,3-dichloro-4-((3-oxo-3,4-dihydropyrido[2,3-b]pyrazin-8-yl)oxy)phenyl)urea;

1-(3-(tert-Butyl)-1-(6-methoxypyridin-3-yl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(5-methylthiophen-2-yl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-methoxyphenyl)-1H-pyrazol-5-yl)-3-(4-((7-oxo-7,8-dihydropteridin-4-yl)oxy)naphthalen-1-yl)urea;

1-(3-(tert-butyl)-1-(6-methoxypyridin-3-yl)-1H-pyrazol-5-yl)-3-(4-((1-methyl-2-oxo-2,3-dihydro-1H-imidazo[4,5-b]pyridin-7-yl)oxy)naphthalen-1-yl)urea;

1-(3-(tert-butyl)-1-(4-methoxyphenyl)-1H-pyrazol-5-yl)-3-(4((3-oxo-3,4-dihydropyrido[2,3-b]pyrazin-8-yl)oxy)naphthalen-1-yl)urea;

1-(4-(3-(tert-butyl)-5-(3-(4-((3-oxo-3,4-dihydropyrido[2,3-b]pyrazin-8-yl)oxy)naphthalen-1-yl)ureido)-1H-pyrazol-1-yl)phenyl)-N-methylmethanesulfonamide;

1-(3-(tert-butyl)-1-(4-chlorophenyl)-1H-pyrazol-5-yl)-3-(4-((3-oxo-3,4-dihydropyrido[2,3-b]pyrazin-8-yl)oxy)naphthalen-1-yl)urea;

1-(3-cyclopropyl-1-(p-tolyl)-1H-pyrazol-5-yl)-3-(4-((3-oxo-3,4-dihydropyrido[2,3-b]pyrazin-8-yl)oxy)naphthalen-1-yl)urea;

1-(3-(1-methylcyclopropyl)-1-(p-tolyl)-1H-pyrazol-5-yl)-3-(4-((3-oxo-3,4-dihydropyrido[2,3-b]pyrazin-8-yl)oxy)naphthalen-1-ylurea;

1-(3-isopropyl-1-(p-tolyl)-1H-pyrazol-5-yl)-3-(4-((3-oxo-3,4-dihydropyrido[2,3-b]pyrazin-8-yl)oxy)naphthalen-1-yl)urea;

1-(3-(tert-butyl)-1-(4-(methylsulfonyl)phenyl)-1H-pyrazol-5-yl)-3-(4-((3-oxo-3,4-dihydropyrido[2,3-b]pyrazin-8-yl)oxy)naphthalen-1-yl)urea;

1-(3-(tert-butyl)-1-(3,4-dichlorophenyl)-1H-pyrazol-5-yl)-3-(4-((3-oxo-3,4-dihydropyrido[2,3-b]pyrazin-8-yl)oxy)naphthalen-1-yl)urea;

1-(3-(tert-butyl)-1-(4-(methylthio)phenyl)-1H-pyrazol-5-yl)-3-(4-((3-oxo-3,4-dihydropyrido[2,3-b]pyrazin-8-yl)oxy)naphthalen-1-yl)urea;

and pharmaceutically acceptable salts of any one thereof, including all stereoisomers, tautomers and isotopic derivatives thereof.

3. A compound of claim 2 selected from:

1-(3-tert-butyl-1-(4-methoxyphenyl)-1H-pyrazol-5-yl)-3-(4-(1-methyl-2-oxo-2,3-dihydro-1H-imidazo[4,5-b]pyridin-7-yloxy)naphthalen-1-yl)urea;

1-(3-tert-butyl-1-(4-methoxyphenyl)-1H-pyrazol-5-yl)-3-(8-(2-oxo-2,3-dihydro-1H-imidazo[4,5-b]pyridin-7-yloxy)quinolin-5-yl)urea;

1-(3-(tert-Butyl)-1-(4-methoxyphenyl)-1H-pyrazol-5-yl)-3-(4-((2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(4-((1-methyl-2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(4-((1-ethyl-2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(4-((1-isopropyl-2-oxo-2,3-dihydro-1H-imidazo[4,5-b]pyridin-7-yl)oxy)naphthalen-1-yl)urea;

1-(3-(tert-Butyl)-1-(4-methoxyphenyl)-1H-pyrazol-5-yl)-3-(2,3-dichloro-4-((1-methyl-2-oxo-2,3-dihydro-1H-imidazo[4,5-b]pyridin-7-yl)oxy)phenyl)urea;

1-(3-(tert-Butyl)-1-(4-methoxyphenyl)-1H-pyrazol-5-yl)-3-(8-((2-oxo-2,3-dihydro-1H-imidazo[4,5-b]pyridin-7-yl)oxy)quinolin-5-yl)urea;

1-(3-(tert-Butyl)-1-(p-tolyl)-1H-pyrazol-5-yl)-3-(4-((8-oxo-8,9-dihydro-7H-purin-6-yl)oxy) naphthalen-1-yl)urea;

1-(3-(tert-Butyl)-1-(4-hydroxyphenyl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-(hydroxymethyl)phenyl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-(hydroxymethyl)-3-methoxyphenyl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-methoxyphenyl)-1H-pyrazol-5-yl)-3-(2,3-dichloro-4-((3-oxo-3,4-dihydropyrido[2,3-b]pyrazin-8-yl)oxy)phenyl)urea;

1-(3-(tert-Butyl)-1-(6-methoxypyridin-3-yl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(5-methylthiophen-2-yl)-1H-pyrazol-5-yl)-3-(4-((3-oxo-3,4-dihydropyrido[2,3-b]pyrazin-8-yl)oxy)naphthalen-1-yl)urea;

1-(3-(tert-Butyl)-1-(4-methoxyphenyl)-1H-pyrazol-5-yl)-3-(4-((7-oxo-7,8-dihydropteridin-4-yl)oxy)naphthalen-1-yl)urea;

1-(3-(tert-butyl)-1-(6-methoxypyridin-3-yl)-1H-pyrazol-5-yl)-3-(4-((1-methyl-2-oxo-2,3-dihydro-1H-imidazo[4,5-b]pyridin-7-yl)oxy)naphthalen-1-yl)urea;

1-(3-(tert-butyl)-1-(4-methoxyphenyl)-1H-pyrazol-5-yl)-3-(4-((3-oxo-3,4-dihydropyrido[2,3-b]pyrazin-8-yl)oxy)naphthalen-1-yl)urea;

1-(4-(3-(tert-butyl)-5-(3-(4-((3-oxo-3,4-dihydropyrido[2,3-b]pyrazin-8-yl)oxy)naphthalen-1-yl)ureido)-1H-pyrazol-1-yl)phenyl)-N-methylmethanesulfonamide;

1-(3-(tert-butyl)-1-(4-chlorophenyl)-1H-pyrazol-5-yl)-3-(4-((3-oxo-3,4-dihydropyrido[2,3-b]pyrazin-8-yl)oxy)naphthalen-1-yl)urea;

1-(3-cyclopropyl-1-(p-tolyl)-1H-pyrazol-5-yl)-3-(4-((3-oxo-3,4-dihydropyrido[2,3-b]pyrazin-8-yl)oxy)naphthalen-1-yl)urea;

1-(3-(1-methylcycropropyl)-1-(p-tolyl)-1H-pyrazol-5-yl)-3-(4-((3-oxo-3,4-dihydropyrido[2,3-b]pyrazin-8-yl)oxy)naphthalen-1-ylurea;

1-(3-isopropyl-1-(p-tolyl)-H-pyrazol-5-yl)-3-(4-((3-oxo-3,4-dihydropyrido[2,3-b]pyrazin-8-yl)oxy)naphthalen-1-yl)urea;

1-(3-(tert-butyl)-1-(4-(methylsulfonyl)phenyl)-1H-pyrazol-5-yl)-3-(4-((3-oxo-3,4-dihydropyrido[2,3-b]pyrazin-8-yl)oxy)naphthalen-1-yl)urea;

1-(3-(tert-butyl)-1-(3,4-dichlorophenyl)-1H-pyrazol-5-yl)-3-(4-((3-oxo-3,4-dihydropyrido[2,3-b]pyrazin-8-yl)oxy)naphthalen-1-yl)urea;

1-(3-(tert-butyl)-1-(4-(methylthio)phenyl)-1H-pyrazol-5-yl)-3-(4-((3-oxo-3,4-dihydropyrido[2,3-b]pyrazin-8-yl)oxy)naphthalen-1-yl)urea;

and pharmaceutically acceptable salts of any one thereof, including all stereoisomers, tautomers and isotopic derivatives thereof.

\* \* \* \* \*